US007879338B2

(12) United States Patent
Hamilton et al.

(10) Patent No.: US 7,879,338 B2
(45) Date of Patent: Feb. 1, 2011

(54) VECTORS AND METHODS FOR IMMUNIZATION AGAINST NOROVIRUS USING TRANSGENIC PLANTS

(75) Inventors: William D.O. Hamilton, Herts (GB); Koen Hellendoorn, Suffolk (GB); Timothy D. Jones, Cambridgeshire (GB); Dwayne D. Kirk, Mesa, AZ (US); Hugh S. Mason, Phoenix, AZ (US); Xiuren Zhang, New York, NY (US); Charles J. Arntzen, Superstition Mountain, AZ (US)

(73) Assignee: Boyce Thompson Institute for Plant Research, Ithaca, NY (US)

( * ) Notice: Subject to any disclaimer, the term of this patent is extended or adjusted under 35 U.S.C. 154(b) by 543 days.

(21) Appl. No.: 10/895,791

(22) Filed: Jul. 21, 2004

(65) Prior Publication Data

US 2005/0155113 A1    Jul. 14, 2005

Related U.S. Application Data

(60) Provisional application No. 60/489,005, filed on Jul. 21, 2003.

(51) Int. Cl.
| | |
|---|---|
| C12N 15/40 | (2006.01) |
| C12N 5/04 | (2006.01) |
| C12N 1/21 | (2006.01) |
| A61K 39/125 | (2006.01) |
| A01H 5/00 | (2006.01) |
| A01H 5/08 | (2006.01) |
| A01H 5/10 | (2006.01) |

(52) U.S. Cl. ............... 424/216.1; 435/410; 435/411; 435/414; 435/417; 435/252.3; 536/23.72; 800/295; 800/317.2; 800/317.3; 800/317.4

(58) Field of Classification Search ............... 536/23.1, 536/23.72
See application file for complete search history.

(56) References Cited

U.S. PATENT DOCUMENTS

| | | | | |
|---|---|---|---|---|
| 6,392,121 | B1 * | 5/2002 | Mason et al. | ............... 800/287 |
| 6,572,862 | B1 | 6/2003 | Estes et al. | |

FOREIGN PATENT DOCUMENTS

| | | |
|---|---|---|
| WO | WO 90/02484 | 3/1990 |
| WO | WO 96/33739 | 10/1996 |
| WO | WO 01/17555 A2 | 3/2001 |

OTHER PUBLICATIONS

Murray et al., Codon usage in plant genes 1989 Nucleic Acid Research vol. 17, No. 3, pp. 477-498.*
Boyaka et al., Oral QS-21 Requires Early IL-4 Help for Induction of Mucosal and Systemic Immunity J Immunol 2001 vol. 166, pp. 2283-2290.*
Murata et al., Biosci. Biotechnol. Biochem. 2001 vol. 65, pp. 383-388.*
Ando et al., "Detection and Differentiation of Antigenically Distinct Small Round-Structured Viruses (Norwalk-Like Viruses) by Reverse Transcription-PCR and Southern Hybridization," *J. Clin. Microbio.* 33(1):64-71 (1995).
Arntzen, C. J., "Edible Vaccines," *Public Health Reports* 112:190-197 (1997).
Arntzen, C. J., "Edible Vaccines Produced in Transgenic Plants," *The Jordan Report; Accelerated Development of Vaccines* 1996:43-48 (1996).
Arntzen, C. J., "High-Tech Herbal Medicine: Plant-Based Vaccines," *Nature Biotech.* 15: 221-222 (1997).
Arntzen & Mason, "Oral Vaccine Production in the Edible Tissues of Transgenic Plants," in *New Generation Vaccines*, Levine, M. M., Woodrow, G.C., Kaper, J.B. & Cobon, G.S., Eds., Marcel Dekker Inc., New York, pp. 263-277 (1997).
Ball et al., "Oral Immunization with Recombinant Norwalk Virus-Like Particles Induces a Systemic and Mucosal Immune Response in Mice," *J. Virol.* 72:1345-1353 (1998).
Ball et al., "Recombinant Norwalk Virus-Like Particles Given Orally to Volunteers: Phase I Study," Gastroenterology 117:40-48 (1999).
Becker et al., "New Plant Binary Vectors with Selectable Markers Located Proximal to the Left T-DNA Border," *Plant Mol. Biol.* 20:1195-1197 (1992).
Belitz et al., "Fruits and Fruit Products," Chapter 18, Springer-Verlag, Germany, pp. 578-621 (1987).
Blacklow & Greenberg, "Viral Gastroenteritis," *N. Engl. J. Med.* 325(4):252-264 (1991).
Boyaka et al., "Oral QS-21 Requires Early IL-4 Help for Induction of Mucosal and Systemic Immunity," *J. Immuno.* 166:2283-2290 (2001).
Chavali et al., "Adjuvant Effects of Orally Administered Saponins on Humoral and Cellular Immune Responses in Mice," *Immunobiology* 174(3):347-359 (1987).
Chavali et al., "An in vitro Study of Immunomodulatory Effects of Some Saponins," *Int. J. Immunopharmac.* 9(6):675-683 (1987).
Clarke & Lambden, "Organization and Expression of Calicivirus Genes," *J. Infect. Dis.* 181(Suppl 2):S309-316 (2000).

(Continued)

*Primary Examiner*—Mary E Mosher
*Assistant Examiner*—Myron G Hill
(74) *Attorney, Agent, or Firm*—Nixon Peabody LLP

(57) ABSTRACT

The present invention relates to a synthetic plant-optimized nucleic acid molecule having a Norwalk virus capsid protein coding nucleotide sequence, and nucleic acid constructs, host cells, expression systems, and plants having the plant-optimized Norwalk virus nucleic acid molecule. The present invention also relates to a method of producing Norwalk virus capsid protein virus-like particles in a transgenic plant or transgenic plant seed transformed with a plant-optimized nucleic acid molecule encoding Norwalk virus capsid protein. The plant or a component thereof can be administered to a subject under conditions effective to immunize the subject against disease resulting from infection by a *Norovirus*, including Norwalk virus. An oral vaccine for immunization of a subject against Norwalk virus infection is also disclosed.

29 Claims, 33 Drawing Sheets

OTHER PUBLICATIONS

Deman, J.M., "Proteins—Nonenzymic Browning," In *Principles of Food Chemistry*, 3rd Edition, Kluwer Academic/Plenum Publishers, New York, New York, pp. 120-131 (1999).
Efimova et al., "Effect of Saponins of the Pericarp of *Sapindus mukorossi* G. on the Blood Pressure and Cholesterol in Animals," *Farm. Zh.* 21(6):45-49 (1966).
Engers et al., "Third Meeting on Novel Adjuvants Currently in or Close to Clinical Testing World Health Organization—Organisation Mondiale de la Santé, Fondation Mérieux, Annecy, France, Jan. 7-9, 2002," *Vaccine* 21:3503-3524 (2003).
Erickson et al., "The Structure of a T= 1 Icosahedral Empty Particle from Southern Bean Mosaic Virus," *Science* 229:625-629 (1985).
Estes et al., "Norwalk Virus Vaccines: Challenges and Progress," *J. Infect. Dis.* 181(Suppl 2): S367-S373 (2000).
Fankhauser et al., "Molecular Epidemiology of 'Norwalk-Like Viruses' in Outbreaks of Gastroenteritis in the United States," *J. Infect. Dis.* 178:1571-1578 (1998).
Flavell et al., "Selectable Marker Genes: Safe for Plants?" *Biotechnology* 10(2):141-144 (1992).
Frary & Hamilton, "Efficiency and Stability of High Molecular Weight DNA Transformation: An Analysis in Tomato," *Transgenic Res.* 10:121-132 (2001).
Friedman, M., "Tomato Glycoalkaloids: Role in the Plant and in the Diet," *J. Agric. Food Chem.* 50:5751-5780 (2002).
Fuchs et al., "Purification and Characterization of Microbially Expressed Neomycin Phosphotransferase II (NPTII) Protein and Its Equivalence to the Plant Expressed Protein," *Biotechnology* 11(13):1537-1542 (1993).
Fuchs et al., "Safety Assessment of the Neomycin Phosphotransferase II (NPTII) Protein," *Biotechnology* 11(13):1543-1547 (1993).
Gaunt et al., "Short-Term Toxicity of Quillaia Extract in Rats," *Fd. Cosmet. Toxicol.* 12:641-650 (1974).
Genbank Accession No. AAB50466 (Mar. 26, 1997).
Genbank Accession No. AB021987 (Dec. 2, 2003).
Genbank Accession No. AB021988 (Dec. 2, 2003).
Genbank Accession No. AB021989 (Dec. 2, 2003).
Genbank Accession No. AB021990 (Dec. 2, 2003).
Genbank Accession No. AB021991 (Dec. 2, 2003).
Genbank Accession No. AB021992 (Dec. 2, 2003).
Genbank Accession No. AB021993 (Dec. 2, 2003).
Genbank Accession No. AB021994 (Dec. 2, 2003).
Genbank Accession No. AB021995 (Dec. 2, 2003).
Genbank Accession No. AB021996 (Dec. 2, 2003).
Genbank Accession No. AB022679 (Sep. 1, 1999).
Genbank Accession No. AB031013 (Dec. 2, 2003).
Genbank Accession No. AB032758 (Nov. 21, 2003).
Genbank Accession No. AF145709 (Dec. 28, 2001).
Genbank Accession No. AF145896 (Nov. 19, 1999).
Genbank Accession No. AF156765 (Apr. 6, 2000).
Genbank Accession No. AF194182 (Feb. 9, 2000).
Genbank Accession No. AF195847 (Jul. 13, 2000).
Genbank Accession No. AF195848 (Jul. 13, 2000).
Genbank Accession No. AF312936 (Feb. 5, 2001).
Genbank Accession No. AF312937 (Feb. 5, 2001).
Genbank Accession No. AF359452 (Apr. 23, 2001).
Genbank Accession No. AF394960 (Jul. 11, 2001).
Genbank Accession No. AF397156 (Jul. 18, 2002).
Genbank Accession No. AF397905 (Aug. 20, 2001).
Genbank Accession No. AF414402 (Oct. 10, 2001).
Genbank Accession No. AF414403 (Oct. 10, 2001).
Genbank Accession No. AF414406 (Oct. 10, 2001).
Genbank Accession No. AF414407 (Oct. 10, 2001).
Genbank Accession No. AF414409 (Oct. 10, 2001).
Genbank Accession No. AF414423 (Oct. 10, 2001).
Genbank Accession No. AF414426 (Jun. 15, 2004).
Genbank Accession No. AF414427 (Oct. 10, 2001).
Genbank Accession No. AF425763 (Oct. 25, 2001).
Genbank Accession No. AF425764 (Oct. 25, 2001).
Genbank Accession No. AF425765 (Oct. 25, 2001).
Genbank Accession No. AF425766 (Oct. 25, 2001).
Genbank Accession No. AF425767 (Oct. 25, 2001).
Genbank Accession No. AF425768 (Oct. 25, 2001).
Genbank Accession No. AF425769 (Oct. 25, 2001).
Genbank Accession No. AF427111 (Oct. 25, 2001).
Genbank Accession No. AF427112 (Oct. 25, 2001).
Genbank Accession No. AF427113 (Oct. 25, 2001).
Genbank Accession No. AF427114 (Oct. 25, 2001).
Genbank Accession No. AF427115 (Oct. 25, 2001).
Genbank Accession No. AF427116 (Oct. 25, 2001).
Genbank Accession No. AF427117 (Oct. 25, 2001).
Genbank Accession No. AF427118 (Oct. 25, 2001).
Genbank Accession No. AF427119 (Oct. 25, 2001).
Genbank Accession No. AF427120 (Oct. 25, 2001).
Genbank Accession No. AF427121 (Oct. 25, 2001).
Genbank Accession No. AF427122 (Oct. 25, 2001).
Genbank Accession No. AF427123 (Oct. 25, 2001).
Genbank Accession No. AF435807 (Feb. 12, 2003).
Genbank Accession No. AF439267 (Nov. 19, 2001).
Genbank Accession No. AF472623 (Aug. 7, 2003).
Genbank Accession No. AF493224 (Jul. 10, 2002).
Genbank Accession No. AF539439 (Sep. 22, 2002).
Genbank Accession No. AF539440 (Sep. 22, 2002).
Genbank Accession No. AF542090 (Sep. 25, 2002).
Genbank Accession No. AJ004864 (Jan. 7, 1999).
Genbank Accession No. AJ277606 (Apr. 20, 2001).
Genbank Accession No. AJ277607 (Apr. 30, 2001).
Genbank Accession No. AJ277608 (Apr. 30, 2001).
Genbank Accession No. AJ277609 (Apr. 30, 2001).
Genbank Accession No. AJ277610 (Apr. 30, 2001).
Genbank Accession No. AJ277611 (Apr. 30, 2001).
Genbank Accession No. A1277612 (Apr. 30, 2001).
Genbank Accession No. AJ277613 (Apr. 30, 2001).
Genbank Accession No. AJ277614 (Apr. 30, 2001).
Genbank Accession No. AJ277615 (Apr. 30, 2001).
Genbank Accession No. AJ277616 (Apr. 30, 2001).
Genbank Accession No. AJ277617 (Apr. 30, 2001).
Genbank Accession No. AJ277618 (Apr. 15, 2001).
Genbank Accession No. AJ277619 (Apr. 30, 2001).
Genbank Accession No. AJ277620 (Apr. 30, 2001).
Genbank Accession No. AJ277621 (Apr. 30, 2001).
Genbank Accession No. AJ487807 (Nov. 29, 2002).
Genbank Accession No. AY030098 (Jan. 29, 2002).
Genbank Accession No. AY030312 (Jan. 29, 2002).
Genbank Accession No. AY030313 (Jan. 29, 2002).
Genbank Accession No. AY054299 (Oct. 22, 2001).
Genbank Accession No. AY054300 (Oct. 22, 2001).
Genbank Accession No. AY081134 (Mar. 18, 2002).
Genbank Accession No. AY130761 (Sep. 14, 2002).
Genbank Accession No. AY130762 (Sep. 14, 2002).
Genbank Accession No. AY145709 (Aug. 29, 2003).
Genbank Accession No. AY247431 (Dec. 1, 2003).
Genbank Accession No. AY247432 (Dec. 1, 2003).
Genbank Accession No. AY247433 (Dec. 1, 2003).
Genbank Accession No. AY247434 (Dec. 1, 2003).
Genbank Accession No. AY247435 (Dec. 1, 2003).
Genbank Accession No. AY247436 (Dec. 1, 2003).
Genbank Accession No. AY247437 (Dec. 1, 2003).
Genbank Accession No. AY247438 (Dec. 1, 2003).
Genbank Accession No. AY247439 (Dec. 1, 2003).
Genbank Accession No. AY247440 (Dec. 1, 2003).
Genbank Accession No. AY247441 (Dec. 1, 2003).
Genbank Accession No. AY247442 (Dec. 1, 2003).
Genbank Accession No. AY485642 (Dec. 22, 2003).
Genbank Accession No. AY580335 (Apr. 21, 2004).
Genbank Accession No. AY581254 (Sep. 14, 2004).
Genbank Accession No. L07418 (Mar. 27, 1996).
Genbank Accession No. L23828 (Jan. 9, 1995).
Genbank Accession No. M87661 (Mar. 26, 1997).
Genbank Accession No. U02030 (May 6, 2002).
Genbank Accession No. U07611 (Sep. 5, 2000).
Genbank Accession No. U07612 (Oct. 1, 1994).
Genbank Accession No. U22498 (Aug. 19, 1996).
Genbank Accession No. U46039 (May 21, 1996).

Genbank Accession No. U65427 (Jul. 21, 2005).
Genbank Accession No. U70059 (Oct. 2, 2000).
Genbank Accession No. U75682 (Oct. 6, 2000).
Genbank Accession No. X76716 (Aug. 1, 1994).
Genbank Accession No. X81879 (Apr. 18, 2005).
Genbank Accession No. X86557 (Apr. 18, 2005).
Guerrero et al., "Recombinant Norwalk Virus-Like Particles Administered Intranasally to Mice Induce Systemic and Mucosal (Fecal and Vaginal) Immune Responses.," *J. Virol.* 75:9713-9722 (2001).
Haq et al., "Oral Immunization with a Recombinant Bacterial Antigen Produced in Transgenic Plants," *Science* 268:714-716 (1995).
Hardy et al., "Antigenic Mapping of the Recombinant Norwalk Virus Capsid Protein Using Monoclonal Antibodies," *Virology* 217:252-261 (1996).
Harrison et al., "Virus Structure," in *Fields Virology*, 3rd Ed., Fields et al., eds., Lippincott-Raven Publishers, Philadelphia, PA, Chapter 3, pp. 59-99 (1996).
Heal et al., "Potentiation by a Novel Alkaloid Glycoside Adjuvant of a Protective Cytotoxic T Cell Immune Response Specific for a Preerythrocytic Malaria Vaccine Candidate Antigen," *Vaccine* 19:4153-4161 (2001).
Huang et al., "Virus-Like Particle Expression and Assembly in Plants: Hepatitis B and Norwalk Viruses," *Vaccine* 23:1851-1858 (2005).
Hutson et al., "Norovirus Disease: Changing Epidemiology and Host Susceptibility Factors," *TRENDS in Microbiol.* 12(6):279-287 (2004).
Jiang et al., "Expression, Self-Assembly, and Antigenicity of the Norwalk Virus Capsid Protein," *J. Virol.* 66:6527-6532 (1992).
Jiang et al., "Norwalk Virus Genome Cloning and Characterization," *Science* 250:1580-1583 (1990).
Jiang et al., "Sequence and Genomic Organization of Norwalk Virus," *Virology* 195:51-61 (1993).
Karst et al., "STAT1-Dependent Innate Immunity to a Norwalk-Like Virus," *Science* 299:1575-1578 (2003).
Kensil, C.R., "Saponins as Vaccine Adjuvants," *Critical Reviews™ in Therapeutic Drug Carrier Systems* 13 (1&2): 1-55 (1996).
Kim et al., "Hypocholesterolemic Property of *Yucca schidigera* and *Quillaja saponaria* Extracts in Human Body," *Arch. Pharm. Res.* 26(12):1042-1046 (2003).
Kirk et al., "Application of *Quillaja saponaria* Extracts as Oral Adjuvants for Plant-Made Vaccines," *Expert Opinion Biol. Ther.* 4(6):947-958 (2004).
Kirk et al., "Model Production of a Potent Plant-Made Vaccine," presentation at the 6th National Conference on Vaccine Research, National Foundation for Infectious Diseases, Arlington, Virginia (May 4-7, 2003) (Slide Presentation & Abstract).
Kong et al., "Oral Immunization with Hepatitis B Surface Antigen Expressed in Transgenic Plants," *Proc. Natl. Acad. Sci. USA* 98:11539-11544 (2001).
Lauterslager et al., "Oral Immunisation of Naive and Primed Animals with Transgenic Potato Tubers Expressing LT-B," *Vaccine* 19:2749-2755 (2001).
Leung & Rogers, "Hyperphagia After Ventral Tegmental Lesions and Food Intake Responses of Rats Fed Disproportionate Amounts of Dietary Amino Acids," *Physiol. Behavior* 25(3): 457-464 (1980).
Lindesmith et al., "Human Susceptibility and Resistance to Norwalk Virus Infection," *Nat. Med.* 9(5):548-553 (2003).
Lönneborg & Jensen, "Reliable and Reproducible Method to Extract High-Quality RNA from Plant Tissues Rich in Secondary Metabolites,"*0 BioTechniques* 29:714-718 (2000).
Mason et al., "Edible Vaccine Protects Mice Against *Escherichia coli* Heat-Labile Enterotoxin (LT): Potatoes Expressing a Synthetic LT-B Gene," *Vaccine* 16:1336-1343 (1998).
Mason et al., "Expression of Hepatitis B Surface Antigen in Transgenic Plants," *Proc. Natl. Acad. Sci. USA* 89:11745-11749 (1992).
Mason et al., "Expression of Norwalk Virus Capsid Protein in Transgenic Tobacco and Potato and its Oral Immunogenicity in Mice," *Proc. Natl. Acad. Sci. USA* 93:5335-5340 (1996).
Parkshionikar et al., "Waterborne Outbreak of Gastroenteritis Associated with a Norovirus ," *Appl. Enviro. Microbiol.* 69(9):5263-5268 (2003).
Phillips et al., "Long-term Toxicity Study of Quillaia Extract in Mice," *Fd. Cosmet. Toxicol.* 17:23-27 (1979).
Pink & Kieny, "Meeting Report: 4th Meeting on Novel Adjuvants Currently in/close to Human Clinical Testing," World Health Organization—Organisation Mondiale de la Santé, Fondation Mérieux, Annecy, France, 23-25 Jun. 2003, *Vaccine* 22:2097-2102 (2004).
Prasad et al., "X-ray Crystallographic Structure of the Norwalk Virus Capsid," *Science* 286:287-290 (1999).
Rajananthanan et al., "Evaluation of Novel Aggregate Structures as Adjuvants: Composition, Toxicity Studies and Humoral Responses," *Vaccine* 17:715-730 (1999).
Rajananthanan et al., "Novel Aggregate Structure Adjuvants Modulate Lymphocyte Proliferation and Th1 and Th2 Cytokine Profiles in Ovalbumin Immunized Mice," *Vaccine* 18:140-152 (1999).
Richter et al., "Production of Hepatitis B Surface Antigen in Transgenic Plants for Oral Immunization," *Nat. Biotechnol.* 18:1167-1171 (2000).
Richter et al., "Transgenic Plants Created for Oral Immunization Against Diarrheal Diseases," *J. Travel Med.* 3(1):52-56 (1996).
San Martín & Briones, "Quality Control of Commercial Quillaja (*Quillaja saponaria* Molina) Extracts by Reverse Phase HPLC," *J. Sci. Food Agri.* 80:2063-2068 (2000).
Sojikul et al., "A Plant Signal Peptide-Hepatitis B Surface Antigen Fusion Protein with Enhanced Stability and Immunogenicity Expressed in Plant Cells," *Proc. Natl. Acad. Sci. USA* 100:2209-2214 (2003).
Sosroseno, W., "A Review of the Mechanisms of Oral Tolerance and Immunotherapy," *J. Royal Soc. Med.* 88:14-17 (1995).
Tacket et al., "Immunogenicity of a Recombinant Bacterial Antigen Delivered in Transgenic Corn," 6th Annual Conference on Vaccine Research, National Foundation for Infectious Diseases, Arlington, VA (May 4-7, 2003) (Abstract).
Tacket et al., "Human Immune Responses to a Novel Norwalk Virus Vaccine Delivered in Transgenic Potatoes," *J. Infect. Dis.* 182:302-305 (2000).
Tacket et al., "Humoral, Mucosal, and Cellular Immune Responses to Oral Norwalk Virus-like Particles in Volunteers," *Clinical Immunolgy* 108:241-247 (2003).
Tacket et al., "Immunogenicity in Humans of a Recombinant Bacterial Antigen Delivered in a Transgenic Potato," *Nat. Med.* 4:407-609 (1998).
Tacket et al., "Immunogenicity of Recombinant LT-B Delivered Orally to Humans in Transgenic Corn," *Vaccine* 22(31-32):4385-4389 (2004).
Taniguchi et al., "Further Studies of 35-40-nm Virus-Like Particles Associated with Outbreaks of Acute Gastroenteritis," *J. Med. Microbiol.* 14:107-118 (1981).
Van Der Poel et al., "Norwalk-Like Calicivirus Genes in Farm Animals," *Emerging Infectious Diseases* 6(1):36-41 (2000).
Vinjé et al., "The Incidence and Genetic Variability of Small Round-Structured Viruses in Outbreaks of Gastroenteritis in The Netherlands," *J. Infect. Dis.* 176:1374-1378 (1997).
Waite et al., "Three Double-blind, Randomized Trials Evaluating the Safety and Tolerance of Different Formulations of the Saponin Adjuvant QS-21," *Vaccine* 19:3957-3967 (2001).
Walmsley et al., "Efficacy of an Edible, Plant-Derived Immunocontraceptive Vaccine in Mice and Voles," 6th Annual Conference on Vaccine Research, National Foundation for Infectious Diseases, Arlington, Virginia (May 4-7, 2003) (Abstract).
Walmsley et al., "Expression of the B Subunit of *Escherichia coli* Heat-Labile Enterotoxin as a Fusion Protein in Transgenic Tomato," *Plant Cell Rep.* 21:1020-1026 (2003).
Walmsley et al., "Passive Immunization of Mice Pups Through Oral Immunization of Dams with a Plant-Derived Vaccine," *Immunol. Lett.* 86(21):71-76 (2003).
White et al., "Attachment and Entry of Recombinant Norwalk Virus Capsids to Cultured Human and Animal Cells Lines," *J. Virol.* 70:6589-6597 (1996).
White et al., "Biochemical Characterization of a Smaller Form of Recombinant Norwalk Virus Capsids Assembled in Insect Cells," *J. Virol.* 71:8066-8072 (1997).

Zhang & Mason, "Limited Supply of the ORF3 Protein of Norwalk Virus (NV) Enhances Assembly of Recombinant Norwalk Virus-Like Particle (rNV VLPs)," 6$^{th}$ Annual Conference on Vaccine Research, National Foundation for Infectious Diseases, Arlington, Virginia (May 4-7, 2003).

Ball et al., "Recombinant Norwalk Virus-like Particles as an Oral Vaccine," Arch. Virol. Suppl. 12:243-9 (1996) (abstract only).

Blanchard & Hood, "Sequence to Array: Probing the Genome's Secrets," Nat. Biotechnology 14:1649 (1996) (abstract only).

Friedlander, "Human Immunity to a Virus Set Off for First Time With Plant-Based Vaccine," Cornell Chronicle 31 (40) (Jul. 13, 2000).

Genbank Accession No. AY360474 (Aug. 31, 2003).

Gonin et al., "Genetic Diversity and Molecular Epidemiology of Norwalk-Like Viruses," J. Infect. Dis. 182:691-697 (2000).

Green et al., "Comparison of the Reactivities of Baculovirus-Expressed Recombinant Norwalk Virus Capsid Antigen with Those of the Native Norwalk Virus Antigen in Serologic Assays and Some Epidemiologic Observations," J. Clin. Microbiol. 31(8):2185-2191 (1993).

Hale et al., "Expression and Self-Assembly of Grimsby Virus: Antigenic Distinction from Norwalk and Mexico Viruses," Clin. Diagnostic Lab. Immunol. 6(1):142-145 (1999).

Kitamoto et al., "Cross-Reactivity Among Several Recombinant Calicivirus Virus-Like Particles (VLPs) with Monoclonal Antibodies Obtained from Mice Immunized Orally with One Type of VLP," J. Clin. Microbiol. 40 (7):2459-2465 (2002).

Kobayashi et al., "Molecular Cloning, Expression, and Antigenicity of Seto Virus Belonging to Genogroup I Norwalk-Like Viruses," J. Clin. Microbiol. 38(9):3492-3494 (2000).

Lockhart et al., "Expression Monitoring by Hybridization to High-Density Oligonucleotide Arrays," Nat. Biotechnology 14:1675-1680 (1996).

* cited by examiner

```
                                1                                                 50
Native NVCP (SEQ ID NO: 1)   (1) ATGATGATGGCGTCTAAGGACGCTACATCAAGC-GTGGATGGCGCTAGT
sNVCP (SEQ ID NO: 3)         (1) ATGATGATGGCTTCTAAGGATGCTACATCAT-CTGTGGATGGAGCTAGT
Contig 1 (SEQ ID NO: 5)      (1) ATGATGATGGCKTCTAAGGAYGCTACATCAWGCTGTGGATGGMGCTAGT 51                                               100
Native NVCP (SEQ ID NO: 1)  (51) GGCGCTGGTCAGTTGGTACCGGAGGTTAATGCTTCTGACCCTCTTGCAAT
sNVCP (SEQ ID NO: 3)        (51) GGAGCTGGTCAATTGGTTCCAGAGGTTAATGCTTCTGACCCTCTTGCTAT
Contig 1 (SEQ ID NO: 5)     (51) GGMGCTGGTCARTTGGTWCCRGAGGTTAATGCTTCTGACCCTCTTGCWAT 101                                              150
Native NVCP (SEQ ID NO: 1) (101) GGATCCTGTAGCAGGTTCTTCGACAGCAGTCGCGACTGCTGGACAAGTTA
sNVCP (SEQ ID NO: 3)       (101) GGATCCTGTAGCAGGTTCTTCCACAGCAGTTGCTACTGCTGGACAAGTTA
Contig 1 (SEQ ID NO: 5)    (101) GGATCCTGTAGCAGGTTCTTCSACAGCAGTYGCKACTGCTGGACAAGTTA 151                                              200
Native NVCP (SEQ ID NO: 1) (151) ATCCTATTGATCCCTGGATAATTAATAATTTTGTGCAAGCCCCCCAAGGT
sNVCP (SEQ ID NO: 3)       (151) ATCCTATTGATCCATGGATAATTAACAACTTTGTGCAAGCCCCCCAAGGT
Contig 1 (SEQ ID NO: 5)    (151) ATCCTATTGATCCMTGGATAATTAAYAAYTTTGTGCAAGCCCCCCAAGGT 201                                              250
Native NVCP (SEQ ID NO: 1) (201) GAATTTACTATTTCCCCAAATAATACCCCCGGTGATGTTTTGTTTGATTT
sNVCP (SEQ ID NO: 3)       (201) GAATTCACTATTTCCCCAAACAACACCCCAGGTGATGTTTTGTTTGATTT
Contig 1 (SEQ ID NO: 5)    (201) GAATTYACTATTTCCCCAAAYAAYACCCCMGGTGATGTTTTGTTTGATTT 251                                              300
Native NVCP (SEQ ID NO: 1) (251) GAGTTTGGGTCCCCATCTTAATCCTTTCTTGCTCCATCTATCACAAATGT
sNVCP (SEQ ID NO: 3)       (251) GAGTTTGGGTCCCCATCTTAATCCTTTCTTGCTCCATCTCTCACAAATGT
Contig 1 (SEQ ID NO: 5)    (251) GAGTTTGGGTCCCCATCTTAATCCTTTCTTGCTCCATCTMTCACAAATGT
```

FIGURE 1 A

```
                                301                                                350
Native NVCP (SEQ ID NO: 1)  (301) ATAATGGTTGGGTTGGTAACATGAGAGTCAGGATTATGCTAGCTGGTAAT
sNVCP (SEQ ID NO: 3)        (301) ATAATGGTTGGGTTGGTAACATGAGAGTTAGGATTATGCTTGCTGGTAAT
Contig 1 (SEQ ID NO: 5)     (301) ATAATGGTTGGGTTGGTAACATGAGAGTYAGGATTATGCTWGCTGGTAAT 351                                                400
Native NVCP (SEQ ID NO: 1)  (351) GCCTTTACTGCGGGGAAGATAATAGTTTCCTGCATACCCCCTGGTTTTGG
sNVCP (SEQ ID NO: 3)        (351) GCCTTTACTGCTGGTAAGATAATAGTTTCTTGCATACCCCCTGGTTTTGG
Contig 1 (SEQ ID NO: 5)     (351) GCCTTTACTGCKGGKAAGATAATAGTTTCYTGCATACCCCCTGGTTTTGG 401                                                450
Native NVCP (SEQ ID NO: 1)  (401) TTCACATAATCTTACTATAGCACAAGCAACTCTCTTTCCACATGTGATTG
sNVCP (SEQ ID NO: 3)        (401) TTCACATAATCTTACTATAGCACAAGCAACTCTCTTTCCTCATGTGATTG
Contig 1 (SEQ ID NO: 5)     (401) TTCACATAATCTTACTATAGCACAAGCAACTCTCTTTCCWCATGTGATTG 451                                                500
Native NVCP (SEQ ID NO: 1)  (451) CTGATGTTAGGACTCTAGACCCCATTGAGGTGCCTTTGGAAGATGTTAGG
sNVCP (SEQ ID NO: 3)        (451) CTGATGTTAGGACTCTTGACCCCATTGAGGTGCCTTTGGAAGATGTTAGG
Contig 1 (SEQ ID NO: 5)     (451) CTGATGTTAGGACTCTWGACCCCATTGAGGTGCCTTTGGAAGATGTTAGG 501                                                550
Native NVCP (SEQ ID NO: 1)  (501) AATGTTCTCTTTCATAATAATGATAGAAATCAACAAACCATGCGCCTTGT
sNVCP (SEQ ID NO: 3)        (501) AATGTTCTCTTTCATAACAACGATAGAAATCAACAAACCATGAGGCTTGT
Contig 1 (SEQ ID NO: 5)     (501) AATGTTCTCTTTCATAAYAAYGATAGAAATCAACAAACCATGMGSCTTGT 551                                                600
Native NVCP (SEQ ID NO: 1)  (551) GTGCATGCTGTACACCCCCCTCCGCACTGGTGGTGGTACTGGTGATTCTT
sNVCP (SEQ ID NO: 3)        (551) GTGCATGCTCTACACCCCCTTGAGGACTGGTGGTGGTACTGGTGATTCTT
Contig 1 (SEQ ID NO: 5)     (551) GTGCATGCTSTACACCCCCYTSMGSACTGGTGGTGGTACTGGTGATTCTT
```

FIGURE 1B

```
                                601                                              650
Native NVCP (SEQ ID NO: 1)  (601) TTGTAGTTGCAGG--GCGAGTTATGACTTGCCCCAGTCCTGATTTTAATT
sNVCP (SEQ ID NO: 3)        (601) TTGTAGTTGCAGGAAG-G-GTTATGACTTGCCCAAGTCCTGATTTTAATT
Contig 1 (SEQ ID NO: 5)     (601) TTGTAGTTGCAGGAAGCGAGTTATGACTTGCCCMAGTCCTGATTTTAATT 651                                              700
Native NVCP (SEQ ID NO: 1)  (651) TCTTGTTTTAGTCCCTCCTACGGTGGAGCAGAAAACCAGGCCCTTCACA
sNVCP (SEQ ID NO: 3)        (651) TCTTGTTTTTAGTCCCTCCTACAGTGGAGCAAAAAACCAGGCCCTTCACA
Contig 1 (SEQ ID NO: 5)     (651) TCTTGTTTTAGTCCCTCCTACRGTGGAGCARAAAACCAGGCCCTTCACA 701                                              750
Native NVCP (SEQ ID NO: 1)  (701) CTCCCAAATCTGCCATTGAGTTCTCTGTCTAACTCACGTGCCCCTCTCCC
sNVCP (SEQ ID NO: 3)        (701) CTCCCAAATCTCCCATTGAGTTCTCTCTCTAACTCAAGAGCCCCTCTCCC
Contig 1 (SEQ ID NO: 5)     (701) CTCCCAAATCTSCCATTGAGTTCTCTSTCTAACTCAMGWGCCCCTCTCCC 751                                              800
Native NVCP (SEQ ID NO: 1)  (751) AATCAGTAGTATCGGCATTTCCCCAGACAATGTCCAGAGTGTGCAGTTCC
sNVCP (SEQ ID NO: 3)        (751) AATTAGTAGTATGGGCATTTCCCCAGACAATGTCCAAAGTGTGCAATTCC
Contig 1 (SEQ ID NO: 5)     (751) AATYAGTAGTATSGGCATTTCCCCAGACAATGTCCARAGTGTGCARTTCC 801                                              850
Native NVCP (SEQ ID NO: 1)  (801) AAAATGGTCGGTGTACTCTGGATGGCCGCCTGGTTGGCACCACCCCAGTT
sNVCP (SEQ ID NO: 3)        (801) AAAATGGTAGGTGTACTCTTGATGGAAGACTTGTTGGCACCACCCCAGTA
Contig 1 (SEQ ID NO: 5)     (801) AAAATGGTMGGTGTACTCTKGATGGMMGMCTKGTTGGCACCACCCCAGTW
```

FIGURE 1C

```
                                   851                                                                         900
Native NVCP (SEQ ID NO: 1) (851) T-CATTGTCACATGTTGCCAAGATAAGAGGGACCTCCAATGGCACTGTAA
sNVCP (SEQ ID NO: 3)       (851) AGC-TTGTCACATGTTGCCAAGATAAGAGAGGTACCTCCAATGGCACTGTGA
Contig 1 (SEQ ID NO: 5)    (851) WGCATTGTCACATGTTGCCAAGATAAGAGGKACCTCCAATGGCACTGTRA 901                                                                         950
Native NVCP (SEQ ID NO: 1) (901) TCAACCTTACTGAATTGGATGGCACACCCTTTCACCCTTTGAGGGCCCT
sNVCP (SEQ ID NO: 3)       (901) TCAACCTTACTGAATTGGATGGCACACCCTTTCACCCTTTGAGGGCCCT
Contig 1 (SEQ ID NO: 5)    (901) TCAACCTTACTGAATTGGATGGCACACCCTTTCACCCTTTGAGGGCCCT 951                                                                        1000
Native NVCP (SEQ ID NO: 1) (951) GCCCCCATTGGGTTTCCAGACCTCGGTTGGTGGTTGTGATTGGCATATCAATAT
sNVCP (SEQ ID NO: 3)       (951) GCCCCCATTGGATTTCCAGATCTTGGTGTTGTGATTGGCATATCAATAT
Contig 1 (SEQ ID NO: 5)    (951) GCCCCCATTGGGRTTTCCAGAYCTYGGTGGTTGTGATTGGCATATCAATAT 1001                                                                        1050
Native NVCP (SEQ ID NO: 1) (1001) GACACAGTTTGGCCATTCTAGCCAGACCCAGTATGATGTAGACACCACC
sNVCP (SEQ ID NO: 3)       (1001) GACACAATTTGGCCATTCTAGCCAAACCCAATATGATGTCGACACCACC
Contig 1 (SEQ ID NO: 5)    (1001) GACACARTTTGGCCATTCTAGCCARACCCARTATGATGTMGACACCACC 1051                                                                        1100
Native NVCP (SEQ ID NO: 1) (1051) CTGACACTTTTGTCCCCCATCTGGTTCAATTCAGGCAAATGGCATTGGC
sNVCP (SEQ ID NO: 3)       (1051) CTGACACTTTTGTCCCCCATCTGGTTCAATTCAAGCAAATGGCATTGGA
Contig 1 (SEQ ID NO: 5)    (1051) CTGACACTTTTGTCCCCCATCTGGTTCAATTCARGCAAATGGCATTGGM 1101                                                                        1150
Native NVCP (SEQ ID NO: 1) (1101) AGTGGTAATTATGTTGGTGTTCTTAGCT-GGATTCCCCCCATCACACC
sNVCP (SEQ ID NO: 3)       (1101) AGTGGTAATTATGTTGGTGTTCTTT-CTTGGATTCCCCCCATCACACC
Contig 1 (SEQ ID NO: 5)    (1101) AGTGGTAATTATGTTGGTGTTCTTWGCTTGGATTCCCCCCATCACACC
```

FIGURE 1D

```
                                   1151                                               1200
Native NVCP (SEQ ID NO: 1)  (1151) CGTCTGGCTCCCAAGTTGACCTTTGGAAGATCCCCAATTATGGGTCAAGT
sNVCP (SEQ ID NO: 3)        (1151) CATCTGGCTCCCAAGTTGACCTTTGGAAGATCCCCAATTATGGATCAAGT
Contig 1 (SEQ ID NO: 5)     (1151) CRTCTGGCTCCCAAGTTGACCTTTGGAAGATCCCCAATTATGGRTCAAGT 1201                                               1250
Native NVCP (SEQ ID NO: 1)  (1201) ATTACGGAGGCAACACATCTAGCCCCTTCTGTATACCCCCCTGGTTTCGG
sNVCP (SEQ ID NO: 3)        (1201) ATTACTGAGGCAACACATCTTGCCCCTTCTGTATACCCCCCTGGTTTTGG
Contig 1 (SEQ ID NO: 5)     (1201) ATTACKGAGGCAACACATCTWGCCCCTTCTGTATACCCCCCTGGTTTYGG 1251                                               1300
Native NVCP (SEQ ID NO: 1)  (1251) AGAGGTATTGGTCTTTTTCATGTCAAAAATGCCAGGTCCTGGTGCTTATA
sNVCP (SEQ ID NO: 3)        (1251) AGAGGTATTGGTCTTTTTCATGTCAAAAATGCCAGGTCCTGGCGCTTATA
Contig 1 (SEQ ID NO: 5)     (1251) AGAGGTATTGGTCTTTTTCATGTCAAAAATGCCAGGTCCTGGYGCTTATA 1301                                               1350
Native NVCP (SEQ ID NO: 1)  (1301) ATTTGCCCTGTCTATTACCACAAGAGTACATTTCACATCTTGCTAGTGAA
sNVCP (SEQ ID NO: 3)        (1301) ATTTGCCATGTCTCTTACCACAAGAGTACATTTCACATCTTGCTAGCGAG
Contig 1 (SEQ ID NO: 5)     (1301) ATTTGCCMTGTCTMTTACCACAAGAGTACATTTCACATCTTGCTAGYGAR 1351                                               1400
Native NVCP (SEQ ID NO: 1)  (1351) CAAGCCCCTACTGTAGGTGAGGCTGCCCTGCTCCACTATGTTGACCCTGA
sNVCP (SEQ ID NO: 3)        (1351) CAAGCCCCTACTGTAGGTGAGGCTGCCCTGCTCCACTATGTTGACCCTGA
Contig 1 (SEQ ID NO: 5)     (1351) CAAGCCCCTACTGTAGGTGAGGCTGCCCTGCTCCACTATGTTGACCCTGA 1401                                               1450
Native NVCP (SEQ ID NO: 1)  (1401) TACCGGTCGGAATCTTGGGGAATTCAAAGCATACCCTGATGGTTTCCTCA
sNVCP (SEQ ID NO: 3)        (1401) TACTGGTAGGAATCTTGGAGAATTCAAAGCATACCCTGATGGTTTCCTCA
Contig 1 (SEQ ID NO: 5)     (1401) TACYGGTMGGAATCTTGGRGAATTCAAAGCATACCCTGATGGTTTCCTCA
```

FIGURE 1E

```
                                    1500
Native NVCP (SEQ ID NO: 1) (1451) CTTGTGTCCCCAATGGGGCTAGCT-CGGGTCCACACAACAGCTGCCGATCAA
sNVCP (SEQ ID NO: 3)       (1451) CTTGTGTCCCCAATGGGGCTAGCT-CGGGTCCACACAACAGCTGCCGATCAA
Contig 1 (SEQ ID NO: 5)    (1451) CTTGTGTCCCCAATGGGGCTAGCTAGCAGCGG-TCCACAACAACTGCCAATCAA
                                                                                                                     CTTGTGTCCCAATGGKGCTAGCWGCGKGCGGGTCCACACARCTGCCRATCAA 1550
Native NVCP (SEQ ID NO: 1) (1501) TGGGGGTCTTTGTCTTTGTTCATGGGTGTCCAGATTTATCAATTAAAGC
sNVCP (SEQ ID NO: 3)       (1501) TGGTGTCTTTGTCTTTGTTCTTTGTTCATGGGTGTCAAGATTTATCAATTAAAGC
Contig 1 (SEQ ID NO: 5)    (1501) TGGKGTCTTTGTCTTTGTCTTTGTTTGTTTCATGGGTGTCMAGATTTATCAATTAAAGC 1600
Native NVCP (SEQ ID NO: 1) (1551) CTGTGGGAACTGCCAGCTCG-GCAAGAGGTAGGCTTGGTCT--GCGCCGA
sNVCP (SEQ ID NO: 3)       (1551) CTGTGGGAACTGCCGCCT-CTAGCGCAAGAGGTAGGCTAGGCTTGGTCTTAG-GAGG-
Contig 1 (SEQ ID NO: 5)    (1551) CTGTGGGAACTGCCWGCTMGGCGCAAGAGGTAGGCTTGGTCTTAGGCMSGA Native NVCP (SEQ ID NO: 1) (1601) TA
sNVCP (SEQ ID NO: 3)       (1601) TA
Contig 1 (SEQ ID NO: 5)    (1601) TA
```

FIGURE 1F

| | | |
|---|---|---|
| Native NVCP (SEQ ID NO: 2) | (1) | MMMASKDATSSVDGAS

```
Native NVCP (SEQ ID NO: 2)  (301) LTELDGTPFHPFEGPAPIGF pNV110
psNV110
T TEV 5' UTR
FIGURE 2B

FLOW CHART FOR NV110-2-4 VACCINE PRODUCTION

*Lycopersicon esculentum* variety "TA234"

↓ Transform with *Agrobacterium tumefaciens* (LBA4404) containing vector psNV110

Individual Transformed Tomato Lines → Screening for Clone Selection (Northern and ELISA for NVCP)

↓ Best individual line clonally propagated (Line sNV110-2)

Clonally Propagated (T0) Master Plant Bank of Line sNV110-2

Clone nodal cuttings in vitro, test periodically by ELISA for NVCP

↓ Transplant to soil
Grow 12-24 weeks (16 hour day length and daily fertilization)

First Generation (T1) Fruit and Seeds → Used in preclinical testing.
Characterization:
- Quantitative ELISA
- Norther blot analysis
- PCR confirmation ↓ Transplant seeds to soil and grow as Recover self-pollinated seed

Second Generation (T2) Fruit and Seeds → Used in preclinical testing.
Characterization:
- Quantitative ELISA
- VLP Sucrose Gradient
- DNA Sequencing ↓ Transplant seeds to soil and grow as above Recover self-pollinated seed

Third Generation (T3) Fruit and Seeds → Characterization:
- Southern blot analysis
- Western blot analysis ↓ Transplant seeds to soil, grow as above; Recover self-pollinated seed

Oral NVCP Transgenic Tomato Vaccine Fourth Generation (T4) Fruit and Seeds Clinical Lot No. NV110-2-4 → Complete Antigen Characterization:
- Quantitative ELISA
- VLP Sucrose Gradient
- Process Documentation

↓

Process, Freeze-dry → Powder → Fill Capsules → Lot NV110-2-4

Process, Freeze-dry → Powder/formulate with Adjuvant → Fill Capsules → Lot NV110-2-4-QS

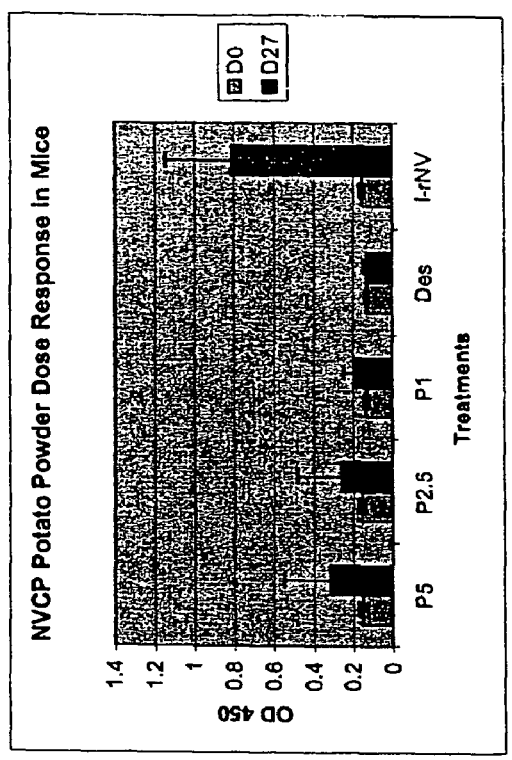
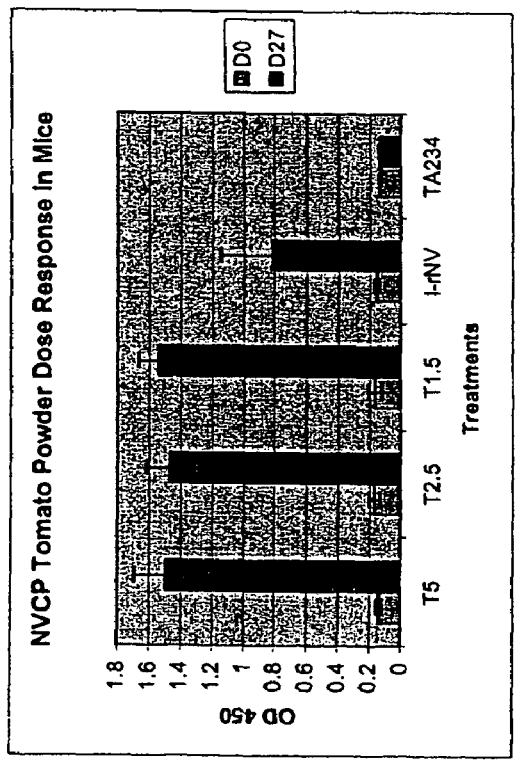
FIGURE 17

A.
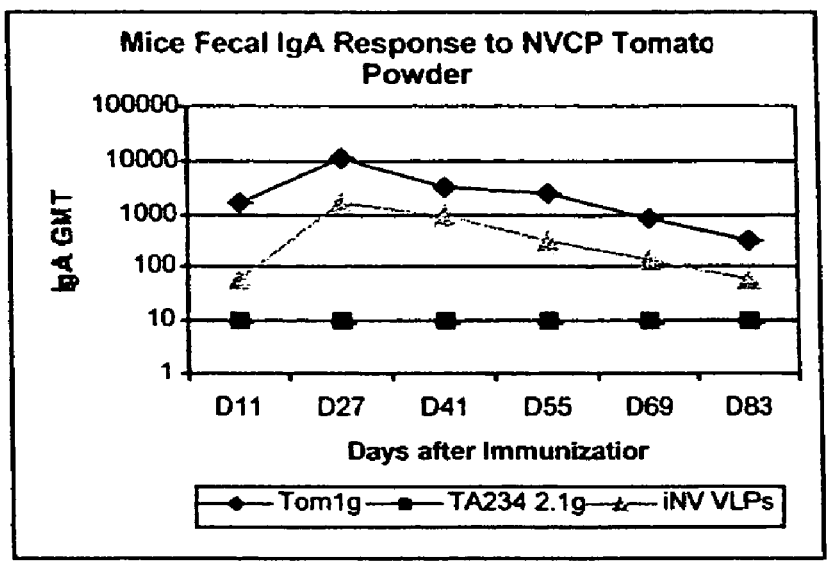
B.
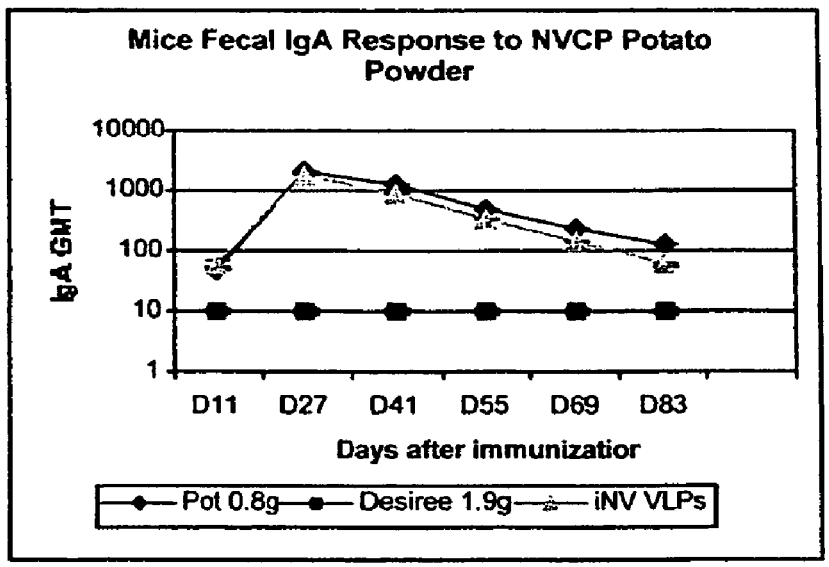
FIGURE 18

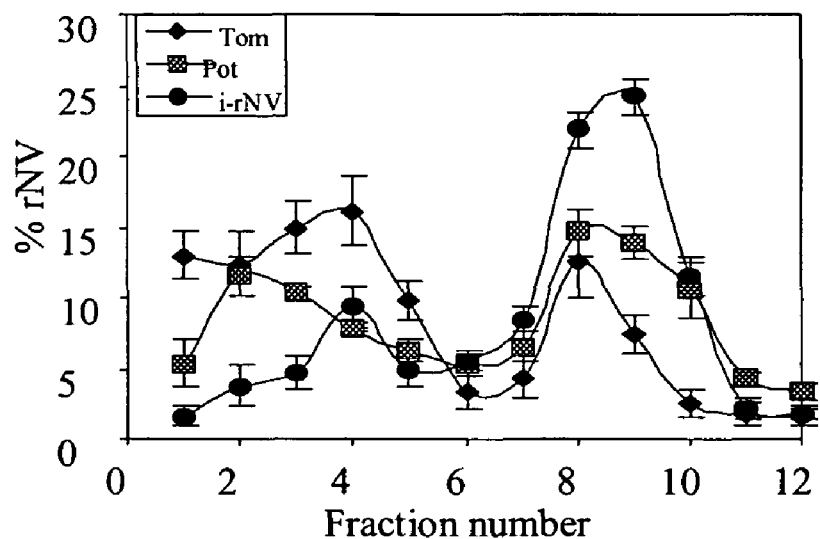
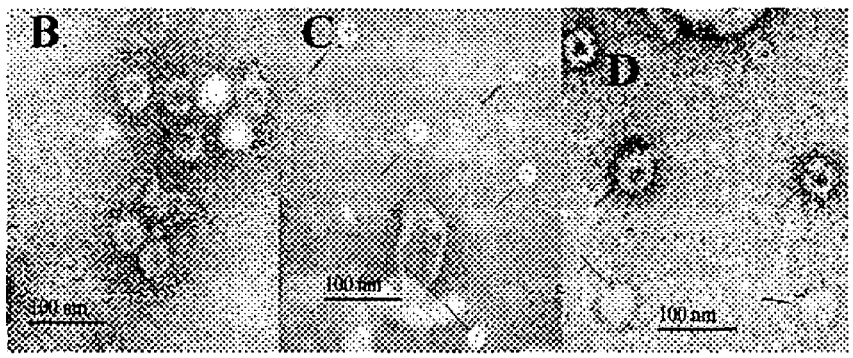
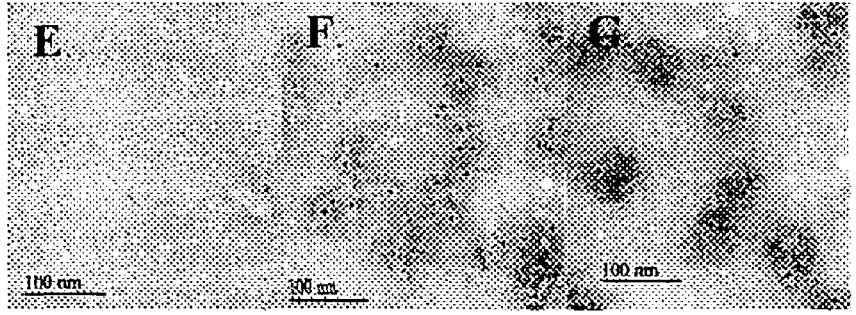
FIGURE 21

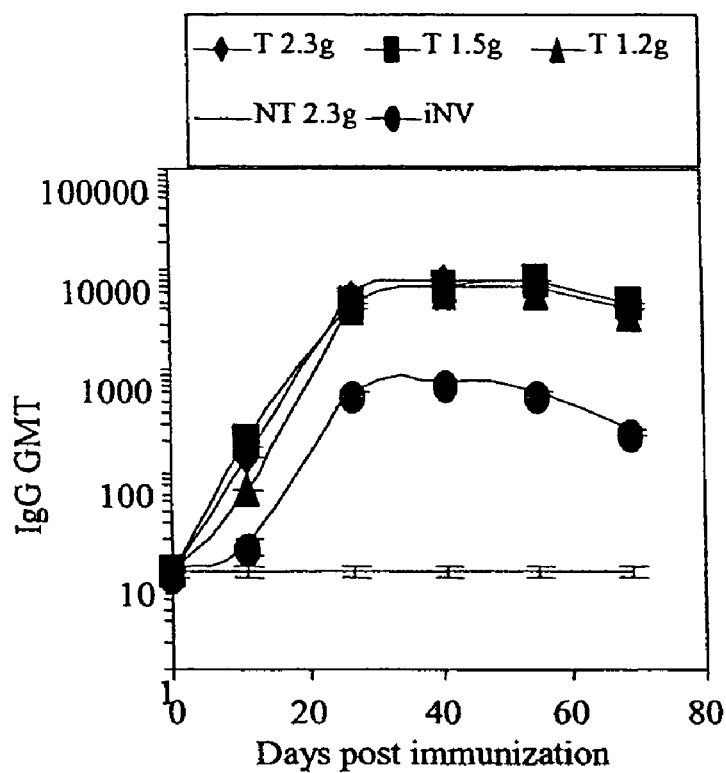
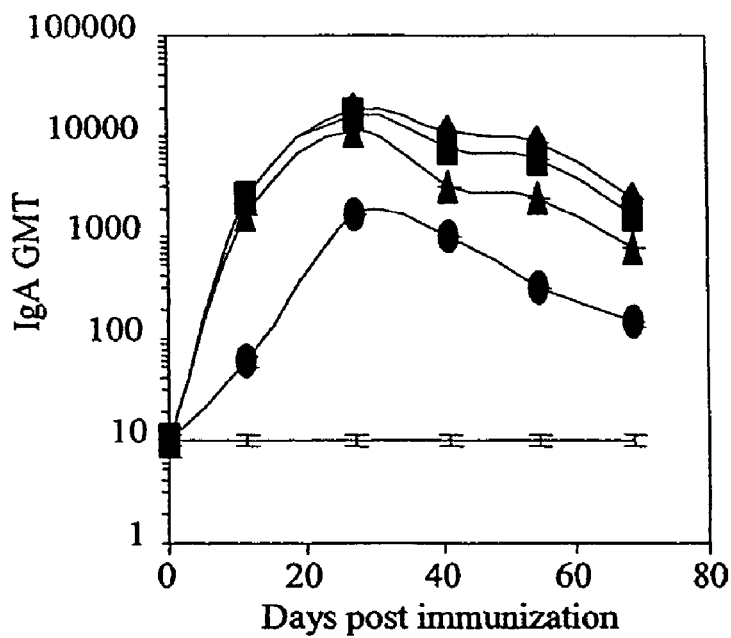
FIGURE 23

VECTORS AND METHODS FOR IMMUNIZATION AGAINST NOROVIRUS USING TRANSGENIC PLANTS

This application claims the benefit of U.S. Provisional Patent Application Ser. No. 60/489,005, filed Jul. 21, 2003.

The subject matter of this application was made with support from the United States Government under National Science Foundation Grant No. BES-0109936. The U.S. Government may have certain rights in this invention.

FIELD OF THE INVENTION

The present invention relates to a synthetic plant-optimized nucleic acid molecule encoding a Norwalk virus capsid protein and uses thereof.

BACKGROUND OF THE INVENTION

Norwalk virus (NV) is classified as a human *calicivirus* (family Caliciviridae, genus *Norovirus*) and is the major cause of acute gastroenteritis in humans. (Jiang et al., "Norwalk Virus Genome Cloning and Characterization," *Science* 250:1580-1583 (1990), Clarke et al., "Organization and Expression of *Calicivirus* Genes," *J Infect Dis* 181(Suppl 2):S309-316 (2000)). "*Norovirus*" was recently approved as the official genus name for the group of viruses provisionally described as "Norwalk-like viruses" (NLV). This group of viruses has also been referred to as *caliciviruses* (because of their virus family name) and as small round structured viruses, or SRSVs (because of their morphologic features).

*Caliciviruses* (family Caliciviridae) infect animals and humans. Within the family Caliciviridae, four genera have been distinguished: *Vesivirus Lagovirus, Norovirus*, and *Sapovirus* (until recently known as Sapporo-like viruses (SLV)(van der Poel et al., "Norwalk-Like *Calicivirus* Genes in Farm Animals," *Emerging Infectious Diseases* 6(1):36-41 (2000); Pringle, C. R., "Virus Taxonomy" *Arch Virol* 143: 1449-1459 (1998)). The genera *Vesivirus* and *Lagovirus* contain a broad range of animal *caliciviruses*, but viruses in the NLV and SLV genera until recently had been found only in humans. Viruses closely related to Norwalk-like viruses have now been found in calves and pigs (van der Poel et al., "Norwalk-Like *Calicivirus* Genes in Farm Animals," *Emerging Infectious Diseases* 6(1):36-41 (2000)), and a murine Norwalk-like virus has been identified (Karst et al., "STAT-1-Dependent Innate Immunity to a Norwalk-Like Virus" *Science* 299:1575-1578 (2003)).

*Noroviruses* are named after the original strain "Norwalk virus," which caused an outbreak of gastroenteritis in a school in Norwalk, Ohio, in 1968. Currently, there are at least four *Norovirus* genogroups (GI, GII, GIII, and GIV), which in turn are divided into approximately 20 genetic clusters. The *caliciviruses* are grouped on the basis of morphology, size, protein profile, and nucleic acid. Norwalk virus and some other human *caliciviruses* share considerable genetic homology.

Recent estimates indicate that NV and NV-like agents are responsible for greater than 90% of outbreaks of acute non-bacterial gastroenteritis in developed and developing countries (Fankhauser et al., "Molecular Epidemiology of "Norwalk-Like Viruses" in Outbreaks of Gastroenteritis in the United States," *J Infect Dis* 178:1571-1578 (1998), Vinje et al., "The Incidence and Genetic Variability of Small Round-Structured Viruses in Outbreaks of Gastroenteritis in The Netherlands," *J Infect Dis* 176:1374-1378 (1997)). Centers for Disease Control in Atlanta attributes about 181,000 cases of gastrointestinal illness in the U.S. each year to NV. Viral gasteroenteritis affects so many individuals that only the common cold is reported more frequently than viral gastroenteritis. Viral transmission is generally by the fecal-oral route. Symptoms of the disease include nausea, vomiting, acute diarrhea, and stomach cramps, with infection most common in adults or older children. The virus has a one to two day incubation period, with a two to three day recovery; however, individuals may still be highly infectious after recovery. Infection with Norwalk virus confers some immunity, which declines over 24 months, allowing re-infection. Epidemic outbreaks of this disease frequently occur on cruise ships, in schools, day care centers, nursing homes, hospitals, and communities. The increasing clinical significance of these infections suggests the pressing need for an efficacious vaccine against Norwalk virus (Estes et al., "Norwalk Virus Vaccines: Challenges and Progress," *J Infect Dis* 181(Suppl 2):S367-373 (2000)). However, to date, it is not cultivatable in vitro, and there are no animal models for study or culturing the virus. The lack of Norwalk virus animal models is apparently related to the fact that humans are the only known host for Norwalk virus.

Norwalk virus is a round, nonenveloped, 27-nm virion. Its nucleic acid contains single-stranded, positive-sense RNA. It has a single structural protein characteristic of a *calicivirus*. The single, positive strand of Norwalk virus RNA contains three open reading frames, the second of which is known to encode a single NV capsid protein (NVCP) that self-assembles into empty virus-like particles (VLPs) lacking viral RNA when expressed in the baculovirus/insect cell expression system (Jiang et al., "Expression, Self-Assembly, and Antigenicity of the Norwalk Virus Capsid Protein," *J Virol* 66:6527-6532 (1992), Jiang et al., "Sequence and Genomic Organization of Norwalk Virus," *Virology* 195:51-61 (1993)) and plant cells (Mason et al., "Expression of Norwalk Virus Capsid Protein in Transgenic Tobacco and Potato and its Oral Immunogenicity in Mice," *Proc Natl Acad Sci USA* 93:5335-5340 (1996)). X-ray crystallography of recombinant NV VLPs (rNV VLPs) showed that these VLPs are composed of 90 dimers of the NVCP that form T=3 icosahedral structure with a diameter of about 38 nm (Prasad et al., "X-ray Crystallographic Structure of the Norwalk Virus Capsid," *Science* 286:287-290 (1999)). The rNV VLPs are stable at low pH, when lyophilized, and when stored long term at 4° C. (Estes et al., "Norwalk Virus Vaccines: Challenges and Progress," *J Infect Dis* 181(Suppl 2):S367-373 (2000)). The insect cell-derived VLPs are immunogenic in experimental animals and in human volunteers following oral administration (Ball et al., "Oral Immunization with Recombinant Norwalk Virus-Like Particles Induces a Systemic and Mucosal Immune Response in Mice," *J Virol* 72:1345-1353 (1998), Ball et al., "Recombinant Norwalk Virus-Like Particles Given Orally to Volunteers: Phase I Study," *Gastroenterology* 117:40-48 (1999)), and in mice when administered parenterally (Jiang et al., "Expression, Self-Assembly, and Antigenicity of the Norwalk Virus Capsid Protein," *J Virol* 66:6527-6532 (1992)), and intranasally (Guerrero et al., "Recombinant Norwalk Virus-Like Particles Administered Intranasally to Mice Induce Systemic and Mucosal (Fecal and Vaginal) Immune Responses.," *J Virol* 75:9713-9722 (2001)). These qualities make the rNV VLPs useful as a candidate for vaccine against *Noroviruses*, including Norwalk virus.

Thus, what is needed now is a strategy which utilizes what has been elucidated about the genetic structure of *Noroviruses* to produce a superior, cost-efficient, effective, and stable vaccine against *Noroviruses*, including Norwalk virus, and a method to produce such a vaccine on a large-scale for distribution and human use world-wide.

The present invention is directed to overcoming these and other deficiencies in the art.

SUMMARY OF THE INVENTION

The present invention relates to a synthetic nucleic acid molecule having a Norwalk virus capsid protein coding sequence, where the nucleic acid molecule is optimized for expression in plants to produce Norwalk virus virus-like particles.

The present invention also relates to a nucleic acid construct having a synthetic plant-optimized nucleic acid molecule encoding a Norwalk virus capsid protein, where the nucleic acid molecule is optimized for expression in plants to produce Norwalk virus virus-like particles. The construct also includes a 5' DNA promoter sequence and a 3' terminator sequence. The promoter and the terminator are operatively coupled to the Norwalk virus capsid protein encoding sequence in the nucleic acid construct to allow expression of the Norwalk virus capsid protein in a plant.

Another aspect of the present invention is a method of producing Norwalk virus capsid protein virus-like particles. This method involves providing a transgenic plant or plant seed transformed with a synthetic plant-optimized nucleic acid molecule encoding a Norwalk virus capsid protein, and growing the transgenic plant or a transgenic plant grown from a plant seed of the transgenic plant under conditions effective to produce Norwalk virus capsid protein virus-like particles.

The present invention also relates to a plant transformed with a nucleic acid construct having a synthetic plant-optimized nucleic acid molecule encoding a Norwalk virus capsid protein, a 5' DNA promoter sequence, and a 3' terminator sequence.

Another aspect of the present is a method of immunizing a subject against disease resulting from infection by a *Norovirus*. This method involves administering the plant transformed with a synthetic plant-optimized nucleic acid molecule encoding a Norwalk virus capsid protein, or a component part or a fruit of the plant, to the subject under conditions effective to immunize the subject against disease resulting from infection by a *Norovirus*.

Another aspect of the present invention is an oral vaccine for immunization of a subject against infection by Norwalk virus. This vaccine is a component of the plant transformed with a synthetic plant-optimized nucleic acid molecule encoding a Norwalk virus capsid protein, where the plant produces Norwalk virus capsid protein virus-like particles for immunization of a subject against infection by Norwalk virus, and a pharmaceutical adjuvant.

The present invention also relates to an expression system, host cells, plants, and plant seeds having a synthetic, plant-optimized nucleic acid molecule encoding for the Norwalk virus capsid protein.

The present invention provides a strategy for biomanufacturing a superior oral vaccine in plants which allows vaccine production and large-scale immunization against Norwalk virus or other *Noroviruses* in a vehicle which would be more acceptable to children than immunizations, and which would be ideal in developing countries. For many vaccines, administration is carried out by injection through the skin with needles. Injection of vaccines using needles carries certain drawbacks including the need for sterile needles and syringes, trained medical personnel to administer the vaccine, discomfort from the injection, and potential complications brought about by puncturing the skin with the needle. Immunization without the use of needles represents a major advance for vaccine delivery by avoiding the aforementioned drawbacks.

BRIEF DESCRIPTION OF THE DRAWINGS

FIGS. 1A-H are comparisons of the nucleotide and corresponding amino acid sequences of native NVCP and a synthetic plant-optimized NVCP (sNVCP) nucleic acid molecule. FIGS. 1A-F show an alignment of the native NVCP nucleotide sequence (SEQ ID NO: 1) and the sNVCP plant-optimized nucleic acid molecule having SEQ ID NO: 3. The contig sequence is shown in FIGS. 1A-F as SEQ ID NO: 5. In FIGS. 1G-H the amino acid sequence of native NVCP (SEQ ID NO: 2) is aligned with the amino acid sequence (SEQ ID NO: 6) encoded by sNVCP (SEQ ID NO: 3). The consensus sequence is shown as SEQ ID NO: 7. The nucleotides that differ between the native and synthetic NVCP sequences are shown in bold.

FIGS. 2A-B are diagrams of the Norwalk virus plasmid constructs used in the present invention. FIG. 2A is a diagram showing psNV110 (plasmid, synthetic) vector construction. Master plasmids pNVCP3 and pPS1 were digested with XbaI and SacI restriction enzymes. Digested fragments were recovered and ligated to form the psNV110 transformation vector. psNV110 was cloned into *E. coli* DH5α and screened by PCR before transformation. FIG. 2B shows the plasmids used for expression of recombinant Norwalk Virus Capsid Protein (rNV) in plants. Each plasmid contains the double-enhancer cauliflower mosaic virus (CaMV) 35S promoter (2×35S); tobacco etch virus 5' untranslated region (TEV 5'-UTR); soybean vegetative storage protein gene vspB 3' element (VSP3'); and an nptII expression cassette (kanamycin resistance) for selection of plant transformants using kanamycin. NV110 includes the native viral NVCP gene and sNV110 includes the plant-optimized NVCP gene.

FIG. 5 is a flow diagram showing the process of vaccine production from initiation of plant transformation to harvest of fruit for vaccine administration.

FIG. 7A shows a Coomassie blue stained gel demonstrating the molecular weight markers which correlate to the Southern blot membrane in FIG. 7B. The two images are aligned to show the size of the probed fragments derived from sNV110-2 genomic DNA cut with restriction enzymes XbaI or XhoI T-DNA internal primers sNV-forward and sNV-reverse were used to create the probe according to PCR DIG Probe Synthesis Kit (Roche Diagnostics, Indianapolis, Ind.) protocol. The positive control is the sNV plasmid psNV110 cut with XbaI. The results confirm integration of the vector as sNV-2 DNA contains an internal fragment of the sNVCP gene.

FIG. 10 is a graph showing ELISA analysis of NVCP expression in tomato fruit from 10 different transgenic lines, transformed with a synthetic (plant-optimized) gene, or the native viral gene. Plant-optimization of the coding sequence was shown to increase antigen expression in this instance by 2-3 fold, with an average expression level of 50 ng NV rNV/μg TSP. (CT-control tomato showed no detectable levels of NVCP).

FI was extracted from potato tubers and blotted as in A.

FIGS. 21A-G show that the rNV VLPs were assembled in tomato and potato as shown in sucrose gradient sedimentation and electron microscopy. FIG. 21A: crude extracts (1 ml) from tomato fruit and potato tubers were sedimented in sucrose gradients (1-50%). The proportion of each fraction that cosedimented with i-rNV (control reference antigen) was calculated on the basis of total ELISA or immunoblotting-positive materials. The profiles were obtained from at least 10 replications. Fraction 1 is the top of the gradient. VLPs of 38 nm were pooled in fractions 8-10. Particles of two sizes, 23 nm, shown in FIG. 21C, and 38 nm, shown in FIG. 21D, from tomato fruit are visualized (arrows) by negative staining and electron microscopy. The 22-nm particles existed in fractions 3-5 in sucrose gradients. Control iNV VLPs (38 nm) are shown in FIG. 21B. FIGS. 21E-G: tomato fruit-derived particles from fraction 3-5, shown in FIGS. 21F, and 8-10, shown in FIG. 21G, were pooled separately and confirmed with immune electron microscopy by using pre-absorbed antibodies. Particles were clumped by antibodies. Negative control of nontransgenic fruit is shown in FIG. 21E.

FIG. 22A is a graph showing the kinetics of serum, and FIG. 22B, that of intestinal, antibody responses in mice orally immunized with rNV transgenic potato, as measured by ELISA. Five mice in each group ingested 1 g potato powder without water, or either 1.2 or 2 g potato powder with 0.6 volume of water on days 1, 4, 17, and 20. One group was each gavaged with 100 g iNV VLPs (control). Nontransgenic potato powder was fed in a negative control group. Nonresponders were included in the calculations of the GMTs (geometric mean antibody titers). Standard errors were calculated on the log-transformed titers. Statistical analysis was done with the Mann-Whitney U test. Only 20-40% of immunized mice showed immune responses in groups ingesting 1.2 g and 2 g potato powder respectively. VLPs disassembled after potato powder was mixed with $H_2O$, as shown in FIGS. 22C-D, as analyzed by sucrose gradient followed by western blotting. The portion of rNV VLPs was significant in the potato powder that was freeze-dried and stored at room temperature, as shown in FIG. 22C; however, this decreased when mixed with $H_2O$, as shown in FIG. 22D. Numbers above lanes indicated the gradient fraction, with fraction 1 at the top. "De," extract of nontransgenic control 'Desiree' potato powder.

FIGS. 23A-B show the immunologic response of mice to rNV-transgenic tomato. FIG. 23A shows the kinetics of serum, and FIG. 23B shows the kinetics of intestinal antibody responses in mice orally immunized with rNV-transgenic tomato, as measured by ELISA. Five mice in each group ingested 1.2 g, 1.5 g or 2.3 g of tomato powder mixed with 0.6 volume of water, on days 1, 4, 17, and 20. One group was gavaged with 100 g iNV VLPs each. Nontransgenic tomato powder was fed to a negative control group. All mice ingesting 1.2 g or more consistently had significantly higher IgG and IgA GMTs than those gavaged with 100 g iNV VLPs (control reference antigen)($p<0.05$, Mann-Whitney test). Standard errors were calculated on the log-transformed titers.

FIGS. 24A-C show the serum IgG responses, and FIGS. 24D-F show the intestinal IgA responses of mice to different doses of rNV-transgenic tomato freeze-dried powder or air-dried fruit at 11, 27, and 41 days post immunization (dpi). All panels share the same horizontal axis, showing different doses, feeding times and diet forms (F, freeze-dried powder; A, air-dried fruit). Tomato powder or air-dried fruit (0.1, 0.4, and 0.8 g) was fed on days 1, 4, 17, and 20. Alternative immunization schedules were 2 feedings of 0.8 g tomato powder or air-dried fruit on days 1 and 20, or 3 feedings of 0.8 g powder on days 1, 4, and 20. NT, nontransgenic tomato TA234. A mouse was considered to be a non-responder if its post-immunization titer failed to increase by 4-fold or greater in comparison with a preimmunization GMT of 10. GMTs were calculated including non-responders. The number of responders per treatment is indicated as a fraction of the 5 animals per group, with the GMTs for the responders only indicated in parenthesis. Above each column is the number of responders over the total number of mice tested, and GMTs of the only responders is shown in parentheses. For each panel, identical symbols above two different columns indicate that these two groups were significantly different ($p<0.05$, Mann-Whitney test). Standard errors were calculated on the log-transformed titers.

FIG. 25A shows serum IgG in response to potato, and FIG. 25C shows serum IgG in response to tomato. FIG. 25B shows intestinal IgA response to potato and FIG. 25D shows intestinal IgA response to tomato. Mice were orally immunized on days 1, 4, 17, and 20, as shown in FIGS. 22, 23, and 24. As serum and fecal antibody titers began to approach baselines values, a gavage of 100 µg iNV VLPs was administered to each group at the day indicated on the x-axis. Rapid and robust immune responses were observed. One exception was the group that ingested 1.2 g tomato powder. Serum IgG antibody was long-lived with GMT exceeding 2000 in 6 month post immunization. For this group, a single booster resulted in an IgG GMT exceeding 22,000 and IgA GM exceeding 13,000. Groups are illustrated by the markers in the legend on each figure. T=tomato; P=potato; iNV=control (reference antigen); NP=nontransgenic potato; NT=nontransgenic tomato TA234. Standard errors were calculated on the log-transformed titers.

DETAILED DESCRIPTION OF THE INVENTION

Figure 2A:
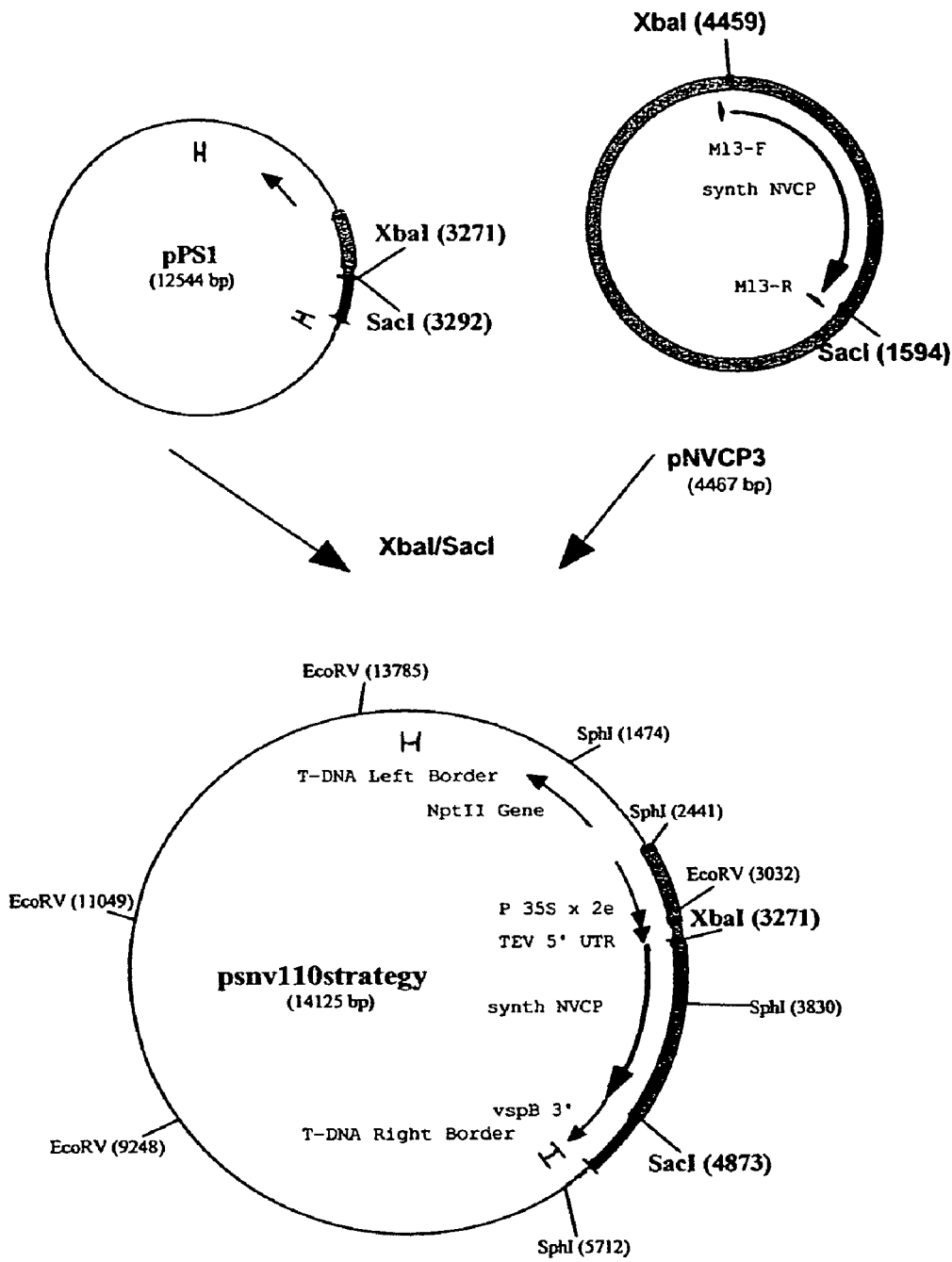

The present invention relates to a synthetic nucleic acid molecule having a Norwalk virus capsid protein coding sequence, where the nucleic acid molecule is optimized for expression in plants to produce Norwalk virus virus-like particles.

As used herein, "Norwalk virus capsid protein coding sequence" refers to the second open reading frame (ORF-2) of the nucleic acid sequence which codes for the native Norwalk virus capsid protein, and includes homologs from Norwalk-like viruses within the *Norovirus* genus. This nucleic acid in the native Norwalk virus has a nucleotide sequence of SEQ ID NO: 1, as follows:

| | | | | | | |
|---|---|---|---|---|---|---|
| ATGATGATGG | CGTCTAAGGA | CGCTACATCA | AGCGTGGATG | GCGCTAGTGG | CGCTGGTCAG | 60 |
| TTGGTACCGG | AGGTTAATGC | TTCTGACCCT | CTTGCAATGG | ATCCTGTAGC | AGGTTCTTCG | 120 |
| ACAGCAGTCG | CGACTGCTGG | ACAAGTTAAT | CCTATTGATC | CCTGGAIAAT | TAATAATTTT | 180 |
| GTGCAAGCCC | CCCAAGGTGA | ATTTACTATT | TCCCCAAATA | ATACCCCCGG | TGATGTTTTG | 240 |

-continued

```
TTTGATTTGA GTTTGGGTCC CCATCTTAAT CCTTTCTTGC TCCATCTATC ACAAATGTAT    300
AATGGTTGGG TTGGTAACAT GAGAGTCAGG ATTATGCTAG CTGGTAATGC CTTTACTGCG    360
GGGAAGATAA TAGTTTCCTG CATACCCCCT GGTTTTGGTT CACATAATCT TACTATAGCA    420
CAAGCAACTC TCTTTCCACA TGTGATTGCT GATGTTAGGA CTCTAGACCC CATTGAGGTG    480
CCTTTGGAAG ATGTTAGGAA TGTTCTCTTT CATAATAATG ATAGAAATCA ACAAACCATG    540
CGCCTTGTGT GCATGCTGTA CACCCCCCTC CGCACTGGTG GTGGTACTGG TGATTCTTTT    600
GTAGTTGCAG GGCGAGTTAT GACTTGCCCC AGTCCTGATT TTAATTTCTT GTTTTTAGTC    660
CCTCCTACGG TGGAGCAGAA AACCAGGCCC TTCACACTCC CAAATCTGCC ATTGAGTTCT    720
CTGTCTAACT CACGTGCCCC TCTCCCAATC AGTAGTATCG GCATTTCCCC AGACAATGTC    780
CAGAGTGTGC AGTTCCAAAA TGGTCGGTGT ACTCTGGATG GCCGCCTGGT TGGCACCACC    840
CCAGTTTCAT TGTCACATGT TGCCAAGATA AGAGGGACCT CCAATGGCAC TGTAATCAAC    900
CTTACTGAAT TGGATGGCAC ACCCTTTCAC CCTTTTGAGG GCCCTGCCCC CATTGGGTTT    960
CCAGACCTCG GTGGTTGTGA TTGGCATATC AATATGACAC AGTTTGGCCA TTCTAGCCAG   1020
ACCCAGTATG ATGTAGACAC CACCCCTGAC ACTTTTGTCC CCCATCTTGG TTCAATTCAG   1080
GCAAATGGCA TTGGCAGTGG TAATTATGTT GGTGTTCTTA GCTGGATTTC CCCCCCATCA   1140
CACCCGTCTG GCTCCCAAGT TGACCTTTGG AAGATCCCCA ATTATGGGTC AAGTATTACG   1200
GAGGCAACAC ATCTAGCCCC TTCTGTATAC CCCCCTGGTT TCGGAGAGGT ATTGGTCTTT   1260
TTCATGTCAA AAATGCCAGG TCCTGGTGCT TATAATTTGC CCTGTCTATT ACCACAAGAG   1320
TACATTTCAC ATCTTGCTAG TGAACAAGCC CCTACTGTAG GTGAGGCTGC CCTGCTCCAC   1380
TATGTTGACC CTGATACCGG TCGGAATCTT GGGGAATTCA AAGCATACCC TGATGGTTTC   1440
CTCACTTGTG TCCCCAATGG GGCTAGCTCG GGTCCACAAC AGCTGCCGAT CAATGGGGTC   1500
TTTGTCTTTG TTTCATGGGT GTCCAGATTT TATCAATTAA AGCCTGTGGG AACTGCCAGC   1560
TCGGCAAGAG GTAGGCTTGG TCTGCGCCGA TAA                                1593
```

The native Norwalk virus coding nucleic acid molecule has 1,593 base pairs, and encodes an amino acid having SEQ ID NO: 2, matching Genbank accession number M87661 (genome for Norwalk Virus, ORFs 1-3) or AAB50466 (which are hereby incorporated by reference in their entirety) (specifically for the NV capsid protein) as follows:

```
Met Met Met Ala Ser Lys Asp Ala Thr Ser Ser Val Asp Gly Ala Ser
 1               5                  10                  15
Gly Ala Gly Gln Leu Val Pro Glu Val Asn Ala Ser Asp Pro Leu Ala
            20                  25                  30
Met Asp Pro Val Ala Gly Ser Ser Thr Ala Val Ala Thr Ala Gly Gln
        35                  40                  45
Val Asn Pro Ile Asp Pro Trp Ile Ile Asn Asn Phe Val Gln Ala Pro
    50                  55                  60
Gln Gly Glu Phe Thr Ile Ser Pro Asn Asn Thr Pro Gly Asp Val Leu
65                  70                  75                  80
Phe Asp Leu Ser Leu Gly Pro His Leu Asn Pro Phe Leu Leu His Leu
                85                  90                  95
Ser Gln Met Tyr Asn Gly Trp Val Gly Asn Met Arg Val Arg Ile Met
            100                 105                 110
Leu Ala Gly Asn Ala Phe Thr Ala Gly Lys Ile Ile Val Ser Cys Ile
        115                 120                 125
Pro Pro Gly Phe Gly Ser His Asn Leu Thr Ile Ala Gln Ala Thr Leu
    130                 135                 140
Phe Pro His Val Ile Ala Asp Val Arg Thr Leu Asp Pro Ile Glu Val
145                 150                 155                 160
Pro Leu Glu Asp Val Arg Asn Val Leu Phe His Asn Asn Asp Arg Asn
                165                 170                 175
Gln Gln Thr Met Arg Leu Val Cys Met Leu Tyr Thr Pro Leu Arg Thr
            180                 185                 190
```

-continued

```
Gly Gly Gly Thr Gly Asp Ser Phe Val Val Ala Gly Arg Val Met Thr
        195                 200                 205
Cys Pro Ser Pro Asp Phe Asn Phe Leu Phe Leu Val Pro Pro Thr Val
    210                 215                 220
Glu Gln Lys Thr Arg Pro Phe Thr Leu Pro Asn Leu Pro Leu Ser Ser
225                 230                 235                 240
Leu Ser Asn Ser Arg Ala Pro Leu Pro Ile Ser Ser Ile Gly Ile Ser
                245                 250                 255
Pro Asp Asn Val Gln Ser Val Gln Phe Gln Asn Gly Arg Cys Thr Leu
            260                 265                 270
Asp Gly Arg Leu Val Gly Thr Thr Pro Val Ser Leu Ser His Val Ala
        275                 280                 285
Lys Ile Arg Gly Thr Ser Asn Gly Thr Val Ile Asn Leu Thr Glu Leu
    290                 295                 300
Asp Gly Thr Pro Phe His Pro Phe Glu Gly Pro Ala Pro Ile Gly Phe
305                 310                 315                 320
Pro Asp Leu Gly Gly Cys Asp Trp His Ile Asn Met Thr Gln Phe Gly
                325                 330                 335
His Ser Ser Gln Thr Gln Tyr Asp Val Asp Thr Thr Pro Asp Thr Phe
            340                 345                 350
Val Pro His Leu Gly Ser Ile Gln Ala Asn Gly Ile Gly Ser Gly Asn
        355                 360                 365
Tyr Val Gly Val Leu Ser Trp Ile Ser Pro Pro Ser His Pro Ser Gly
    370                 375                 380
Ser Gln Val Asp Leu Trp Lys Ile Pro Asn Tyr Gly Ser Ser Ile Thr
385                 390                 395                 400
Glu Ala Thr His Leu Ala Pro Ser Val Tyr Pro Pro Gly Phe Gly Glu
                405                 410                 415
Val Leu Val Phe Phe Met Ser Lys Met Pro Gly Pro Gly Ala Tyr Asn
            420                 425                 430
Leu Pro Cys Leu Leu Pro Gln Glu Tyr Ile Ser His Leu Ala Ser Glu
        435                 440                 445
Gln Ala Pro Thr Val Gly Glu Ala Ala Leu Leu His Tyr Val Asp Pro
    450                 455                 460
Asp Thr Gly Arg Asn Leu Gly Glu Phe Lys Ala Tyr Pro Asp Gly Phe
465                 470                 475                 480
Leu Thr Cys Val Pro Asn Gly Ala Ser Ser Gly Pro Gln Gln Leu Pro
                485                 490                 495
Ile Asn Gly Val Phe Val Phe Val Ser Trp Val Ser Arg Phe Tyr Gln
            500                 505                 510
Leu Lys Pro Val Gly Thr Ala Ser Ser Ala Arg Gly Arg Leu Gly Leu
        515                 520                 525
Arg Arg
530
```

The plant-optimized NVCP nucleic acid molecules (sN-VCPs) of the present invention are synthetic variants of the native NVCP gene. They were designed using the native NVCP nucleotide sequence shown above, in addition to similar sequences provided under Genbank accession numbers AB031013 and L23828 (which are hereby incorporated by reference in their entirety). The coding sequence was modified to replace viral-optimized codons with codons preferable for use in plants. The sNVCPs of the present invention were prepared by altering 108 of 1584 nucleotides in native NVCP gene (approximately 14% of the codons) to plant-favored codons, and removing 26 'CG' and 8 'CC' dinucleotides. By "removing" it is meant that in several positions where 'CG' and 'CC' occur in the native sequence at least one of the dinucleotides was eliminated from sequence. In this way, the native NVCP gene was "plant-optimized," to allow a viral derived nucleic acid molecule to be optimally expressed in plants. The Genbank references for NVCP coding sequence have alternative codons specified at the 759 base pair (either ATG or ATC), which result in sequence coding for either an Isoleucine or Methionine at the 253 amino acid residue. Either residue is suitable as a plant-optimized sequence of the present invention.

One plant-optimized NVCP nucleic acid molecule of the present invention has a nucleotide sequence of SEQ ID NO: 3 as follows:

```
ATGATGATGG CTTCTAAGGA TGCTACATCA TCTGTGGATG GAGCTAGTGG AGCTGGTCAA    60

TTGGTTCCAG AGGTTAATGC TTCTGACCCT CTTGCTATGG ATCCTGTAGC AGGTTCTTCC   120

ACAGCAGTTG CTACTGCTGG ACAAGTTAAT CCTATTGATC CATGGATAAT TAACAACTTT   180

GTGCAAGCCC CCCAAGGTGA ATTCACTATT TCCCCAAACA ACACCCCAGG TGATGTTTTG   240

TTTGATTTGA GTTTGGGTCC CCATCTTAAT CCTTTCTTGC TCCATCTCTC ACAAATGTAT   300

AATGGTTGGG TTGGTAACAT GAGAGTTAGG ATTATGCTTG CTGGTAATGC CTTTACTGCT   360

GGTAAGATAA TAGTTTCTTG CATACCCCCT GGTTTTGGTT CACATAATCT TACTATAGGA   420
```

```
                                       -continued
CAAGCAACTC  TCTTTCCTCA  TGTGATTGCT  GATGTTAGGA  CTCTTGACCC  CATTGAGGTG    480

CCTTTGGAAG  ATGTTAGGAA  TGTTCTCTTT  CATAACAACG  ATAGAAATCA  ACAAACCATG    540

AGGCTTGTGT  GCATGCTCTA  CACCCCCTTG  AGGACTGGTG  GTGGTACTGG  TGATTCTTTT    600

GTAGTTGCAG  GAAGGGTTAT  GACTTGCCCA  AGTCCTGATT  TTAATTTCTT  GTTTTTAGTC    660

CCTCCTACAG  TGGAGCAAAA  AACCAGGCCC  TTCACACTCC  CAAATCTCCC  ATTGAGTTCT    720

CTCTCTAACT  CAAGAGCCCC  TCTCCCAATT  AGTAGTATGG  GCATTTCCCC  AGACAATGTC    780

CAAAGTGTGC  AATTCCAAAA  TGGTAGGTGT  ACTCTTGATG  GAAGACTTGT  TGGCACCACC    840

CCAGTAAGCT  TGTCACATGT  TGCCAAGATA  AGAGGTACCT  CCAATGGCAC  TGTGATCAAC    900

CTTACTGAAT  TGGATGGCAC  ACCCTTTCAC  CCTTTTGAGG  GCCCTGCCCC  CATTGGATTT    960

CCAGATCTTG  GTGGTTGTGA  TTGGCATATC  AATATGACAC  AATTTGGCCA  TTCTAGCCAA   1020

ACCCAATATG  ATGTCGACAC  CACCCCTGAC  ACTTTTGTCC  CCCATCTTGG  TTCAATTCAA   1080

GCAAATGGCA  TTGGAAGTGG  TAATTATGTT  GGTGTTCTTT  CTTGGATTTC  CCCCCCATCA   1140

CACCCATCTG  GCTCCCAAGT  TGACCTTTGG  AAGATCCCCA  ATTATGGATC  AAGTATTACT   1200

GAGGCAACAC  ATCTTGCCCC  TTCTGTATAC  CCCCCTGGTT  TTGGAGAGGT  ATTGGTCTTT   1260

TTCATGTCAA  AAATGCCAGG  TCCTGGCGCT  TATAATTTGC  CATGTCTCTT  ACCACAAGAG   1320

TACATTTCAC  ATCTTGCTAG  CGAGCAAGCC  CCTACTGTAG  GTGAGGCTGC  CCTGCTCCAC   1380

TATGTTGACC  CTGATACTGG  TAGGAATCTT  GGAGAATTCA  AAGCATACCC  TGATGGTTTC   1440

CTCACTTGTG  TCCCCAATGG  TGCTAGCAGC  GGTCCACAAC  AACTGCCAAT  CAATGGTGTC   1500

TTTGTCTTTG  TTTCATGGGT  GTCAAGATTT  TATCAATTAA  AGCCTGTGGG  AACTGCCTCT   1560

AGCGCAAGAG  GTAGGCTTGG  TCTTAGGAGG  TAA                                  1593
```

The nucleic acid molecule corresponding to SEQ ID NO: 3 encodes a Norwalk virus capsid protein having SEQ ID NO: 6, as follows:

```
Met Met Met Ala Ser Lys Asp Ala Thr Ser Ser Val Asp Gly Ala Ser
 1               5                  10                  15
Gly Ala Gly Gln Leu Val Pro Glu Val Asn Ala Ser Asp Pro Leu Ala
                20                  25                  30
Met Asp Pro Val Ala Gly Ser Ser Thr Ala Val Ala Thr Ala Gly Gln
            35                  40                  45
Val Asn Pro Ile Asp Pro Trp Ile Ile Asn Asn Phe Val Gln Ala Pro
     50                  55                  60
Gln Gly Glu Phe Thr Ile Ser Pro Asn Asn Thr Pro Gly Asp Val Leu
 65                  70                  75                  80
Phe Asp Leu Ser Leu Gly Pro His Leu Asn Pro Phe Leu Leu His Leu
                85                  90                  95
Ser Gln Met Tyr Asn Gly Trp Val Gly Asn Met Arg Val Arg Ile Met
               100                 105                 110
Leu Ala Gly Asn Ala Phe Thr Ala Gly Lys Ile Ile Val Ser Cys Ile
            115                 120                 125
Pro Pro Gly Phe Gly Ser His Asn Leu Thr Ile Ala Gln Ala Thr Leu
        130                 135                 140
Phe Pro His Val Ile Ala Asp Val Arg Thr Leu Asp Pro Ile Glu Val
145                 150                 155                 160
Pro Leu Glu Asp Val Arg Asn Val Leu Phe His Asn Asn Asp Arg Asn
                165                 170                 175
Gln Gln Thr Met Arg Leu Val Cys Met Leu Tyr Thr Pro Leu Arg Thr
            180                 185                 190
Gly Gly Gly Thr Gly Asp Ser Phe Val Val Ala Gly Arg Val Met Thr
        195                 200                 205
Cys Pro Ser Pro Asp Phe Asn Phe Leu Phe Leu Val Pro Pro Thr Val
    210                 215                 220
Glu Gln Lys Thr Arg Pro Phe Thr Leu Pro Asn Leu Pro Leu Ser Ser
225                 230                 235                 240
Leu Ser Asn Ser Arg Ala Pro Leu Pro Ile Ser Ser Ile Gly Ile Ser
                245                 250                 255
```

-continued

```
Pro Asp Asn Val Gln Ser Val Gln Phe Gln Asn Gly Arg Cys Thr Leu
            260                 265                 270
Asp Gly Arg Leu Val Gly Thr Thr Pro Val Ser Leu Ser His Val Ala
        275                 280                 285
Lys Ile Arg Gly Thr Ser Asn Gly Thr Val Ile Asn Leu Thr Glu Leu
        290                 295                 300
Asp Gly Thr Pro Phe His Pro Phe Glu Gly Pro Ala Pro Ile Gly Phe
305                 310                 315                 320
Pro Asp Leu Gly Gly Cys Asp Trp His Ile Asn Met Thr Gln Phe Gly
                325                 330                 335
His Ser Ser Gln Thr Gln Tyr Asp Val Asp Thr Thr Pro Asp Thr Phe
            340                 345                 350
Val Pro His Leu Gly Ser Ile Gln Ala Asn Gly Ile Gly Ser Gly Asn
        355                 360                 365
Tyr Val Gly Val Leu Ser Trp Ile Ser Pro Pro Ser His Pro Ser Gly
    370                 375                 380
Ser Gln Val Asp Leu Trp Lys Ile Pro Asn Tyr Gly Ser Ser Ile Thr
385                 390                 395                 400
Glu Ala Thr His Leu Ala Pro Ser Val Tyr Pro Pro Gly Phe Gly Glu
                405                 410                 415
Val Leu Val Phe Phe Met Ser Lys Met Pro Gly Pro Gly Ala Tyr Asn
            420                 425                 430
Leu Pro Cys Leu Leu Pro Gln Glu Tyr Ile Ser His Leu Ala Ser Glu
        435                 440                 445
Gln Ala Pro Thr Val Gly Glu Ala Ala Leu Leu His Tyr Val Asp Pro
    450                 455                 460
Asp Thr Gly Arg Asn Leu Gly Glu Phe Lys Ala Tyr Pro Asp Gly Phe
465                 470                 475                 480
Leu Thr Cys Val Pro Asn Gly Ala Ser Ser Gly Pro Gln Gln Leu Pro
                485                 490                 495
Ile Asn Gly Val Phe Val Phe Val Ser Trp Val Ser Arg Phe Tyr Gln
            500                 505                 510
Leu Lys Pro Val Gly Thr Ala Ser Ser Ala Arg Gly Arg Leu Gly Leu
        515                 520                 525
Arg Arg
530
```

The sNVCP having SEQ ID NO: 6 has 99.8% homology to the native NVCP amino acid. In particular, the amino acid coded by SEQ ID NO: 3 varies from the native NVCP amino acid in having a mutation of Ile to Met at amino acid position 253. This mutation is due to a C-G transversion creating a "ATC" to "ATG" mutation at nucleotides 756-759 in the plant-optimized sNVCP sequence having SEQ ID NO: 3. The "ATG" and "ATC" are shown above bold and underlined in SEQ ID NO: 3 and in SEQ ID NO: 4, below, respectively.

A second plant-optimized nucleic acid molecule of the present invention has a nucleotide sequence of SEQ ID NO: 4, as follows:

```
ATGATGATGG CTTCTAAGGA TGCTACATCA TCTGTGGATG GAGCTAGTGG AGCTGGTCAA    60
TTGGTTCCAG AGGTTAATGC TTCTGACCCT CTTGCTATGG ATCCTGTAGC AGGTTCTTCC   120
ACAGCAGTTG CTACTGCTGG ACAAGTTAAT CCTAITGATC CATGGATAAT TAACAACTTT   180
GTGCAAGCCC CCCAAGGTGA ATTCACTATT TCCCCAAACA ACACCCCAGG TGATGTTTTG   240
TTTGATTTGA GTTTGGGTCC CCATCTTAAT CCTTTCTTGC TCCATCTCTC ACAAATGTAT   300
AATGGTTGGG TTGGTAACAT GAGAGTTAGG ATTATGCTTG CTGGTAATGC CTTTACTGCT   360
GGTAAGATAA TAGTTTCTTG CATACCCCCT GGTTTTGGTT CACATAATCT TACTATAGCA   420
CAAGCAACTC TCTTTCCTCA TGTGATTGCT GATGTTAGGA CTCTTGACCC CATTGAGGTG   480
CCTTTGGAAG ATGTTAGGAA TGTTCTCTTT CATAACAACG ATAGAAATCA ACAAACCATG   540
AGGCTTGTGT GCATGCTCTA CACCCCCTTG AGGACTGGTG GTGGTACTGG TGATTCTTTT   600
GTAGTTGCAG GAAGGGTTAT GACTTGCCCA AGTCCTGATT TTAATTTCTT GTTTTTAGTC   660
CCTCCTACAG TGGAGCAAAA AACCAGGCCC TTCACACTCC CAAATCTCCC ATTGAGTTCT   720
CTCTCTAACT CAAGAGCCCC TCTCCCAATT AGTAGTATCG GCATTTCCCC AGACAATGTC   780
CAAAGTGTGC AATTCCAAAA TGGTAGGTGT ACTCTTGATG GAAGACTTGT TGGCACCACC   840
CCAGTAAGCT TGTCACATGT TGCCAAGATA AGAGGTACCT CCAATGGCAC TGTGATCAAC   900
CTTACTGAAT TGGATGGCAC ACCCTTTCAC CCTTTTGAGG GCCCTGCCCC CATTGGATTT   960
```

-continued

```
CCAGATCTTG  GTGGTTGTGA  TTGGCATATC  AATATGACAC  AATTTGGCCA  TTCTAGCCAA  1020

ACCCAATATG  ATGTCGACAC  CACCCCTGAC  ACTTTTGTCC  CCCATCTTGG  TTCAATTCAA  1080

GCAAATGGCA  TTGGAAGTGG  TAATTATGTT  GGTGTTCTTT  CTTGGATTTC  CCCCCCATCA  1140

CACCCATCTG  GCTCCCAAGT  TGACCTTTGG  AAGATCCCCA  ATTATGGATC  AAGTATTACT  1200

GAGGCAACAC  ATCTTGCCCC  TTCTGTATAC  CCCCCTGGTT  TTGGAGAGGT  ATTGGTCTTT  1260

TTCATGTCAA  AAATGCCAGG  TCCTGGCGCT  TATAATTTGC  CATGTCTCTT  ACCACAAGAG  1320

TACATTTCAC  ATCTTGCTAG  CGAGCAAGCC  CCTACTGTAG  GTGAGGCTGC  CCTGCTCCAC  1380

TATGTTGACC  CTGATACTGG  TAGGAATCTT  GGAGAATTCA  AAGCATACCC  TGATGGTTTC  1440

CTCACTTGTG  TCCCCAATGG  TGCTAGCAGC  GGTCCACAAC  AACTGCCAAT  CAATGGTGTC  1500

TTTGTCTTTG  TTTCATGGGT  GTCAAGATTT  TATCAATTAA  AGCCTGTGGG  AACTGCCTCT  1560

AGCGCAAGAG  GTAGGCTTGG  TCTTAGGAGG  TAA                                 1593
```

The sNVCP having SEQ ID NO: 4 encodes an amino acid having 100% homology to the native NVCP amino acid (SEQ ID NO: 2). FIGS. 1A-F show an alignment of the native NVCP nucleotide sequence (SEQ ID NO: 1) and the sNVCP plant-optimized nucleic acid molecule having SEQ ID NO: 3. The contig sequence for the alignment is shown in FIGS. 1A-F as SEQ ID NO: 5. In FIGS. 1G-H the amino acid sequence of native NVCP (SEQ ID NO: 2) is aligned with the amino acid sequence (SEQ ID NO: 6) encoded by the plant-optimized sNVCP nucleic acid molecule having SEQ ID NO: 3. The MET to ILE mutation is shown bolded in FIG. 1G at position 253. The consensus sequence for the alignment is shown in FIGS. 1G-H as SEQ ID NO: 7.

Also suitable as synthetic plant-optimized nucleic acid molecules of the present invention are nucleic acid molecule encoding the capsid protein of any strain of Norwalk virus or Norwalk-like virus, which are "plant-optimized" as described above. These include, without limitation, Norwalk-like viruses of the *calicivirus* genogroups 1 and 2, including, but not limited to, the strains identified in Table 1 below by their GenBank Accession number (which are hereby incorporated by reference in their entirety):

TABLE 1

Norwalk-Like Viruses: Genbank Accession Nos.

| | | |
|---|---|---|
| AF414403 | AF414402 | AF414406 |
| AF493224 | U02030 | X76716 |
| AF414423 | AFR414407 | AF414409 |
| AF145896 | AF397905 | U07612 |
| AF414426 | AY580335 | AY581254 |
| X81879 | AY485642 | AB031013 |
| AB021996 | AB021995 | AB021994 |
| AB021993 | AB021992 | AB0219941 |
| AB021990 | AB021989 | AB021988 |
| AB021987 | AY247442 | AY247441 |
| AY247440 | AY247439 | AY247438 |
| AY247437 | AY247436 | AY247435 |
| AY247434 | AY247433 | AY247432 |
| AY247431 | AB032758 | AF472623 |
| X86557 | AF435807 | AJ487807 |
| AF542090 | AF539440 | AF539439 |
| AY130762 | AY130761 | AF397156 |
| AY081134 | AY030313 | AY030312 |
| AY030098 | AF145709 | AF439267 |
| AF394960 | AF36881 | AF427123 |
| AF427122 | AF427121 | AF427120 |
| AF427119 | AF427118 | AF427117 |
| AF427116 | AF427115 | AF427114 |

TABLE 1-continued

Norwalk-Like Viruses: Genbank Accession Nos.

| | | |
|---|---|---|
| AF427113 | AF427112 | AF427111 |
| AF425769 | AF425768 | AF425767 |
| AF425766 | AF425765 | AF425764 |
| AF425763 | AY054300 | AY054299 |
| AF414427 | AJ277621 | AJ277620 |
| AJ277619 | AJ277618 | AJ277617 |
| AJ277616 | AJ277615 | AJ277614 |
| AJ277613 | AJ277612 | AJ277611 |
| AJ277610 | AJ277609 | AJ277608 |
| AJ277607 | AJ277606 | AF359452 |
| AF312937 | AF312936 | U75682 |
| U70059 | U07611 | AF195848 |
| AF195847 | AF156765 | AF194182 |
| AB022679 | AJ004864 | U65427 |
| U22498 | U46039 | L07418 |

The sNVCP nucleotide sequences of the present invention may be synthesized using standard methods of nucleic acid synthesis known in the art.

The present invention also relates to a nucleic acid construct having a synthetic plant-optimized nucleic acid molecule of the present invention encoding a Norwalk virus capsid protein, a 5' DNA promoter sequence, and a 3' terminator sequence. The promoter and the terminator are operatively coupled to the Norwalk virus capsid protein encoding sequence in the nucleic acid construct to allow expression of the Norwalk virus capsid protein in a plant.

The sNVCP nucleotide sequences of the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC110, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

In preparing a nucleic acid vector for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens*. Fraley, et al., "Expression of Bacterial Genes in Plant Cells," *Pro. Nat'l Acad Sci USA* 80:4803-4807 (1983), which is hereby incorporated by reference in its entirety.

Further improvement of this technique led to the development of the binary vector system (Bevan, M., "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19. Frisch, et al., "Complete Sequence of the Binary Vector Bin19," *Plant Molec. Biol.* 27:405-409 (1995), which is hereby incorporated by reference in its entirety. Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopaline synthase (NOS) gene promoter, from *Agrobacterium tumefaciens* (U.S. Pat. No. 5,034,322 issued to Rogers et al., which is hereby incorporated by reference in its entirety), the cauliflower mosaic virus (CaMV) 35S and 19S promoters (U.S. Pat. No. 5,352,605 issued to Fraley et al., which is hereby incorporated by reference in its entirety), those derived from any of the several actin genes, which are known to be expressed in most cells types (U.S. Pat. No. 6,002,068 issued to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc Natl Acad Sci USA* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog. Schena et al., "A Steroid-Inducible Gene Expression System for Plant Cells," *Proc Natl Acad Sci USA* 88:10421-5 (1991); Aoyama et al., "A Glucocorticoid-Mediated Transcriptional Induction System in Transgenic Plants," *Plant J.* 11: 605-612 (1997), and McNellis et al., "Glucocorticoid-Inducible Expression of a Bacterial Avirulence Gene in Transgenic *Arabidopsis* Induces Hypersensitive Cell Death, *Plant J.* 14(2):247-57 (1998), which are hereby incorporated by reference in their entirety. In addition, inducible promoters include promoters that function in a tissue specific manner to regulate the gene of interest within selected tissues of the plant. Examples of such tissue specific or developmentally regulated promoters include seed, flower, fruit, or root specific promoters as are well known in the field (U.S. Pat. No. 5,750,385 issued to Shewmaker et al., which is hereby incorporated by reference in its entirety). In the preferred embodiment of the present invention, a heterologous promoter is linked to the nucleic acid of the construct, where "heterologous promoter" is defined as a promoter to which the nucleic acid of the construct is not linked in nature.

The nucleic acid construct of the present invention also includes an operable 3' regulatory region, selected from among those which are capable of providing correct transcription termination and polyadenylation of mRNA for expression in the host cell of choice, operably linked to a modified trait nucleic acid molecule of the present invention.

A number of 3' regulatory regions are known to be operable in plants. Exemplary 3' regulatory regions include, without limitation, the nopaline synthase ("nos") 3' regulatory region (Fraley, et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell, et al., "Identification of DNA Sequences Required for Activity of the Cauliflower Mosaic Virus 35S Promoter," *Nature* 313(6005):810-812 (1985), which is hereby incorporated by reference in its entirety). Virtually any 3' regulatory region known to be operable in plants would suffice for proper expression of the coding sequence of the nucleic acid of the present invention.

The different components described above can be ligated together to produce the expression systems which contain the nucleic acid constructs of the present invention, using well known molecular cloning techniques as described in Sambrook et al., *Molecular Cloning: A Laboratory Manual*, Second Edition, Cold Spring Harbor Press, NY (1989), and Ausubel et al. (1989) *Current Protocols in Molecular Biology*, John Wiley & Sons, New York, N.Y., which are hereby incorporated by reference in their entirety. In a preferred embodiment of the present invention, the sequence encoding the synthetic, plant-optimized Norwalk virus capsid protein is in proper sense orientation in the nucleic acid construct of the present invention.

The nucleic acid construct of the present invention is configured to encode RNA molecules which are translatable. As a result, that RNA molecule will be translated at the ribosomes to produce the protein encoded by the nucleic acid construct. Production of proteins in this manner can be increased by joining the cloned gene encoding the nucleic acid construct of interest with synthetic double-stranded oligonucleotides which represent a viral regulatory sequence (i.e., a 5' untranslated sequence) (U.S. Pat. No. 4,820,639 to Gehrke, and U.S. Pat. No. 5,849,527 to Wilson, which are hereby incorporated by reference in their entirety).

Once the nucleic acid construct of the present invention has been prepared, it is ready to be incorporated into a host cell. Accordingly, another aspect of the present invention relates to a recombinant host cell containing a nucleic acid constructs having one or more of the plant-optimized nucleic acid molecules of the present invention. Basically, this method is carried out by transforming a host cell with a nucleic acid construct of the present invention under conditions effective to yield transcription of the nucleic acid molecule in the host cell, using standard cloning procedures known in the art, such as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the nucleic acid under control of the promoter. Preferably, a nucleic acid construct of the present invention is stably inserted into the genome of the recombinant plant cell as a result of the transformation, although transient expression can serve an important purpose, particularly when the plant under investigation is slow-growing.

Plant tissue suitable for transformation include leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue is often achieved by particle bombardment (Klein et al., "High-Velocity Microprojectiles for Delivering Nucleic Acids Into Living Cells," *Nature* 327:70-73 (1987), which is hereby incorporated by reference in its entirety). In this method, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign nucleic acid molecule into plant cells. Another approach to transforming plant cells with a gene which imparts resistance to pathogens is particle bombardment (also known as biolistic transformation) of the host cell, as disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety. Yet another method of introduction is fusion of protoplasts with other entities, either minicells, cells, lysosomes, or other fusible lipid-surfaced bodies (Fraley, et al., *Proc Natl Acad Sci USA* 79:1859-63 (1982), which is hereby incorporated by reference in its entirety). The nucleic acid molecule may also be introduced into the plant cells by electroporation (Fromm et al., *Proc Natl Acad Sci USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures, Vol.* 1: (MacMillan Publishing Co., New York, 1983); Vasil I. R. (ed.), *Cell Culture and Somatic Cell Genetics of Plants*, Acad. Press, Orlando, Vol. 1, 1984, and Vol. III (1986), and Fitch et al., "Somatic Embryogenesis and Plant Regeneration from Immature Zygotic Embryos of Papaya (*Carica papaya* L.)," *Plant Cell Rep.* 9:320 (1990), which are hereby incorporated by reference in its entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the nptII gene which confers kanamycin resistance (Fraley et al., *Proc Natl Acad Sci USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS. Jefferson et al., "GUS Fusions: βGlucuronidase as a Sensitive and Versatile Gene Fusion Marker in Higher Plants," *EMBO J.* 6:3901-3907 (1987), which is hereby incorporated by reference in its entirety. Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the viral gene by Southern blot hybridization analysis, using a probe specific to the viral genes contained in the given cassette used for transformation (Sambrook et al., "*Molecular Cloning: A Laboratory Manual*," Cold Spring Harbor, N.Y.: Cold Spring Harbor Press (1989), which is hereby incorporated by reference in its entirety).

After the fusion gene containing a nucleic acid construct of the present invention is stably incorporated in transgenic plants, the transgene can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds are recovered from the transgenic plants. These seeds can then be planted in the soil and cultivated using conventional procedures to produce transgenic plants.

The present invention can be utilized in conjunction with a wide variety of plants or their seeds. Suitable plants include dicots and monocots. Useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, and sugarcane.

Another aspect of the present invention is a method of producing Norwalk virus capsid protein virus-like particles. This method involves providing a transgenic plant or plant seed transformed with a synthetic plant-optimized nucleic acid molecule encoding a Norwalk virus capsid protein, and growing the transgenic plant or a transgenic plant grown from a plant seed of the transgenic plant under conditions effective to produce Norwalk virus capsid protein virus-like particles. In one aspect of the present invention, the Norwalk virus capsid protein virus-like particles comprise a conformational epitope that reacts with an antibody raised against a native Norwalk virus virion. The nucleic acid molecule of this aspect is selected from among the *Noroviruses* described above, including, but not limited to, Norwalk virus.

As used herein, "virus-like particle(s) (VLPs)" refer to a virus-like particle(s), fragment(s), or portion(s) thereof produced from the capsid protein coding sequence of Norwalk virus and comprising antigenic characteristic(s) similar to those of infectious Norwalk virus particles. As used herein, "antigenic characteristic(s)" refers to (1) the ability of the virus-like particle(s) to cross-react with wild-type particles (native infectious Norwalk virus particles as determined by antisera generated in animals and/or humans by immunization with either VLPs or infectious virus; and/or (2) the ability to recognize or detect antibodies in human sera from persons known to be infected with homologous virus.

Nucleic acid molecules, vectors, host cells, and plants suitable for this aspect of the present invention are as described above. Transformation and regeneration of selected plants and production of transgenic plant seeds can be carried out as described above.

Another aspect of the present is a method of immunizing a subject against disease resulting from infection by a *Norovirus*. This method involves administering the plant of the present invention transformed with a synthetic plant-optimized nucleic acid molecule encoding a Norwalk virus capsid protein, or a component part or a fruit of the plant, to the subject under conditions effective to immunize the subject against disease resulting from infection by a *Norovirus*, including, but not limited to, Norwalk virus. Administering is desirably carried out by feeding the transgenic plant, or a component part, or a fruit thereof, to the subject. Administration (i.e., feeding), in accordance with the present invention, could be given by untrained personnel, and is amenable to self-application. Large-scale field administration could occur given the easy accessibility to treatment. Additionally, a simple administration procedure would improve access to treatment by pediatric patients and the elderly, and populations in Third World countries.

The ability of an immunogen to establish a memory response is a key element in the design of an efficacious vaccine. Responses to oral boosting observed in mice (described in the Examples below) indicate the generation of antigen-specific memory cells. Thus, following an initial feeding administration, a vaccine "booster" may be administered by further feedings of the Norwalk virus VLPS-producing plant of the present invention or a component or fruit thereof.

Another aspect of the present invention is an oral vaccine for immunization of a subject against infection by a *Norovirus*, including, but not limited to, Norwalk virus. This vaccine is a component of the plant transformed with a synthetic plant-optimized nucleic acid molecule encoding a Norwalk virus capsid protein, where the plant produces Norwalk virus capsid protein virus-like particles for immunization of a subject against infection by Norwalk virus, and a pharmaceutical adjuvant. This transgenic plant is prepared as described above, such that a nucleic acid molecule having SEQ ID NO: 3 or SEQ ID NO: 4 is operably linked to a constitutive 5' promoter and a 3' terminator suitable for expression in plants is inserted in to the plant. When a constitutive promoter is used, the Norwalk virus capsid protein-like virus particles will be expressed through the plants tissues. Therefore, vaccine in the form of Norwalk virus capsid protein VLPs can be made from any plant component, including but not limited to, leaf tissue and the fruit of the plant. Alternatively, the promoter may be an inducible or tissue specific promoter if desired. To obtain the immunogenic Norwalk virus VLPs from the plant component, the desired plant tissue or the fruit of the plant can be subjected to a drying process, for example freeze-drying or air-drying, following procedures known in the art or as described in the Examples, below. The vaccine may additionally include any suitable adjuvant to enhance the immunogenicity of the vaccine when administered to a patient. Such adjuvants may include, without limitation, extracts of *Quillaja saponaria* (QS), including purified subfractions of food grade QS such as Quil A and QS-21. Doses of purified QS extracts suitable for use in a human vaccine formulation are from 0.01 mg to 10 mg per kilogram of bodyweight. The use of QS extracts is described in greater detail in the Examples, below. In addition, the adjuvants described here is suitable for use in other plant derived vaccines.

EXAMPLES

Example 1

Plant-Optimized Norwalk Virus Capsid Protein Gene

The coding sequence of the NVCP gene of Norwalk Virus (Genbank accession number M87661-genome for Norwalk Virus; or AAB50466 specifically for the NV capsid protein, which is hereby incorporated by reference in its entirety) was analyzed for codon use, and for the presence of undesired sequence motifs that could mediate spurious mRNA processing and instability, or methylation of genomic DNA. A plant-optimized coding sequence was designed with hybrid codon preference reflecting dicotyledon plant codon usage. A comparison of the "plant-optimized" and native sequences for NVCP is provided in FIGS. 1A-H. The optimized sequence was divided into a series of overlapping oligonucleotides of approximately 40-50 bases in length. The series of oligonucleotides were produced by a commercial supplier. The gene was assembled by overlap extension PCR. The gene was cloned into a commercial cloning vector and verified by DNA sequencing by the dideoxy chain termination method. The resulting Master plasmid is called pNVCP3.

A plant-optimized NVCP nucleic acid molecule was synthesized having plant-preferred codons, and aberrant mRNAs were removed to optimize the viral NVCP nucleic acid for expression in a plant host. Also added were appropriate restriction sites suitable for further manipulation. This synthetic NVCP gene (sNVCP) was designed by altering 108 of 1584 nucleotides in native NVCP gene to plant-favored codons, and removing 26 'CG' and 8 'CC' dinucleotides. This was accomplished in a 3-step process as follows:

Step 1: Optimize all the codons according to the rules known in the art; reduce the number of CG and CnG sequences as much as possible, without introducing unfavorable codons; and remove the 'trouble sequences' that were indicated.

Step 2: Check the optimized sequence for newly introduced 'trouble sequences' and remove these.

Step 3: Introduce restriction sites in and next to the sequence encoding loops that may be useful for the insertion of epitopes, and design restriction sites for cloning without introducing unfavorable codons.

The construction of both sNVCP nucleic acid molecules of the present invention were carried out by annealing and ligating overlapping oligonucleotides using the ligase chain reaction followed by limited PCR with a proof-reading PCR system. Results indicate that most nucleotide discrepancies were characterized by single nucleotide deletions, suggesting that the quality of the oligonucleotides was the important factor, rather than PCR induced errors. Hence, to reduce the amount of clones to be sequenced in future constructions, it is recommended that HPLC or PAGE purified oligonucleotides be used.

The loops used for epitope insertion in the NVCP nucleic acid molecule are positions 285-300 and 324-343 (aa numbering). The first one is flanked by a Hind III and a Bcl I site and contains a Kpn I site as well. The second loop is flanked by a Bgl II and a SalI site and contains a Bal I site as well. The sNVCP nucleic acid construct was cut with BsrGI and SacI, and ligated into pBluescript SKII+ digested with Acc65I and SacI. This removes most of the polylinker of the vector, and makes the restriction sites around the loops unique. Further cloning of the gene into the present plant expression vectors can be done by cutting the gene from the vector with XbaI and SacI, as described herein below.

Example 2

Construction of Plant Expression Plasmid with NVCP Gene

The first stage of producing the oral transgenic Norwalk virus vaccine of the present invention was to insert the plant-optimized NVCP gene into a plasmid vector in such a way that the gene could be produced in the desired plant host. The plasmid pNVCP3, containing the plant-optimized NVCP gene having SEQ ID NO: 3, in an XbaI/SacI fragment, was selected for expression in a tomato and potato plants. The binary vector plasmid, pPS 1, containing the NptII gene, a CaMV 35S promoter, TEV 5' UTR, and vspB 3 (vegetative storage protein beta terminator) sequence was obtained by ligating the expression cassette on a HindIII/EcoRI fragment into pGPTV-Kan (Becker et al., "New Plant Binary Vectors with Selectable Markers Located Proximal to the Left T-DNA Border," *Plant Mol. Biol.* 20:1195-1197 (1992), which is hereby incorporated by reference in its entirety). The CaMV 35S promoter was chosen because it is a constitutive promoter that causes gene expression throughout all plant tissues.

The plasmids were digested with XbaI and SacI and gel extraction performed to purify the two fragments, which were then ligated to create psNV110. This procedure is shown in FIG. 2A. The vector pNV110 was made by ligation of the native NVCP gene from pNV1028 with pPS1. FIG. 2B shows the structure of plasmid vectors psNV110 and pNV110 used for expression of the plant-optimized Norwalk virus VLPs and native Norwalk virus VLPs, respectively. The clones were screened by PCR and confirmed by DNA sequencing for the presence of the nucleic acid molecule before transfer into *Agrobacterium* for plant transformation. Established methods for recombinant DNA manipulations were used to prepare the expression vectors (Sambrook et al., *Molecular Cloning: A Laboratory Manual*, Second Edition, Cold Spring Harbor Press, NY (1989), which is hereby incorporated by reference in its entirety). In general, nucleic acid fragments obtained by digestion of selected plasmids or by PCR were resolved by electrophoresis in agarose/TAE gels and purified by gel extraction using QIAquick Nucleotide Removal Kit (Qiagen, Valencia, Calif.). Ligation reactions were used to transform *E. coli* strain DH5α and plasmids were propagated in that strain. Final constructs were verified by restriction digestion, PCR, and sequencing.

Figure 3:
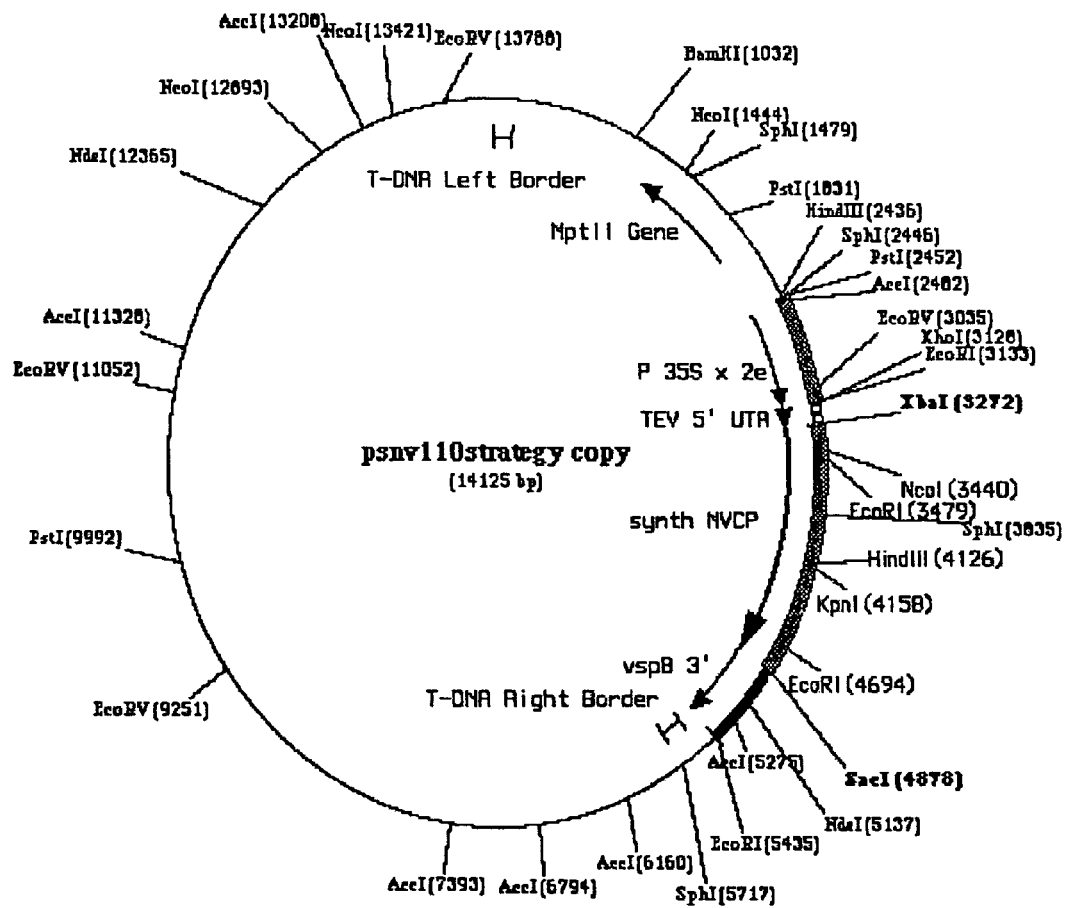
FIG. 3 is a map of psNV110 vector and orientation of components. The sNVCP expression cassette is located between the right and left T-DNA borders allowing *Agrobacterium*-mediated insertion of the entire T-DNA into the plant nuclear chromosomal DNA. The T-DNA region consists of a neomycin phosphotransferase (NPTII) gene which transfers kanamycin resistance for transgene selection, the cauliflower mosaic virus (CaMV) 35 S promoter which drives transcription of the NVCP gene, the tobacco etch virus 5' untranslated region (TEV 5'-UTR), and the vegetative storage protein B terminator untranslated region (VspB 3'-UTR).

The map for plasmid vector "psNV110" (plasmid, synthetic gene, Norwalk Virus) is shown in FIG. 3, which describes the elements of the vector. As seen in FIG. 3, the expression cassette for synthetic NVCP (the nucleic acid sequence optimized for dicotyledon plant expression) begins at the HindIII site (position 2436) and continues through to the EcoRI site (position 5435).

Master cell stocks were created for psNV110 in both *E. coli* strain DH5α and *A. tumefaciens* strain LBA4404. Live cell stocks were prepared in duplicate, preserved in 70% glycerol, and stored at −80° C. Purified DNA preparations of plasmid psNV110 were prepared, and stored at −80° C. Seed from all generations of plant line sNV110-2 were collected, dried, and packaged for dry storage at room temperature.

Master plasmids pNVCP3 and pPS1 provided the primary components to form transformation vector psNV110. The master plasmid, pNVCP3 provided the plant-optimized sNVCP gene (having SEQ ID NO: 3) for NVCP as described above, within an XbaI/SacI fragment. The second master plasmid, pPS1, which contains the NptII gene, 35S promoter, TEV leading sequence, and vspB3 terminal sequence, was constructed having the above mentioned regulatory sequences and the pGPTV-Kan binary vector backbone (Becker et al., "New Plant Binary Vectors with Selectable Markers Located Proximal to the Left T-DNA Border," *Plant Mol. Biol.* 20:1195-1197 (1992), which is hereby incorporated by reference in its entirety). The master plasmids were digested with Xba1 and SacI and gel extraction performed to purify the two fragments. The synthetic NVCP gene and regulatory sequences were then ligated together to create the psNV110 plasmid. Vector psNV110 was then cloned into *E. coli* DH5α and propagated in culture. The clones were screened by PCR and confirmed with sequencing before transformation.

Example 3

Plasmid Transfer to *Agrobacterium* and Plant Transformation

The next stage was to transfer the binary plasmid vector to the bacterium *Agrobacterium tumefaciens*. This bacterium was then used to inoculate plant cells and transfer the psNV110 gene flanked by T-DNA borders to the plant. Plasmids pNV110 and psNV110 were electroporated into *Agrobacterium tumefaciens* strain LBA4404 and kanamycin-resistant colonies were screened by PCR and confirmed by restriction enzyme digestion. Plasmid prepared from transformed *Agrobacterium* lines was characterized by restriction digestion and compared to the plasmid prepared from *E. coli* DH5α to confirm the presence of psNV110.

Tomato (*Lycopersicon esculentum* variety "TA234") and potato (*Solanum tuberosum* L. cv Desiree) were used as hosts for genetic transformation by *Agrobacterium tumefaciens* containing psNV110 and pNV110. Transformations were carried out by modified stem or leaf-disc co-cultivation methods. An *Agrobacterium* streaked LB-kanamycin plate was incubated for 24-48 hours at 28° C. Four kanamycin resistant colonies were grown in YM selective liquid medium in a shaking incubator until the culture reached an OD600 of 0.5-0.6. The cultures were centrifuged and re-suspended in MS liquid medium.

Figure 4:
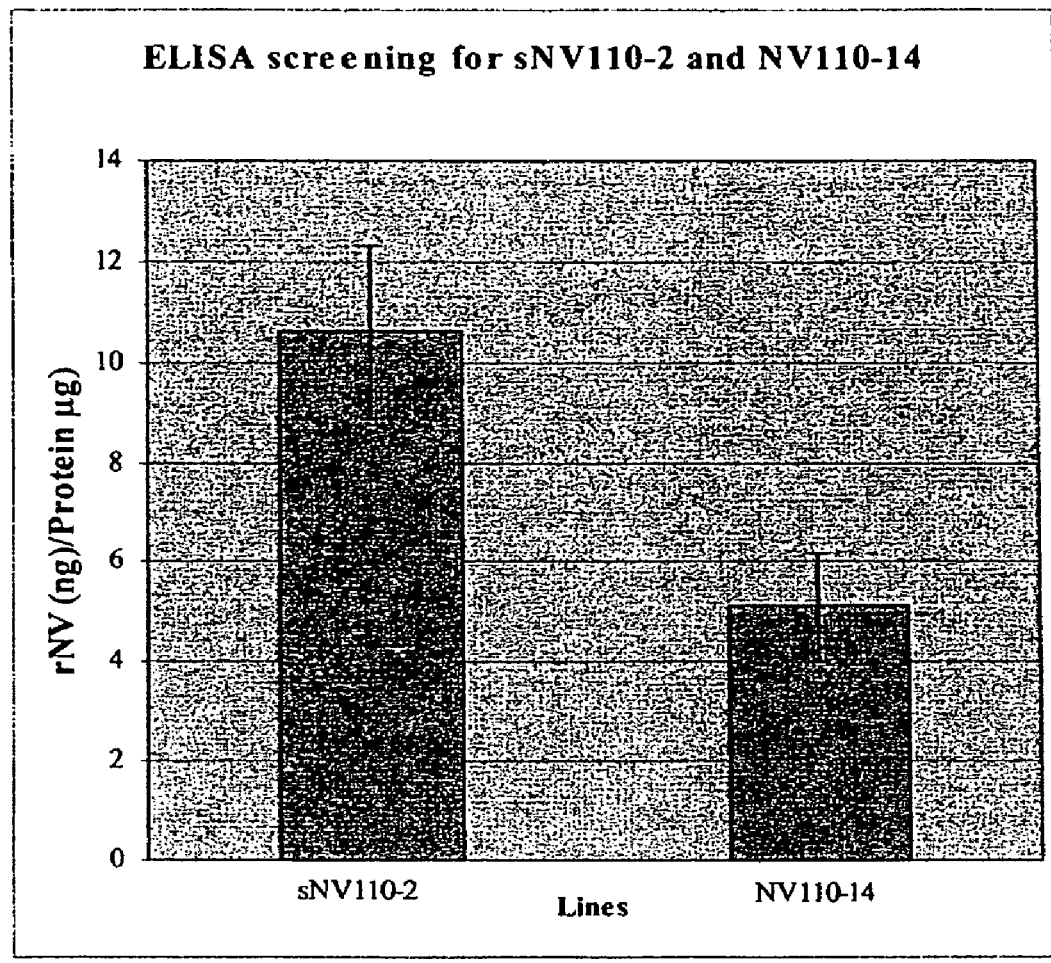
FIG. 4 shows a comparison of rNV expression in line sNV110-2 and native NVCP gene expression in line NV110-14. Analysis by ELISA was performed to compare NVCP expression between elite lines generated to express either the native NVCP gene (line NV110-14) or the synthetic gene (line sNV110-2). Use of the plant-optimized coding sequence for NVCP exhibited a 2-fold improvement in detectable antigen. This improvement, coupled with increased potency displayed during clinical evaluation, contributed to the selection of plant line sNV110-2 as the preferred master seed for human clinical evaluation.

Tomato cotyledon explants were incubated in the *Agrobacterium* suspension and co-cultivated at 19° C. in the dark for 48 hours. Plantlets were regenerated on medium containing kanamycin to select for plantlets containing the nptII expression cassette and its linked NVCP cassette integrated into the plant cell nuclear chromosomal DNA. Individual transformed lines were screened by ELISA for NVCP expression in leaves, and the best expressors were clonally propagated in vitro by subculture of the meristem and stem nodes to multiply the number of plants for transferring into soil. During transformations using psNV110, regenerative clone number 2 was evaluated as the highest expressor by ELISA analysis of transgenic fruit, as shown in FIG. 4. Therefore, this line, designated sNV110-2, was taken forward for further propagation and fruit and seed collection for production of clinical materials. Transformed lines can be maintained indefinitely by such in vitro clonal propagation or seeds can be harvested, dried, and stored for many years. Leaves have been tested periodically by ELISA for expression of NVCP during this propagation.

After co-cultivation with *Agrobacterium*, cotyledon explants were cultured on Stage I selective medium containing 100 mg/l kanamycin and 300 mg/l timentin, which inhibits *Agrobacterium* growth outside of the plant. Three weeks later, the cultures were transferred to a Stage II medium containing 100 mg/L kanamycin and 300 mg/l timentin and transferred to fresh medium at 3 week intervals. When shoots were 2 cm tall, they were transferred to selective rooting medium containing 50 mg/l kanamycin but lacking timentin, to see if any *Agrobacterium* remained in the plant. Plantlets were maintained on cloning medium by subculture of meristem and stem node cuttings and then transplanted to soil in the greenhouse to produce fruit. During maintenance of the plantlets, the plantlets and media were routinely checked for any signs of bacterial or fungal growth or contamination and any such materials would have been immediately discarded.

Example 4

Regeneration and Propagation of Transgenic Tomato Plants

Tomato plants were then regenerated from cotyledon culture to form plantlets as described in detail above, and then, whole plants able to produce fruit and seeds. Plant line sNV110-2 was chosen because it contained both mRNA transcripts and had high antigen production in fruit (see Examples below). Plants can be propagated either from plantlets grown in tissue culture or from stored seeds. The tomato plants were grown under appropriate biosafety level 1 containment. FIG. 5 is a flow diagram that describes the process of vaccine production from initiation of plant transformation to harvest of fruit for vaccine administration. Anecdotal evidence suggests that there is no appreciable difference in foreign antigen expression after serial passages.

Fourth generation tomato vaccine plants were produced using seeds from the 3d generation of tomato plants as starting material. Third generation seeds were planted in Cornell+ Osmocote soil in one-inch pots. They were maintained in a controlled greenhouse at 25° C. (day) and 20° C. (night) with supplemental lighting provided by sodium vapor lamps to give 16 hours of light per day. Excel 15-5-15+330 Sprint (Fe) fertilizer was applied daily at 100 ppm. After the second true leaves were developed (week 4), the seedlings were sprayed with 400 mg/l kanamycin to confirm transgene activity, and all positive plants transferred to 4 inch pots. After 7 weeks the seedlings were assayer-evaluated by NVCP ELISA, any negative or low expressing plants were autoclaved and composted, and the most robust positive plants were transferred to 3-gallon pots. One application of the pesticide Micro-Sulf (Agtrol International, Houston, Tex.) was applied in accordance with manufacturer's instructions as a method of controlling powdery mildew. Micro-Sulf (active ingredient sulfur) is licensed for use within the USA for application on commercial tomato crops. The plants were grown for a total of 18 weeks and then all foliage, roots, soil, and other plant materials were devitalized by autoclaving and composted.

A noticeable characteristic of sNV110-2 was that the fruit ripened less rapidly and less evenly than non-transgenic fruit. This phenomenon imparts a color difference that has been seen frequently in other transgenic lines. It was determined that the color difference is physiological and not detrimental to antigenic effects or to oral efficacy based on materials tested in animal trials.

Example 5

Fruit Harvesting and Processing

Fruit were harvested and processed for freeze-drying during weeks 15-18 according to the following protocol summarized here. All plants for batches sNV110-2 (Vaccine Tomatoes) and TA234-C (Control Tomatoes) were greenhouse grown under controlled environmental conditions with one application of Microsulf as described above. Fruit were harvested when they were considered to have reached at least ripening stage 4 (pink/orange fruit with 30-60% red), and preferably prior to over-ripening. Harvesting was conducted at 3-5 day intervals for a period of 3 weeks. All Control (non-transgenic) fruit were harvested and processed prior to harvesting of Vaccine (transgenic) fruit. Fruit were hand-picked from the plants and any stem or leaf materials were removed. Fruit were washed in a 1% bleach solution and thoroughly rinsed with deionized water, weighed, and immediately processed per the steps below. At the completion of the harvest, all remaining plant materials (Vaccine and Control) and associated soil were devitalized by autoclaving and composted.

Tomato processing was carried out in two facilities, a "primary" and a "secondary" processing facility, as follows. At the primary facility, all overripe fruit or fruit with extensive blossom end rot were removed. Freshly harvested fruit were cross sectioned through the center and seeds were removed manually to be used for seed collection or devitalized by autoclaving. Fleshy fruit tissue were cut in approximately ¼ inch slices, weighed, and stored in labeled FDA approved Ziploc bags in a −20° freezer. At completion of harvest and after all fruit was fully frozen, fruit was removed and transported in coolers with dry ice to the secondary processing facility. All equipment coming into contact with the tomatoes was washed with a 1% bleach solution and rinsed well with water. At the secondary processing facility, the frozen material was removed from the bags and placed in labeled stainless steel trays and immediately placed in an industrial freeze-drier already chilled to −60° C. The materials underwent freeze-drying for a minimum of 85 hours at a maximum shelf temperature of 20° C. The materials were removed from the freeze-drier for a few minutes on day 3 to break up large pieces of material to insure full drying. Dried materials were then combined in U.S. Dept of Food and Drug Administration (FDA) approved 4 millimeter polyethylene bags (separate for Control and Vaccine) and heat sealed.

Materials were transported back to the primary processing facility and stored at room temperature. After final antigen concentration was ascertained, the material was crushed into a fine powder, measured into individual doses and packaged in FDA approved gelatin capsules (Nutraceutical, Park City, Utah), sealed, and stored at room temperature in clearly labeled packages. Control materials were similarly reduced to powder, packed into capsules and stored in labeled packages.

FIG. 5 is a flow diagram outlining the process of formation of the whole plants. The glossary that follows provides definitions for the terms used in FIG. 5.

Clonally Propagated Plants: The plants recovered when an individual plant is divided by cutting the stem into segments, each of which contains a node that can generate a new stem. The node cuttings are subcultured in vitro to yield genetically identical plantlets, which can then be either clonally propagated in vitro or transplanted to soil.

Master Plant Bank: The transformed tomato line selected for high expression of NVCP (line sNV110-2), maintained in tissue culture by clonal propagation of stem node cuttings, and tested periodically by ELISA for NVCP expression in fruit.

Transformed Plant Line: An individual plant and its clonally propagated progeny arising from a single regenerated shoot following *Agrobacterium*-mediated transformation of a plant cell.

First Generation (T1) Fruit: Fruit harvested from plants that were transplanted to soil from the Master Plant Bank. These fruit are tested by ELISA for NVCP expression.

First Generation (T1) Seed: Seed harvested from First Generation Fruit. Seeds can be germinated in soil and the plants tested by ELISA for NVCP expression.

Second Generation (T2) Fruit: Fruit harvested from plants that were germinated from first generation seed. These fruit are tested by ELISA for NVCP expression and used for animal testing (as described in greater detail below).

Second Generation (T2) Seed: Seed harvested from Second Generation Fruit.

Third Generation (T3) Fruit: Fruit harvested from plants that were germinated from second generation seed. These fruit are tested by ELISA for NVCP expression and used for animal testing (as described in greater detail below).

Third Generation (T3) Seed: Seed harvested from Third Generation Fruit.

Fourth Generation (T4) Fruit: Fruit harvested from plants that were germinated from third generation seed. These fruit are tested by ELISA for NVCP expression and used for human testing.

Fourth Generation (T4) Seed: Seed harvested from Fourth Generation Fruit.

Example 6

Molecular Analysis of Transgenic Plant Line sNV110-2

During the generation of the transgenic plants, analyses were done to demonstrate that the NVCP gene had been taken into the plant cells and integrated into the nuclear genome. Master seed selection and characterization began with initial analysis of leaves from young plantlets. Because the CaMV 35S promoter was used, the expression of the NVCP gene is constitutive in the plant and, therefore, transcription occurs in the leaf tissue. This allowed early inspection of the plants to determine which regenerated lines had integrated the gene. Later analyses were performed on fruit as described below.

Confirmation of the NVCP gene in plant tissues was shown by PCR analysis, as seen in FIG. 6 (described below in

Figure 7:
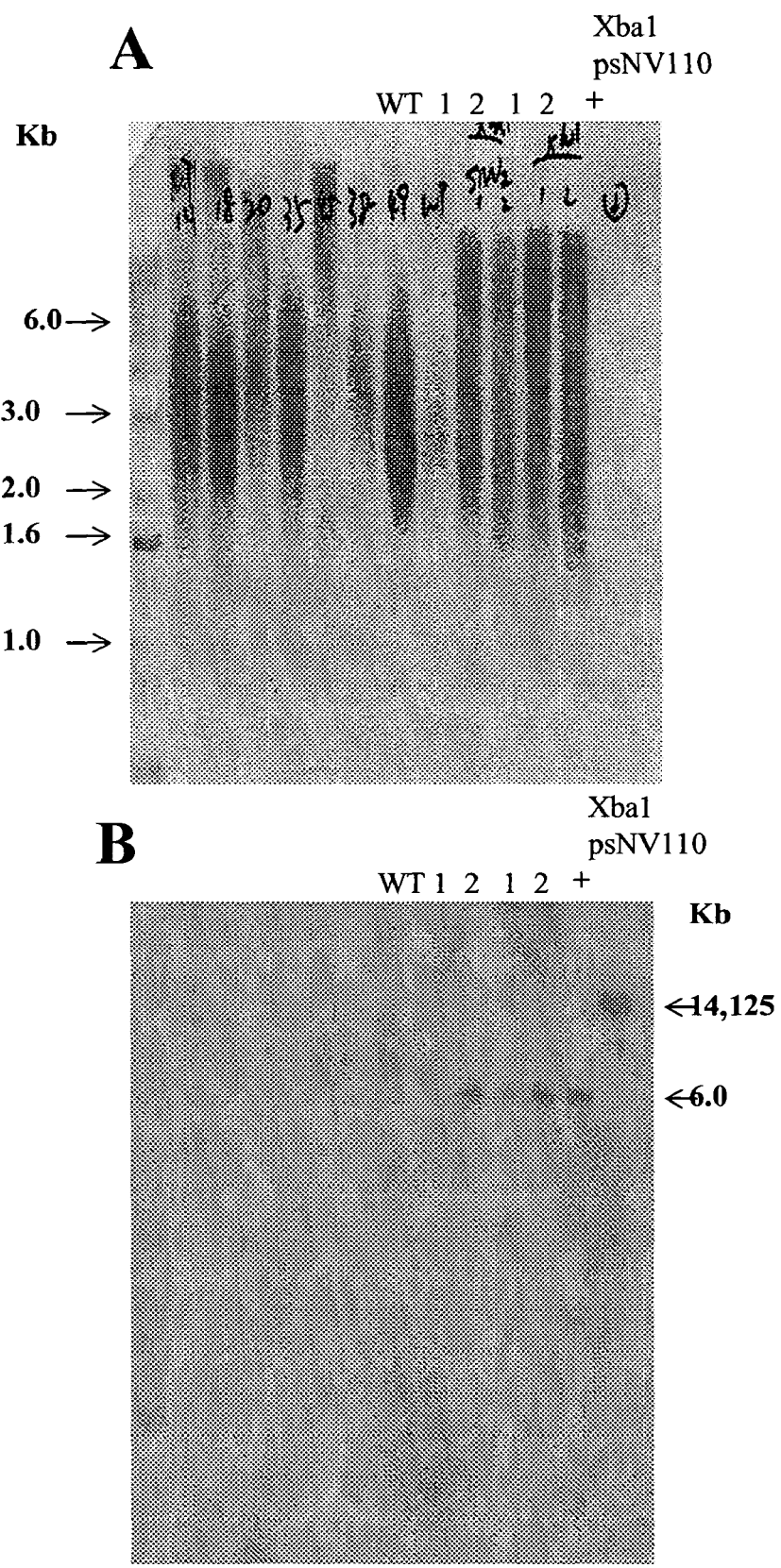
FIGS. 7A-B are a Coomassie blue stained gel and Southern blot, respectively. Southern blot analysis was performed to determine the number of transgene copies integrated into sNV110.
Figure 8:
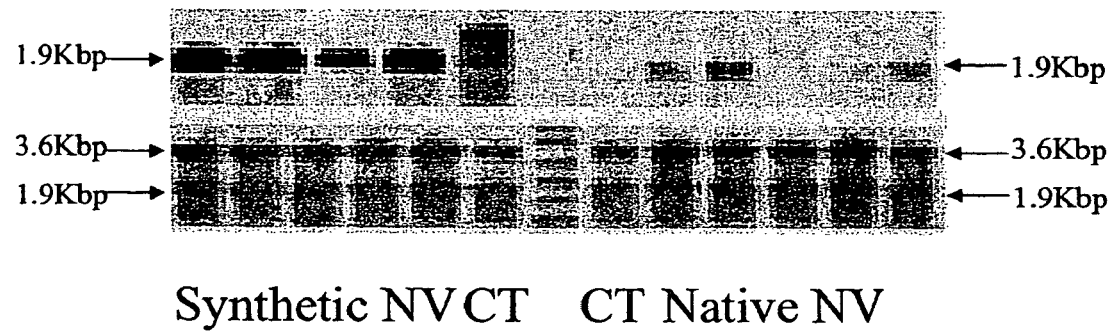
FIG. 8 is a northern blot analysis of tomato fruit. Total RNA was isolated from fruit tissue samples, denatured, and approximately 5 μg per lane was subjected to electrophoresis in a 1% agarose gel, blotted to ZetaProbe (Bio-Rad, Hercules, Calif.) nylon membrane, and probed using an NVCP internal template (created from primers sNV-forward and sNV-reverse). The lower image is a methylene blue stain of the gel to depict molecular markers.
Figure 9:
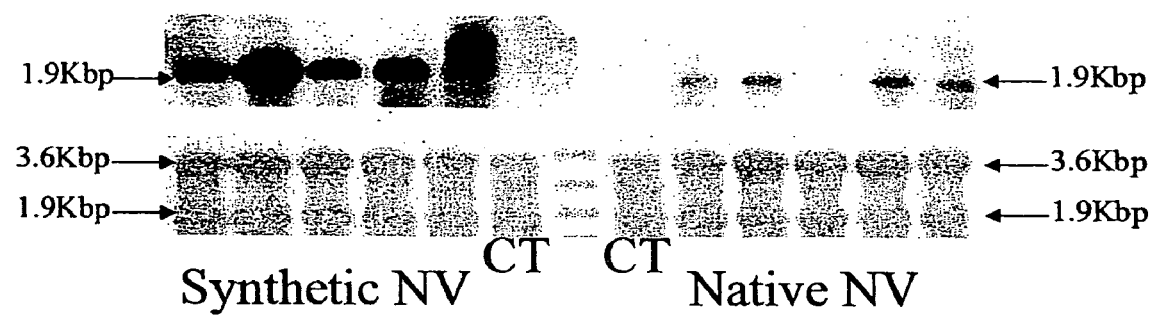
FIG. 9 is a northern blot analysis of tomato leaf tissue. Total RNA was isolated from transgenic leaf tissue samples, denatured, and approximately 5 μg per lane was subjected to electrophoresis in a 1% agarose gel, blotted to ZetaProbe (Bio-Rad, Hercules, Calif.) nylon membrane, and probed using an NVCP internal template (created from primers sNV-forward and sNV-reverse). The lower image is a methylene blue stain of the gel to depict molecular markers.
Figure 12:
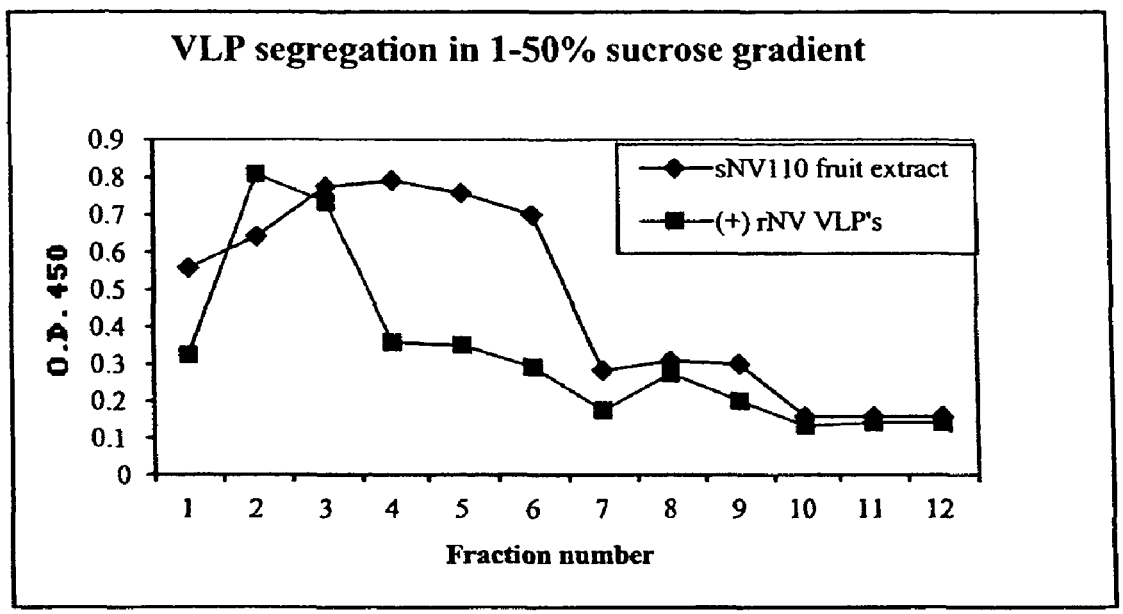

Example 7), and integration of the vector into the genome was characterized by Southern blot analysis of genomic DNA, as shown in FIGS. 7A-B. The PCR product obtained from sNV110-2 was also sequenced and confirmed the presence of the same sequence as the original vector psNV110. Northern blots were also performed on fruit RNA, shown in FIG. 8, and tomato leaf, shown in FIG. 9, to confirm that the gene was being expressed to produce the appropriate mRNA. Antigen was detected in the fruit, shown in FIG. 10, and tomato leaf, as shown in FIG. 11, using an antigen-specific ELISA. NVCP extracted from fruit sedimented within the sucrose gradient as VLPs in a pattern similar to baculovirus-produced VLPs, as shown in FIG. 12. The quantification reaction by western blot analysis, shown in FIGS. 13A-B, was also consistent with baculovirus-derived antigen and detected by NVCP-specific rabbit antisera.

Example 7

Analysis of sNVCP Expression in Transgenic Fruit and Plant Material

Tomato leaf genomic DNA was isolated from 1 g of leaf tissue by adding 0.75 ml of pre-warmed (65° C.) extraction buffer (2% w/v CTAB, 100 mM Tris-Cl pH 8.0, 20 mM EDTA pH 8.0, 1.4M NaCl, 2% 2-mercaptoethanol). One homogenizing bead was added to each sample and run in Fastprep at speed 5 for 30 seconds. Tubes were incubated at 65° C. for 60 minutes and opened periodically to remove any pressure buildup. Samples were centrifuged at 7500 rpm for 10 minutes at 4° C. The supernatant fraction was recovered and mixed with an equal volume of isopropanol. Tubes were inverted at room temperature for 10 minutes, and washed with 1 ml of 70% ethanol. Pellets were air-dried and cleaned by adding 200 µl autoclaved water and 6 µl RNase and kept at 37° C. for 10 min. Two volumes of 100% ETOH and ⅒ volume of 3M NaOAc were added and kept at 20° C. for 2 hours. Samples were centrifuged at 7500 rpm at 4° C. for 5 minutes. Pellets were washed with 70% ETOH and resuspended in 50 µl autoclaved water. DNA concentrations were calculated by spectrophotometry at 260 nm.

PCR was performed on genomic DNA samples from sNV110-2 using the 35S and Vsp-HT primers which bind 5' and 3' respectively to the flanking regions of the sNVCP coding sequence. The resulting PCR fragment produced should be 1750 bp in length. The sequences of the primers follow:

```
SEQ ID NO: 8    35S:     GAAGTGACAGATAGCTGGGC

SEQ ID NO: 9    Vsp-HT:  TGAATAGTGCATATCAGCATACCTTA
```

Reactions were prepared in accordance with the Expand High Fidelity PCR System protocol (Roche Diagnostics, Indianapolis, Ind.). The products were run on a 1% agarose gel in TAE buffer. The gel showed that sNV110-2 contains primer binding sites that generate a PCR product of the expected size (1750 bp), as shown in 6. This confirms the complete sNVCP gene was integrated into the plant cell.

A further separate PCR reaction from sNV110-2 genomic DNA was performed and run on a gel yielding fragments of 1750 bp. The fragments obtained were isolated by gel extraction using QIAquick Nucleotide Removal Kit 50 (Qiagen), and sequenced using sNV-forward, TEV-HT, and sNV-reverse as primers. The primer sequences are as follows:

```
SEQ ID NO: 10 sNV-forward:  CTTGTTTTTAGTCCCTCCTACAGT

SEQ ID NO: 11 TEV-HT:       CAAGCATTCTACTTCTATTGCAGC

SEQ ID NO: 12 sNV-reverse:  GCTAGCAAGATGTGAAATGTACTC
```

The original gene in the pNVCP3 plasmid was sequenced upon receipt and used to verify the sequence achieved here by PCR of the plant genome. Thus, the reaction was specific and it was determined that sNV110-2 contains the proper sNVCP gene sequence.

Southern blot analysis was performed on two of the genomic DNA samples used for PCR analysis. Twenty µg of each sample was digested with XbaI or XhoI before separation by agarose gel, depurination by HCl, neutralization, and transfer to Zetaprobe membrane (Bio-Rad, Hercules, Calif.) by capillary blotting. The membrane was fixed by UV irradiation in a Stratalinker (Stratagene, La Jolla, Calif.). A probe was prepared in accordance with PCR DIG Probe Synthesis Kit (Roche Diagnostics, Indianapolis, Ind.) protocol using sNV-forward and sNV-reverse, which are internal primers to the psNV110 T-DNA (sequences described above). The blot was hybridized with the probe at 45° C. overnight in pre-warmed DIG easy-hyb solution. The membrane was quantitatively imaged with a phosphorimager.

Figure 6:
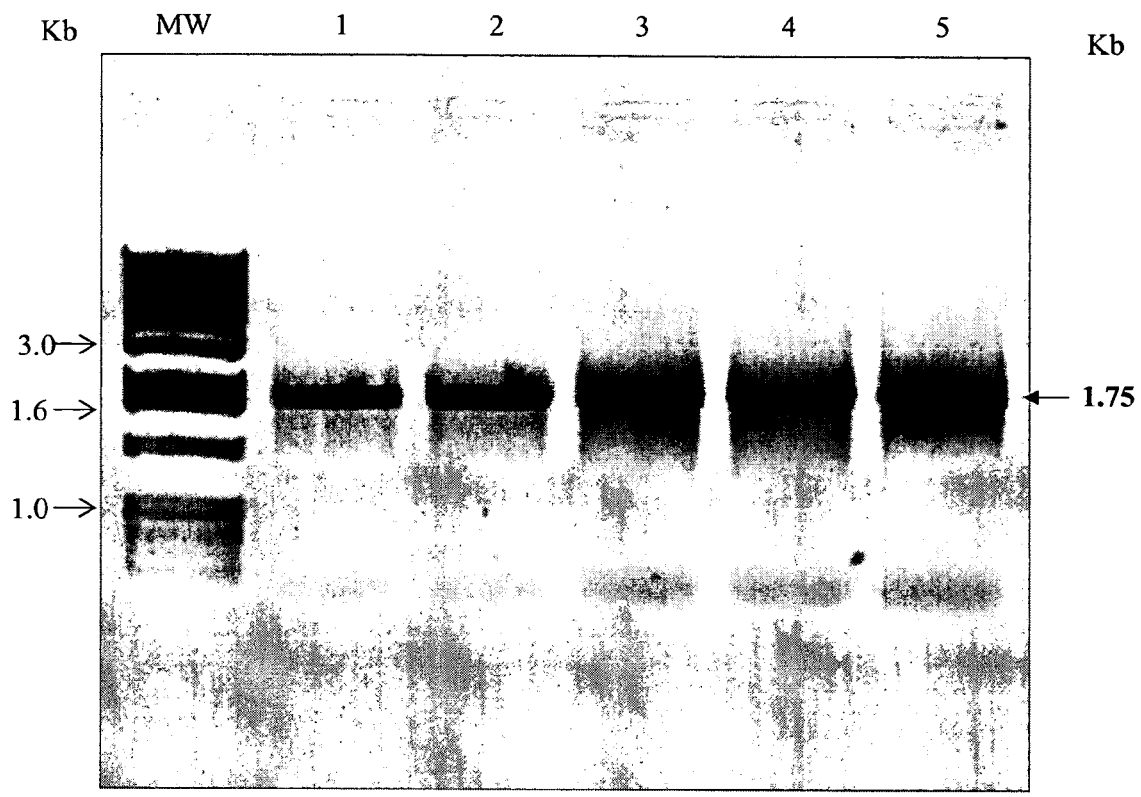
FIG. 6 is an electrophoresis gel showing PCR product obtained from isolated tomato plant leaf DNA. PCR was performed on 5 DNA samples (lanes 1-5) isolated from sNV110-2 tomato leaves. The PCR product from TEV and VspB primers was analyzed by gel electrophoresis. The expected TEV and NVCP fragment size is approximately 1750 base pairs, confirming the integration of the sNVCP gene in the tomato line sNVCP110-2.

FIG. 6 shows the resulting pattern of hybridization, as well as an aligned Coomassie blue stain of the gel that shows the molecular marker used to determine the size of the probed fragments. Each digest resulted in a fragment internal to the T-DNA cassette that hybridized to the probe. The positive control is comprised of plasmid DNA from psNV110 cut with XbaI yielding a 14,125 Kb fragment.

Example 8

Northern Blot of Fruit RNA

Expression of NVCP RNA for the clones was analyzed by northern blot analysis. RNA extraction from leaf was performed using TRIzol reagent (Gibco-BRL, Gaithersburg, Md.) in accordance with Gibco-BRL protocol. Total RNA from potato tubers was isolated by a modified phenol/chloroform method. For total RNA extraction from fruit, fruit was added (0.1 g) to 1.0 ml of TRIzol reagent and homogenized in a FastPrep machine for 30 seconds at a speed of 5 (2×). Samples were incubated at room temperature for 5 minutes to ensure complete dissociation of nucleoprotein complex. Phase separation was accomplished using chloroform (1:6) and hand shaking for 15 seconds and incubation at room temperature for 3 minutes. Samples were then spun at 12,000 g for 15 minutes at 4° C. The upper aqueous phase was removed for RNA precipitation. Isopropanol was added (1:3) and incubated at room temperature for 10 minutes to precipitate RNA. The samples were then centrifuged at 12,000 g for 10 minutes at 4° C. The supernatant was removed and the RNA pellet washed with 75% ETOH, vortexed to mix, and centrifuged at 7,500 g for 5 minutes at 4° C. After drying the RNA was resuspended in RNase-free water.

The gel case used was treated with 2% SDS for 30 minutes at 68° C. and rinsed with sterile water. The RNA samples were incubated in denaturing buffer for 15 minutes at 65° C. and run in a 1% gel with MOPS added as the agarose cooled down (80V for 2 hours). The gel was transferred to a Zeta Probe membrane and UV crosslinked to the membrane. The membrane was methylene stained and scanned. DIG Easy Hyb was used for prehybridization. The PCR probe was prepared using primers sNV-forward and sNV-reverse (described above), denatured, and added to prewarmed DIG Easy Hyb solution. Hybridization with the probe was continued overnight. The membrane was then washed in 2×SSC: 0.1% SDS (2×15 minutes at room temperature), 0.5×SSC:0.1% SDS (2×15 minutes at 68° C.), and finally in 0.1×SSC:0.1% SDS (2×15 minutes at 68° C.). The membrane was blocked with blocking solution for 1 hour at room temperature. Anti-DIG-AP was incubated with the membrane for use in chemiluminescent detection by CDP-star. After washing the membrane, detecting buffer was added along with CDP-star reagent and the membrane exposed to film. The northern blot results from fruit and leaf RNA can be seen in FIG. 8 and FIG. 9, respectively. The images depict the film exposure of the membrane above the methylene blue stain which shows the molecular markers used to determine the size of probed fragments. Synthetic gene NV samples were run along with native gene NV samples to compare the size of probed fragments, which are the same size (1.9 Kbp) for both synthetic and native NV. This shows that the sNV110 plants are expressing NVCP RNA of the expected size yielded by native NV.

Example 9

Fruit Antigen Extraction Procedure

Figure 13:
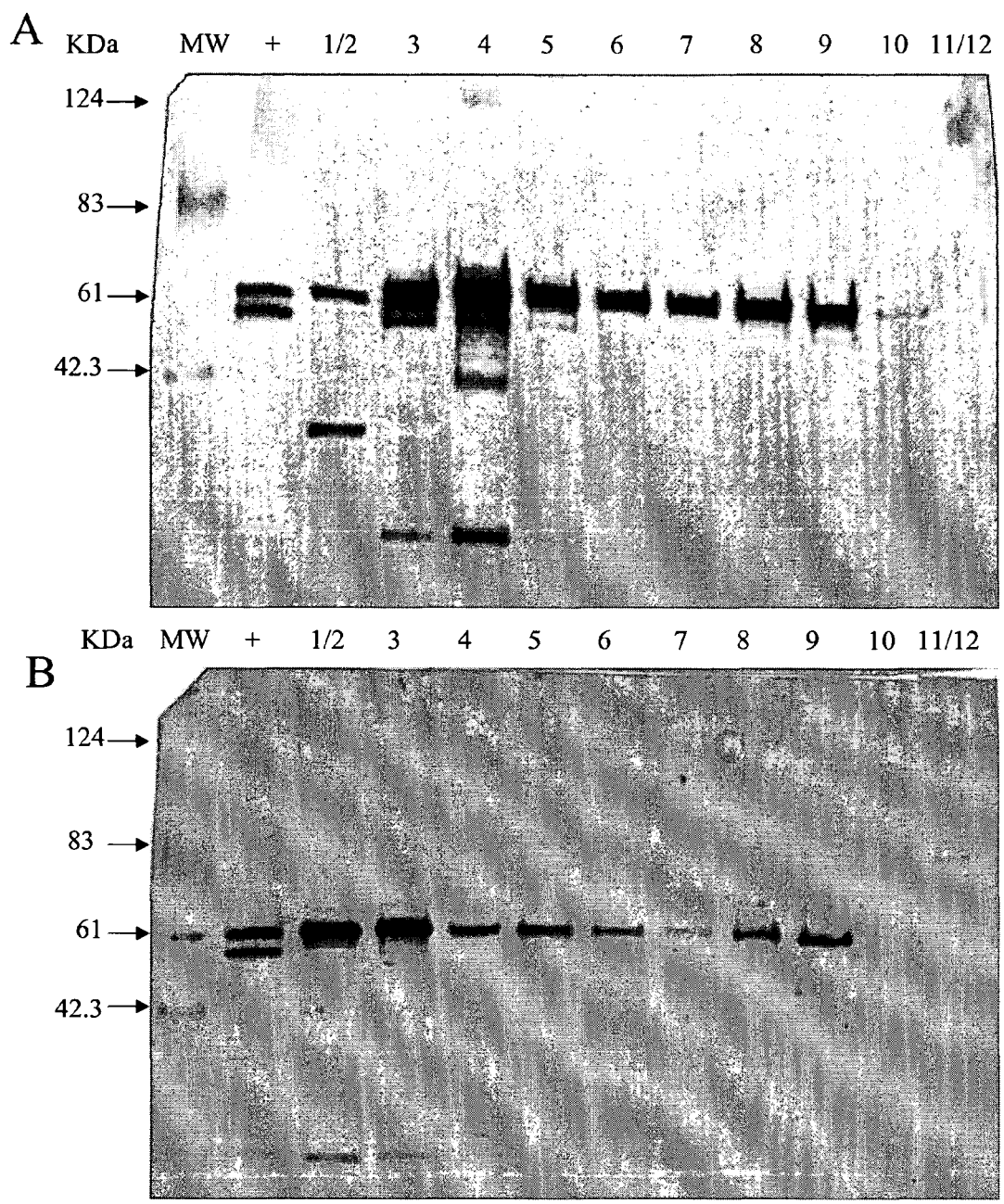
Figure 14:
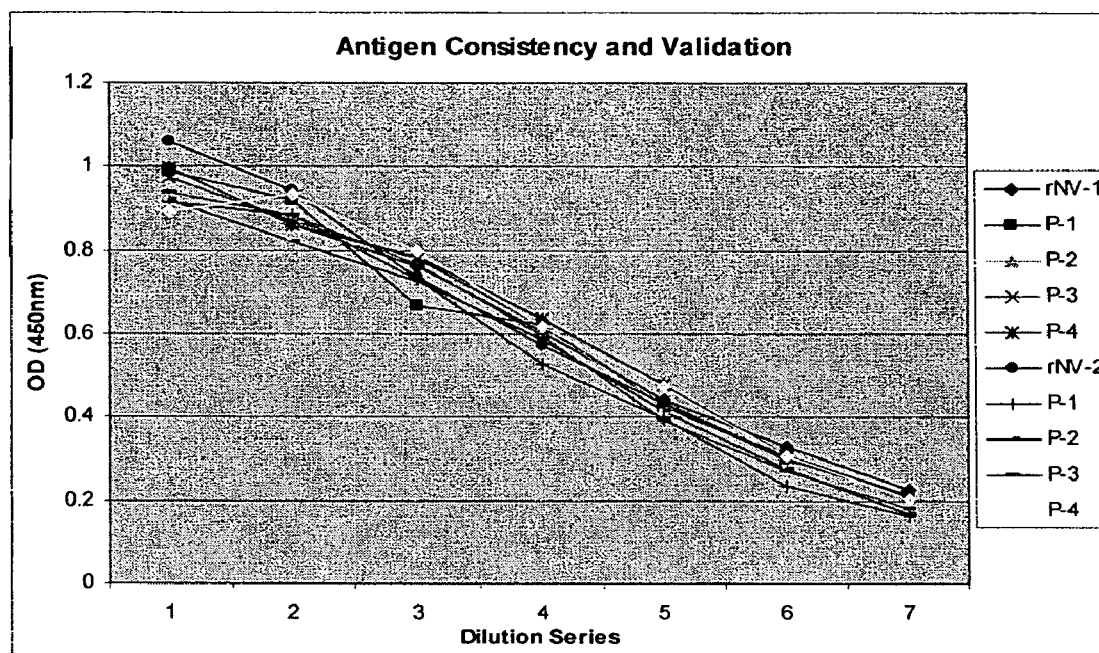

Antigen was extracted using 0.2 g of freeze dried fruit per FastPrep sample tube. 800 ul of ice cold (4° C.) PBS extraction buffer containing PBS was added and homogenized in a FastPrep machine for 30 seconds at speed 4. The extract was centrifuged at 14,000 g for 3 minutes at room temperature and the supernatant removed and kept on ice while being analyzed.

Example 10

NVCP Specific ELISA

Leaves and tomato fruit from 5 clonally propagated plants containing the synthetic NVCP gene sequence were analyzed for NVCP antigen expression by quantitative ELISA. Leaves from 5 clonally propagated plants containing the wild type NVCP gene sequence were also analyzed in parallel to confirm that expression of the synthetic gene resulted in higher antigen concentrations. Corning Costar 96 well high binding plates (or 96-well polyvinylchloride microtiter plates from Matrix) were used for the ELISA assay. Each well was coated with 100 ul of the capture antibody, rabbit anti-rNV, diluted 1:10,000 in PBS and incubated for 2 hours at room temperature. After washing the plate 3 times with PBS with 0.05% Tween 20 (PBST), the wells were blocked with 300 ul of 5% dry milk in PBST, and incubated at room temperature overnight. The plate was then washed 3 times with PBS. An r-NV standard curve was obtained by evaluating 50 ul of r-NV VLPs (1:7800 dilution from 4 mg/ml master stock) diluted with PBST within the range of 512 ng/ml to 0.5 ng/ml. 50 ul samples of freeze dried fruit extract were added to the plate in 2-fold serial dilutions ranging from 1:20 to 1:2560 for optimal detection and comparison to the reference antigen. The plate was incubated for 2 hours at room temperature and washed 3 times with PBST. Guinea Pig anti r-NV was used as the primary antibody, with 50 ul added to each well at dilution of 1:1000 in PBST, incubated for 2 hours at 37° C., and then washed with PBST. Goat anti-Guinea Pig IgG-HRP was used as the secondary antibody with 50 ul added to all wells at a concentration of 1:5000 in PBST, incubated for 2 hours at room temperature and washed 3 times with PBST. TMB substrate solution A and B were mixed in ratio of 1:9 respectively and 50 ul added to each well. TMB reacts with the IgG-HRP complex bound, via antibody, to the plate producing a blue hue. Color development was allowed to continue for approximately 7-10 minutes. 1N $H_2SO_4$ was added to stop the color reaction, and the O.D 450 nm of the plate was read. A standard curve was constructed and sample rNV concentrations were calculated. Total soluble protein (TSP) was measured by the Bradford dye-binding procedure (Bio-Rad, Hercules, Calif.).

Example 11

Antigen Stability and Variability Data

As shown in FIG. 14, processing and development with powdered tomato material demonstrated no significant decrease in antigen activity when stored at ambient temperatures for periods up to twelve months. Transgenic tomato fruit, line sNV110-2-4, expressing NVCP under a constitutive plant promoter were grown and processed as described herein above. Four capsules, designated P-1 to P-4 in FIG. 14, were randomly selected 1-year after packaging and storage at room temperature, and evaluated by NVCP-specific ELISA to determine antigen content and batch consistency. The reference antigen concentration correlates very closely to the OD readings obtained for the plant materials, providing further support for the accuracy of the calculated concentration. All dilution points were plotted on a scatter gram, and the Co-efficient of Determination (r-squared value) was found to be 0.9724, indicating high statistical confidence that batch consistency had been obtained.

Example 12

Virus-Like Particle (VLP) Content by Sucrose Gradient

Protein extracts from sNV110 freeze dried fruit were examined by sucrose gradient centrifugation to determine the proportion of NVCP monomers aggregated as VLPs (similar methods described in Mason et al., "Expression of Hepatitis B Surface Antigen in Transgenic Plants," *Proc Natl Acad Sci USA* 89:11745-11749 (1992), which is hereby incorporated by reference in its entirety). A crude extract of freeze dried fruit was obtained as described above, and the 14,000 g supernatant was layered onto a 1-50% continuous sucrose gradient. The gradient was centrifuged in the Beckman SW41 rotor at 28,000 rpm for 4 hours at 4° C., then 20,000 rpm for 14 hours at 4° C. and 12 separate fractions were collected. ELISA for NVCP was performed as described above, the density of each fraction was measured with a refractometer, and the crude O.D. 450 nm was plotted against the fraction number of the sample. FIG. 12 shows the profile obtained. For comparison, rNV VLPs were prepared as a positive control, run through a 1-50% sucrose gradient, and fractionated at the same time. The comparison shows a similar pattern between the sNV110 extract and the positive control rNV VLPs.

Example 13

Western Blot Analysis

A western blot analysis was performed on the fractions obtained from the sucrose gradient. Each fraction from the sNV110 extract was electrophoresed on 4-20% gradient polyacrylamide gels, and positive control rNV fractions were run on a second gel (run at 40 mA for 2 hours). 100 ng of rNV was run in one lane of each gel as a positive control. The molecular marker used was Bio-Rad's Kaleidoscope Prestained protein standard (Bio-Rad, Hercules, Calif.). The gels were transferred to polyvinylidene difluoride (PVDF) membranes (Amersham Pharmacia, Piscataway, N.J.) via gel-tanker transfer, and blotted in 5% dry milk overnight at 4° C. The first antibody, rabbit anti-rNV at a dilution of 1:3000 in 1% BLOTTO was incubated with the membranes for 2 hours, and the membranes then washed with PBST. Hybridization with the second antibody, goat anti-rabbit IgG conjugated with horseradish peroxidase (HRP), at 1:10,000 in 1% BLOTTO, was performed for 2 hours, and the membranes washed in PBST. The membranes were developed by chemiluminescence using ECL plus detection reagent (Amersham Pharmacia, Piscataway, N.J.) following manufacturer's protocol, and the signals were detected with Molecular Dynamics 'Storm' system and quantified with IMAGEQUANT software. The resulting images are seen in FIGS. 13A-B. The sNV110 fractions are depicted in FIG. 13A, and the rNV fractions are shown in FIG. 13B. The positive control yielded bands of approximately 61 kDa as did the fractions for both the test and positive control extracts. The intensity of the band corresponds to a higher segregation of VLPs in that fraction.

Example 14

Creation of sNV Powder from Freeze Dried Fruit

Grinding of lyophilized sNV110 and TA234 control fruit into fine powder was performed in a fume hood. The food grade metal sifter, used to reduce the freeze dried fruit to powder, was soaked in 10% bleach for 10 minutes and allowed to dry. Control fruit was processed first to avoid contamination. The freeze dried fruit was removed from heat sealed bags and hand ground, by grating against the sifter's screen into a large Ziploc bag. Any material that would not pass through the screen was autoclaved and disposed of. The sifter was then soaked again in 10% bleach and allowed to dry before processing the transgenic sNV110 fruit. The same process was followed and the resulting powder stored in a large Ziploc bag.

Example 15

Packaging of Control and Antigenic Powder into Gelatin Capsules

Gelatin capsules were chosen as the vehicle for administering the antigenic dose to human subjects. Size "00" capsules were chosen based on their volume versus ease of ingestion. FDA approved "00" capsules were provided by Nutracentical (Park City, Utah). All non-sterile equipment was soaked in 10% bleach for 10 minutes and air dried (i.e., Cap-m-Quik capsule filler), and the entire process was performed in a fume hood. Control capsules were packaged first according to Cap-m-Quik capsule filler directions. Deviations from the instructions include: filling the larger bottom portion of the capsule in one machine by filling and tamping exactly 10 times; and using another machine to fill the smaller cap portion by filling and tamping only 1 time. Capsules were then assembled and cleaned of any residual powder by placing them into the above mentioned sifter and passing air over them. The capsules were placed into pre-labeled, USDA approved bags (20/bag) and heat sealed. Label information includes: type of capsule (control, NVCP transgenic, or 1% *Quillaja*-enhanced); lot number; number of capsules; date of manufacture; date of packaging; and location of manufacture. The capsule filler was soaked in 10% bleach for 10 minutes before packaging the transgenic material. The same process was used for the NVCP transgenic material and the capsule filler washed before packaging the transgenic material enhanced with 1% QS extract. Formulating the NVCP powder with *Quillaja* was accomplished by adding 1% *Quillaja* to an amount of NVCP powder and sifting the two together to break up any clumps. The substances were mixed thoroughly in a heat sealed bag by repeated inversion for 15 minutes. Once the capsules were packed and cleaned off, 40 of each type were weighed to determine the variability amongst the capsules. Table 2, below, is a summary of the variability.

TABLE 2

| | Control Capsules | NVCP Capsules | 1% Quillaja |
|---|---|---|---|
| Range | 0.411 g-0.524 g | 0.462 g-0.584 g | 0.432 g-0.582 g |
| Median | 0.464 g | 0.508 g | 0.510 g |
| Average | 0.466 g | 0.511 g | 0.513 g |

The selectable marker that is used to produce tomato transformants is the bacterial neomycin phosphotransferase protein (NPTII). The *E. coli* derived NPTII was shown to be biochemically equivalent to plant expressed NPTII (Fuchs et al., "Purification and Characterization of Microbially Expressed Neomycin Phosphotransferase II (NPTII) Protein and Its Equivalence to the Plant Expressed Protein," *Biotechnology* 11(13): 1537-42 (1992), which is hereby incorporated by reference in its entirety). The *E. coli* derived NPTII degrades rapidly under conditions of simulated mammalian digestion and was shown to cause no deleterious effects when purified protein was fed to mice at up to 5 g/kg body weight (Fuchs et al., "Safety Assessment of the Neomycin Phosphotransferase II (NPTII) Protein," *Biotechnology* 11 (13): 1543-7(1993); which is hereby incorporated by reference in its entirety). The FDA has amended the food additive regulations to provide for the safe use of NPTII as a processing aid in the development of new varieties of plants including tomato, oilseed rape, and cotton. (21 CFR 573.130). The environmental impact of kanamycin genes introduced into transgenic plants on a large scale has been assessed (Nap et al., "Biosafety of Kanamycin-Resistant Transgenic Plants," *Transgenic Research* 1(6):239-249 (1992), which is hereby incorporated by reference in its entirety). A plant acquiring this gene would not have selective advantage and no harmful effect of the gene product for human or animal consumption should be evident. In particular, the use of kanamycin in human clinical practice has been superseded by other treatments due to widespread bacterial resistance to the antibiotic. Flavell et al., "Selectable Marker Genes: Safe for Plants?" *Biotechnology* 10(2):141-4 (1992) (which is hereby incorporated by reference in its entirety), reviewed the safety concerns and likely environmental risk of using the NPTII gene and concluded that, in their view, there were risks neither to humans nor the environment.

*Quillaja* (*Quillaja saponaria*) is an extract of soapbark and is used commercially as an anti-foaming agent and emulsifier in the food industry. The major food use is in soft drinks. Moreover, *Quillaja* is reported to be an effective oral adjuvant (WO 0117555 to Hamilton et al.; Walmsley et al., "Passive Immunization of Mice Pups Through Oral Immunization of Dams with a Plant-Derived Vaccine," *Immunol Lett* 86(21): 71-76 (2003), which are hereby incorporated by reference in their entirety), and has shown significant enhancement of immunogenicity in animal model studies, as shown in FIG.

15. *Quillaja* extracts are currently proposed for use in the Codex draft General Standard for Food additives (GCA) at 500 mg/kg in water-based flavored soft drinks. *Quillaja* is also approved for use in food and beverages by the United States FDA under title 21 CFR 172.510, and bears FEMS number 2973. The crude extract is toxic for human consumption in large amounts. However, "large amounts" has yet to be determined for humans. Powdered *Quillaja* bark or saponin concentrate has highly local irritant and stimulatory properties. It also possesses depressant activity on the heart and respiration. Severe toxic effects due to large oral doses have been reported to be liver damage, respiratory failure, gastric pain, diarrhea, haemolysis of red blood corpuscles, convulsions, and coma (Leung et al., "Hyperphagia After Ventral Tegmental Lesions and Food Intake Responses of Rats Fed Disproportionate Amounts of Dietary Amino Acids," *Physiol Behavior* 25(3):457-64 (1980), which is hereby incorporated by reference in its entirety). Efimova et al., "Effect of Saponins of the Pericarp of *Sapindus mukorossi* G. on the Blood Pressure and Cholesterol in Animals," *Farm Zh.* 21(6): 45-9 (1966), (which is hereby incorporated by reference in its entirety) reports a mouse oral LD50 value of 1.6 g/kg body weight. Toxicity of the food grade extract of QS has limited its use as a parenteral adjuvant. However, this toxicity appears to be abated when delivered orally. The JECFA (Joint Expert Committee on Food Additives) has established the human ADI of 0-5 mg/kg bodyweight for unpurified (food grade) extract. 1% *Quillaja* was used in the adjuvant enhanced capsules with approximately 312-462 mg of powder per capsule. Using a safe estimation of 20 capsules per dose, the amount of *Quillaja* ingested is 62-92 mg per dose. For a 150 pound person (68 kg) this equates to about 27% of the JECFA established ADI. The *Quillaja* extract used as described herein was prepared by Garuda International (Lemon Cove, Calif.).

Example 16

Pharmacology Considerations

NVCP Transgenic Potato Vaccine, Oral—Previous Human Clinical Experience: In 1999 transgenic potato containing NVCP was evaluated in human clinical trial at the University of Maryland, Baltimore (Center for Vaccine Development). The complete results of that trial are summarized by Tacket et al., "Human Immune Responses to a Novel Norwalk Virus Vaccine Delivered in Transgenic Potatoes," *J. Infectious Diseases* 182:302-305 (2000) (which is hereby incorporated by reference in its entirety). In summary, no major toxicological events were recorded, 95% of volunteers developed significant increases in IgA secreting cells, 20% of volunteers developed specific serum IgG, and 30% of volunteers developed specific stool IgA. Volunteers received either 2 or 3 oral doses of vaccine, with each dose consisting of 150 grams of raw, peeled, diced potato containing an estimated range of 215-751 ug NVCP per dose. Overall, 19 out of 20 volunteers developed an NVCP-specific immune response of some kind. Additional preclinical safety and efficacy data is available within Department of Health and Human Services, Protocol No. 98-029, BB-IND #8118; "Immunogenicity of Recombinant Norwalk Virus Capsid Protein Delivered in Transgenic Potatoes" which is hereby incorporated by reference in its entirety). Major improvements in potency (evaluated in mice model system) have been achieved since this trial, by utilizing transgenic tomato materials, and by exploiting a plant-optimized gene sequence for NVCP expression as described herein above. Demonstration of improved preclinical efficacy is described below.

Figure 15:
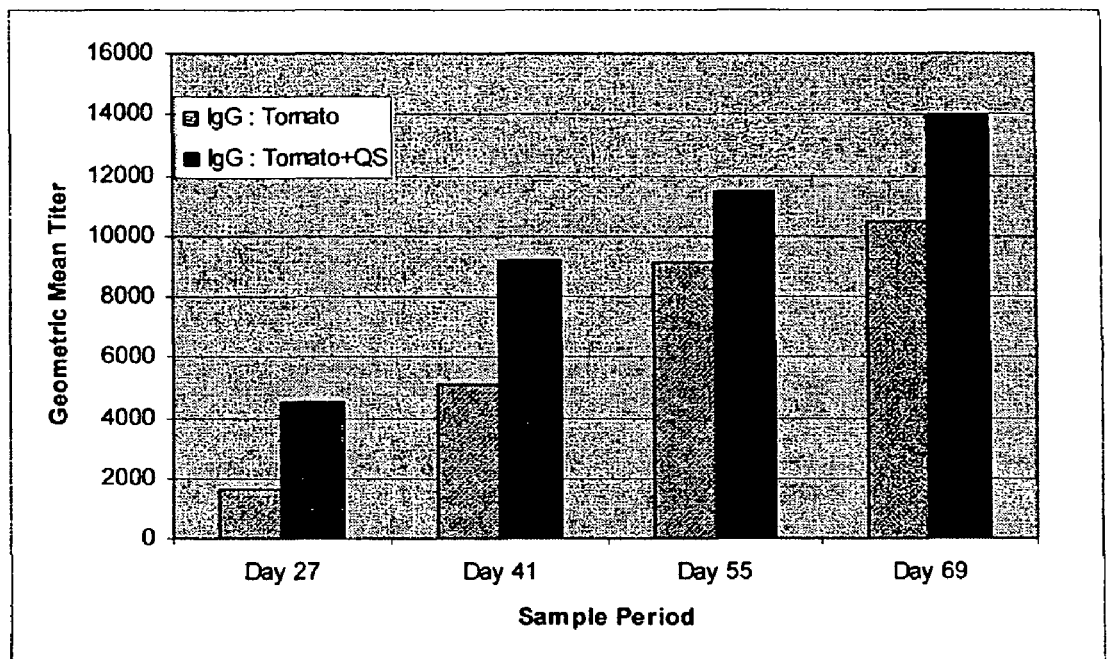
Figure 16:
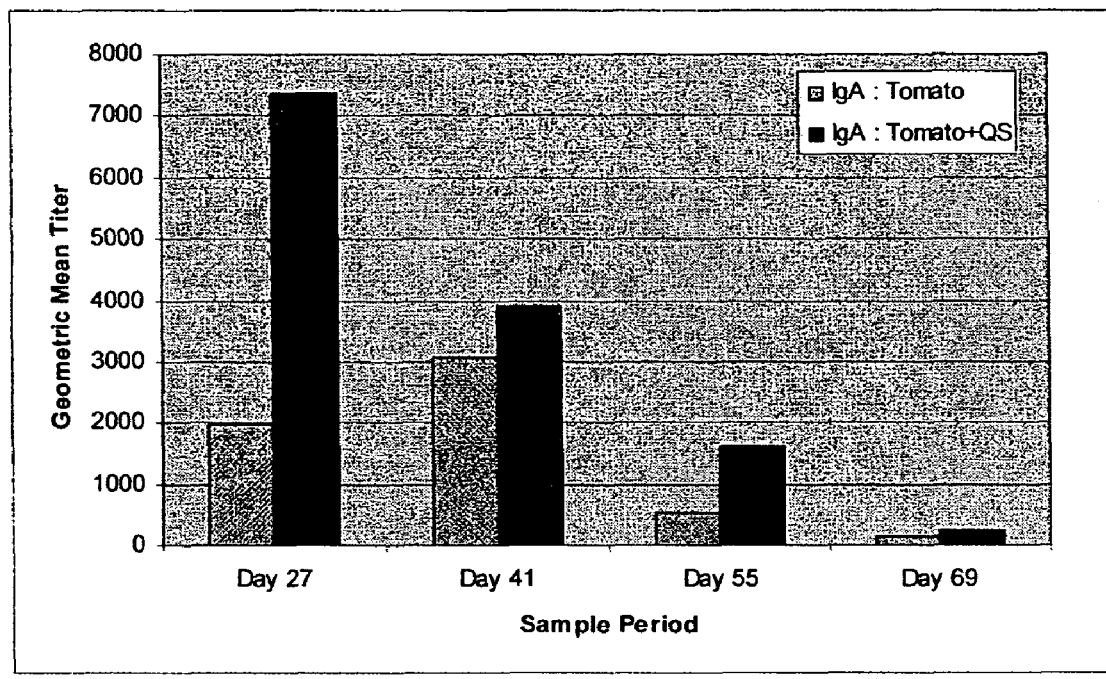
Figure 19:
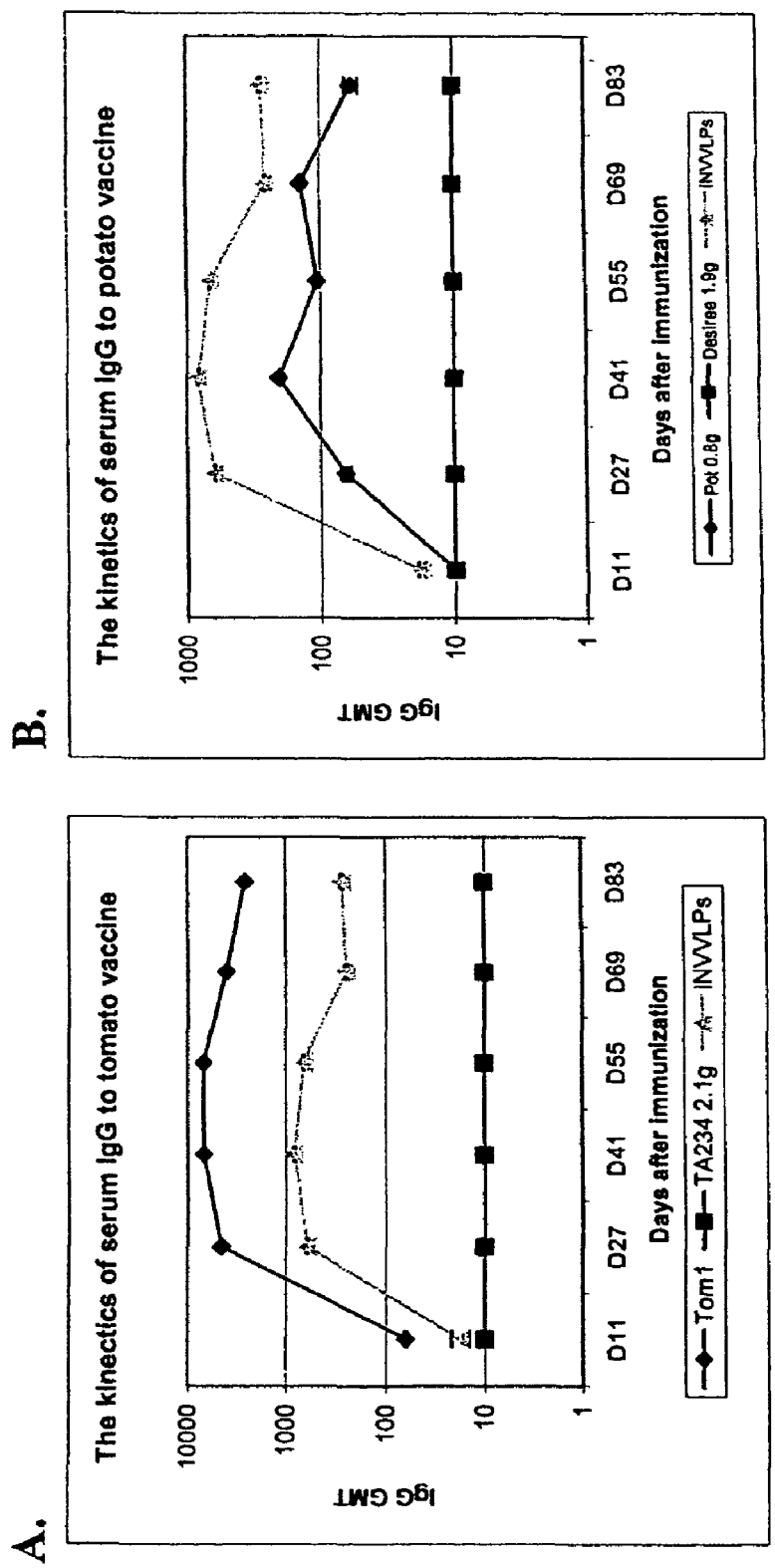

Transgenic tomato materials expressing the native gene sequence for NVCP (SEQ ID NO: 1) were created by methods similar to those described above. The elite lines were selected on the basis on NVCP detection in mature fruit and propagated for batch production. Powdered fruit materials were utilized in mice model feeding studies. No adverse effects were recorded, and resultant immune responses were significant, as shown in FIG. 15 (IgG response) and FIG. 16 (IgA response). Table 3 and Table 4, below, provide individual mice titers, and clearly indicate which animals were considered as non-responders. Six out of the ten mice who were fed transgenic tomato powder developed both IgG and IgA significant responses specific to NVCP. IgG titers specific for anti-NVCP were not shown to have reached plateau even 48 days after the final dose was provided. Experimental groups were given NVCP tomato powder formulated with 0.33% QS extract demonstrated significantly higher IgA responses at all time points. While the QS extract did not have any significant effect on IgG responses, the data trend indicates that adjuvanted animals developed IgG titers faster. Without serological data beyond day 69, it is difficult to speculate whether either group may have eventually shown a higher peak in their titer or whether such titers may possibly have been maintained for extended duration in one group compared to the other.

TABLE 3

Serum IgG Endpoint Titers for all Mice at Day 69 (Endpoint is dilution at which $OD_{450} < 0.2$).

| NT | | NTQ | | TT | | TTQ | |
|---|---|---|---|---|---|---|---|
| MOUSE # | ENDPOINT | MOUSE # | ENDPOINT | MOUSE # | ENDPOINT | MOUSE # | ENDPOINT |
| 1 | 113 | 6 | 37 | 11 | 11 | 16 | 131 |
| 2 | 92 | 7 | 182 | 12 | 21162 | 17 | 30 |
| 3 | 70 | 8 | 79 | 13 | 2071 | 18 | 28272 |
| 4 | 175 | 9 | 61 | 14 | 65 | 19 | 21365 |
| 5 | 60 | 10 | 60 | 15 | 26083 | 20 | 4479 |

TABLE 4

Fecal IgA Endpoint Titers for all Mice at Day 69 (Endpoint is dilution at which $OD_{450} < 0.2$)

| NT | | NTQ | | TT | | TTQ | |
|---|---|---|---|---|---|---|---|
| MOUSE # | ENDPOINT | MOUSE # | ENDPOINT | MOUSE # | ENDPOINT | MOUSE # | ENDPOINT |
| 1 | 4 | 6 | 2 | 11 | 9 | 16 | 0 |
| 2 | 1 | 7 | 30 | 12 | 108 | 17 | 1 |
| 3 | 18 | 8 | 8 | 13 | 97 | 18 | 655 |
| 4 | 0 | 9 | 32 | 14 | 6 | 19 | 629 |
| 5 | 0 | 10 | 11 | 15 | 297 | 20 | 29 |

Transgenic tomato and potato materials expressing the plant-optimized (synthetic) gene sequences (SEQ ID NO: 3) for NVCP were created as described herein above. The elite tomato line sNV110-2 (harboring the transgenic synthetic gene having SEQ ID NO: 3) was propagated for batch production, along with the best expressing transgenic potato line. Mice feeding trials evaluated powdered materials from both sources. FIGS. 17A-B compare the immune responses in mice fed transgenic potato, tomato, non-transgenic material or a recombinant positive control NVCP antigen (baculovirus source). In each case where transgenic plant material was provided, doses of 1.5, 2.5 or 5 grams were provided to the mice for consumption. Even though 3 out of 5 mice responded to sNVCP potato, the average IgG response (shown as OD reading) per experimental group is low in comparison to rNV, or in comparison to the transgenic tomato group. FIG. 17A depicts the relative immune response in all 5 mice responding to transgenic tomato, with the rNV titers shown on both figures for cross-reference. These data indicate that, at least in a mice model system, transgenic tomato powder is highly potent in comparison to potato materials and at least as effective as positive control rNV VLPs (derived from baculovirus expression system). No adjuvants were used in this study.

FIGS. 18A-B and 19A-B depict the immunoglobulin kinetics displayed by each group up to day 83, and illustrate 1-2 orders of magnitude difference between immunogenicity obtained from equal volumes of NVCP tomato compared to NVCP potato.

Example 17 sNVCP Gene Enhanced mRNA and Protein Accumulation

The sNVCP gene having SEQ ID NO: 3 was inserted in psNV110 as described above, while native NVCP was inserted into pNV110. Plasmids pNV110 and psNV110, shown in FIG. 2B, were used to transform tomato and potato plants. For tomato transformation, 74 and 24 independent positive tissue-culture plantlets were obtained by ELISA screening for NV110 and sNV110 constructs, respectively. For potato, 57 and 36 positive lines were obtained for NV110 and sNV110 constructs, respectively. The 5 elite tomato lines (T1 generation) and 10 potato lines (T0 generation) for each construct were grown in soil in the greenhouse to allow comparison of their expression performance in adult stages. The synthetic NVCP gene allowed 4-fold higher mRNA and rNV accumulation in both tomato (p=0.0002, t-test), as shown in FIGS. 20A-B, and potato plants (p=0.0000, t-test), as shown in FIGS. 20C-D). The slopes of the regression scatters (NVCP antigen levels vs. mRNA abundance) were similar for NV110 and sNV110 constructs, indicating that more stable transcript accumulation in sNV110 lines was a key factor for the higher accumulation of NVCP protein in both plants. The maximum rNV level in sNV110 lines were up to 8% of the total soluble protein (TSP) in tomato fruit and 0.4% in potato tubers. The elite tomato line sNV110-2 contained one and potato line sNV110-43 contained one and two copies of sNV gene, as determined by Southern blot.

Example 18

Assembly of Virus-Like Particles

The proportion of NVCP that was assembled as VLPs was estimated by sucrose gradient sedimentation and by comparing a VLP standard, which was produced in insect cells and purified by 30% sucrose cushion and following by gradient sedimentation. The VLP standard showed 2 peaks, with the faster-sedimenting material (38 nm) more abundant, as shown in FIG. 21A, which is consistent with two VLP forms observed in the insect cell-derived rNV (White et al., "Biochemical Characterization of a Smaller Form of Recombinant Norwalk Virus Capsids Assembled in Insect Cells," *J Virol* 71:8066-8072 (1997), which is hereby incorporated by reference in its entirety). By calculating the proportion of the total ELISA or immunoblotting-positive materials that cosedimented with the higher peaker of VLP standard (38 nm), it was found that the percentage of VLPs (38 nm) varied from 23% to 41% in fresh tomato fruit and from 42% to 58% in potato tubers, as shown in FIG. 21A. To determine if rNV accumulation levels affected VLP assembly efficiency, protein crude extracts were analyzed from tomato fruit with different rNV expression levels by sucrose gradient and ELISA, and no significant differences were found among lines. Also compared were VLP proportions in fresh, freeze-dried, and air-dried materials, and freeze-drying and air-drying processing did not affect VLP stability in either tomato or potato plants. Further analysis of VLPs by negative staining and IEM revealed that rNV VLPs from tomato fruit and potato tubers, which cosedimented with higher-peak of insect cell-derived VLPs were about 38 m and resembled i-rNV in both size and appearance, as shown in FIGS. 21B-D.

Of further interest were the peak fractions near the top of the gradient, which were believed to be soluble protein and small oligomers. Fractions 3 to 5 were pooled and examined by negative staining and IEM. It was found that there were large amounts of smaller particles (around 23 nm) in these portions, shown in FIG. 21C. Taking into consideration that many oligomers existed in the same sucrose gradient fractions, it was only roughly estimated that 25-40% of the material in fractions 3-5 were 38 nm particles in tomato extracts. Further analysis with IEM (immune electron microscopy) demonstrated that those particles, as were 38 nm particles, were able to be aggregated by rNV-specific antibody, as shown in FIG. 21F and FIG. 21G, which are characteristic of the IEM technique (Hardy et al., "Antigenic Mapping of the Recombinant Norwalk Virus Capsid Protein Using Monoclonal Antibodies," *Virology* 217:252-261 (1996), which is hereby incorporated by reference in its entirety). Microscopic examination of extracts of nontransgenic materials did not reveal the particles, seen in FIG. 21E, and particle clumping by IEM.

IEM was carried out as follows. A 10 µl drop of the sample was applied to a parafilm sheet, and a formvar/carbon-coated grid (300 mesh) was set on the drop for 15 s or on/off. Excess liquid was absorbed from the side of the grid with a filter paper. Then the grid was placed on a drop of 2% aqueous uranyl acetate for 15 s, and excess fluid was blotted as before. After air drying, the grid was examined on a Tecnai 12 Biotwin transmission electron microscope (FEI Company, Eindhoven, The Netherlands). For IEM, antibody was treated as follows to remove non-specific binding activity. Non-transgenic lyophilized tomato powder was homogenized with the protein extracting buffer by a Fastprep FP120 (Bio 101), and briefly pelleted by microcentrifugation. The pellet was resuspended with an equal volume of rabbit anti-rNV, and incubated for 1 hr on ice. The mixture was centrifuged for 3 min at 12,000×g at 4° C. to give an antibody supernatant, which pre-absorbed with fresh nontransgenic pellet 3 more times. IEM was performed as follows. Grids carrying samples were saturated with TBST with 1% fish gelatin (pH 8) for 20 min before incubation with the pre-absorbed primary antibody for 1 h at room temperature. The grids were washed in 5× strength TBST buffer, 3 times for 5 min each, then rinsed in normal TBST buffer, 5 times at 2 min each, and then incubated with gold-affinipure goat anti-rabbit IgG (H+L) (Jackson Immune Research, West Baltimore, Pa.) for 1 h. After incubation, the grids were washed three times, 5 min each, and then fixed for 10 minutes in 2.5% glutaraldehyde in 0.1M sodium cacodylate buffer (pH 8), and followed by three more washing by using the same buffer above, 5 min each, and 10 times rinse with distilled water, 1 min each. Alternatively, TBST buffer with pH 6.5 and PBS buffer to saturate and wash Grids were used. Afterwards, the grids were treated as for regular negative staining and EM.

Example 19

Oral Immunogenicity of Tomato and Potato Expressing Native NVCP Gene

In preliminary experiments with transgenic plants expressing native NVCP gene, BALB/c/C mice were each fed 4 doses of 4 grams tomato and potato powder on days 1, 4, 17, and 20. Sixty percent of mice immunized with tomato powder elicited an immune response with peaks of IgG and IgA GMTs reaching 580 and 184, respectively, while none of the mice showed immune responses to potato powder. This experiment was limited by the rNV amount produced in plant materials (tomato and potato powder contained only 31 and 11 μg/g dry weight, respectively) and the actual amount of materials that mice ingested in 16 h, because the mice were able to reliably eat up to 2 grams powder overnight. In order to test if high doses of transgenic materials presented any advantage in inducing immune responses, tomato line sNV110-2 and potato line sNV110-43 were chosen, containing 160 and 120 μg/g dry weight, respectively (approximately 50 μg and 63 μg VLPs/g DW respectively, in terms of 38 nm VLP).

Example 20

Oral Immunogenicity of Transgenic Potato Expressing Synthetic NVCP Gene

Three large doses of potato powder (1.5, 2.5, or 5 gm) were fed to each mouse on days 1, 4, 17, and 20. The actual doses ingested by each mouse, were, on average, 1, 1.2, and 2 gm each feeding, containing 120, 144, and 240 (g rNV/dose, respectively, or 63, 76, and 128 μg VLPs/dose. Potato powder in two groups (2.5 or 5 gm) was reconstituted with 0.6 volume of sterile water to facilitate ingestion by mice. Nontransgenic potato 'Desiree' powder (5 gm per mouse per feed) was given to one control group (−), and 100 μg purified i-rNV VLPs were orally administered by gavage to another control group (+). Serum and fecal antibodies were measured by ELISA, and GMTs were calculated for each group of mice. All preimmune serum and fecal samples were negative (titer<20) for rNV-specific IgG and IgA, as were those of the control group (−) that received nontransgenic materials (titers<20; the lowest dilution tested). Kinetics of total rNV-specific serum IgG and intestinal IgA responses are shown in FIGS. 22A-B. No primary serum IgG was detected in three groups receiving transgenic potato at 11 days post immunization (dpi), but fecal IgA was detected at 11 dpi, with the groups that ingested 1, 1.2, or 2 grams of potato powder showing 60, 20, and 40% of mice responding, and GMTs of 49, 15, and 29, respectively. In 2-4 weeks after third (day 17) and fourth feeding (day 20), serum antibody responses were detected in all mice in the group that ingested 1 gram of powder, with IgG GMT in the 1 g group leveling off at 201 at 41 dpi. Mucosal responses increased quickly and reached at a peak in the 1 g group with IgA GMT=1293 at 27 dpi. The serum IgG responses to potato rNV were lower than those of mice that were gavaged with 100 μg iNV VLPs, but fecal IgA responses were similar. In the other two groups that received more potato materials, only 20-40% mice gave measurable antibody responses with IgG GMTs less than 36, and IgA GMTs less than 117. The data raises the question as to why more potato powder did not induce more antibody production and checked the stability of VLPs in potato materials. These were mixed with water, which resulted in potato browning due to oxidation, and it was found that the VLP proportion was dramatically decreased to 15 μg/gDW (p=0.0004, t-test), as shown in FIGS. 22 C-D. Thus, the actual doses for these groups ingesting 1.2 and 2 gram were about 18 and 30 μg VLPs/dose. This result indicated, on the other hand, that stable VLPs, instead of soluble subunits or oligomers, are essential for immune responses.

Example 21

Tomato Expressing sNVCP Induced Robust Systemic and Mucosal Immune Responses

Three doses of tomato sNV110-2 powder (1.5 gm, 2.5 gm, or 5 gm) were provided on days 1, 4, 17, and 20. The actual doses ingested by each mouse were, on average, 1.2, 1.5 and 2.2 gm each feeding, containing 192, 240, and 352 μg rNV/dose, respectively, or 60, 75, and 1101 g VLPs/dose. Nontransgenic tomato TA234 powder (5 gram per mouse per feed) were given to one control group (−), and 100 μg purified iNV VLPs were orally administered by gavage to another control group (+). Serum and fecal antibodies were measured by ELISA, and GMTs were calculated for each group of mice. All pre-immune serum and fecal samples were negative for rNV-specific IgG and IgA, as were control group (−) (titers<20; the lowest dilution tested). Kinetics of total rNV-specific serum IgG and intestinal IgA responses are shown in FIGS. 23A-B, respectively. All mice that ingested 1.2 g or more of tomato sNV110-2 powders consistently showed both primary serum and intestinal antibody responses after the first two feedings (day 11) with IgG GMTs ranging from 64 to 192, and IgA GMTs from 1718 to 2465, respectively. No significant difference (p=0.05) in primary titers was observed among groups. In contrast, for the group that was orally administered by gavage with 100 g VLPs, only 1 of 5 mice showed primary serum antibody responses with IgG GMT=18, and 2 of 5 had primary intestinal antibody responses with IgA GMT=62. These were significantly lower than groups receiving transgenic tomato powder (p<0.05). After the third (day 17) and the fourth (day 20) feeding of transgenic tomato powder, IgG titers in all groups substantially increased, then leveled off at Day 55 with IgG GMTs ranging from 6775 to 8221. The long-term IgG kinetics were monitored for the group that ingested 1.2 gram sNV110-2 powder, and it was found that their serum antibody responses were maintained at high levels (IgG GMT=2000) for at least 6 months (see booster data below). Intestinal antibody responses reached their peaks at 27 dpi with IgA GMTs ranging from 10681 to 19127. Linear regression analysis revealed that increase in IgG and IgA GMTs was closely related to doses, however, only the group that consumed 2.3 grams of sNV110-2 tomato powder consistently had significantly higher IgA GMTs than the one consuming 1.2 grams at all time points (p<0.025-0.0367), indicating 1.2 grams of sNV10-2 was sufficient for inducing robust serum antibody responses in mice. In contrast, the control i-rNV gavage group had their maximum levels of IgG GMT=826 and IgA GMT=1748, which were 8.2 and 6.2 fold less than the group that ingested 1.2 gram of sNV110-2 powder (p<0.0183). Further, long-term serum antibody responses declined to baseline in 3 months (IgG GMT=58 at 87 dpi).

Example 22

Minimum Dosages of Transgenic Tomato Required for Eliciting Immune Responses

Figure 24:
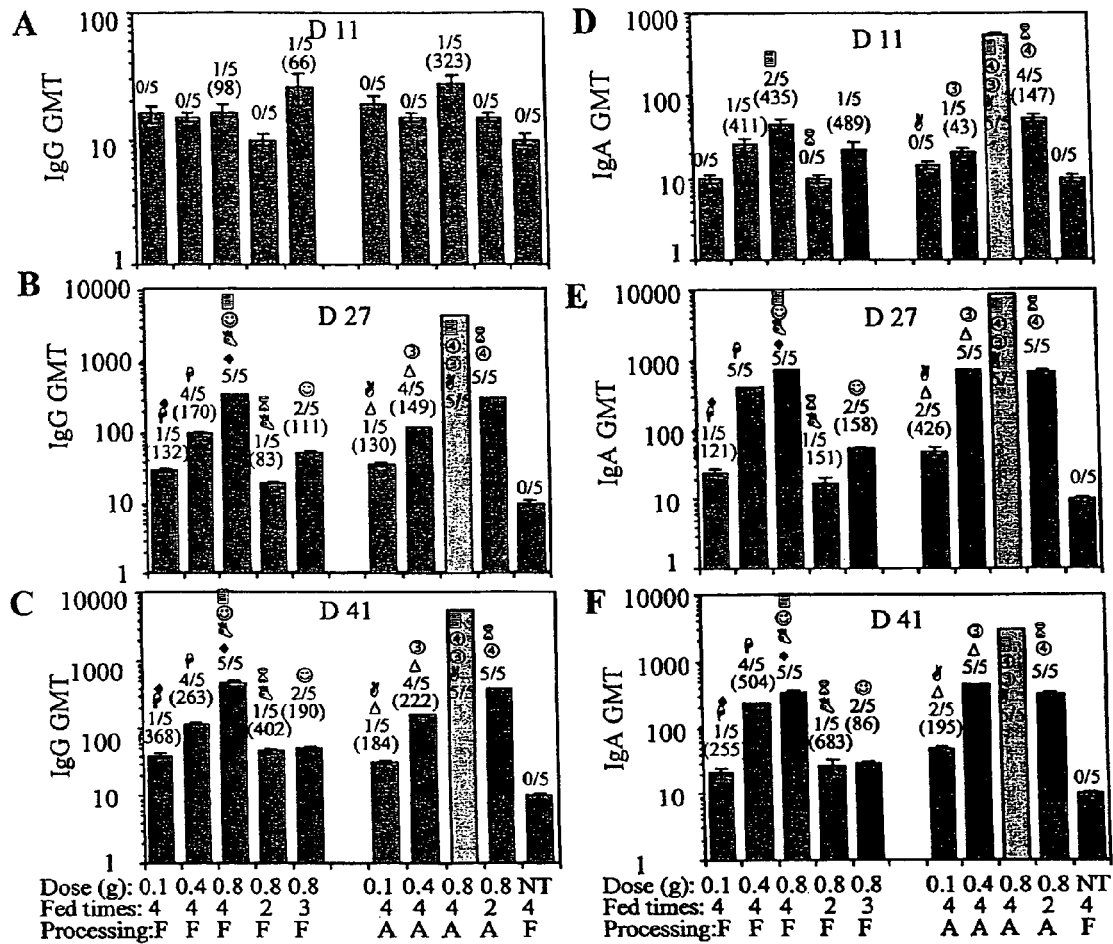
FIGS. 24A-F show the immunologic response to different doses of rNV processed in two different ways, over a time course post-immunization.

In order to determine the minimum dosage required for inducing immune responses, 3 lower doses of 0.1, 0.4, and 0.8 gram of either sNV110-2 freeze-dried tomato powder (mixed with 0.6 volume water), or air-dried fruit, were tested. A control group received non-transgenic tomato powder. The results are shown in FIGS. 24A-F. Immunization schedules were similar to the that described above except for some groups, to which only two (days 1 and 20) or three feedings (days 1, 4, and 20) of 0.8 gram of transgenic materials were given. One week after first two feedings, a positive serum antibody response was detected in 20% of mice receiving two doses of 0.8 grams of sNV110-2, either powders or air-dried fruit. Intestinal antibody responses were higher, with 20% of mice showing IgA responses with two doses of 0.4 g of sNV110-2 powder or air-dried fruit, and 40% and 100% of mice showing positive intestinal antibody responses with 0.8 g of materials, with IgA GMTs of 45 and 564, respectively. Further, no mice had detectable fecal antibody when fed with one feeding of 0.8 g of powder, but 60% of mice showed a positive response with GMT of 53 when receiving air-dried materials with the same amount of rNV or VLPs. T-test indicated there was a significant difference (p<0.036-0.047) between groups that ingested 0.8 grams of materials, indicating, at least at this dose, air-dried fruit was a more potent immunogen. At day 27, one week following two additional feedings of 0.1, 0.4 and 0.8 g of sNV110-2 powder (on days 17 and 20), 20, 80 and 100% mice showed significantly increased IgG responses with IgG GMT were 30, 117, and 350, respectively. There was a significant difference between the 0.1-gram-group and the latter two (p=0.0457 and 0.0216, Mann-Whitey test). Similar cases also were observed in three groups that ingested air-dried materials, with IgG GMTs of 36, 120, and 4487, respectively. Statistical analysis revealed that 0.8 g of air-dried fruit gave substantially enhanced serum antibody responses over 0.4 g of air-dried fruit (p<0.0122, Mann-Whitey test), and also over 0.8 g of powder (p<0.035, Mann-Whitey test). In groups that only had a total of 2 or 3-feedings of 0.8 g of sNV110-2 powders, only 20-40% of mice showed serum antibody responses with very low IgG GMTs ranging from 27 to 54. However, 100% of the group receiving 2 doses of 0.8 g of air-dried materials had IgG responses with a GMT of 314, which was significantly higher than the counterpart group receiving freeze dried powder (p<0.0122). Similar results were seen with intestinal IgA responses at day 27, as shown in FIG. 24E. All mice receiving 0.4 g or more powder, showed IgA immune responses with IgA GMTs of 397 for 0.4 g-group and 730 for 0.8 g-group. The counterparts consuming air-dried materials had IgA GMTs of 710 and 8828 each. For the doses of 0.1 gram of tomato powder or dried fruit, 20-40% of mice had IgA responses with IgA GMTs of 25 and 50, respectively. These titers were similar to those of the groups that received 2- or 3-dose of 0.8 grams powder. For the group that received two doses of 0.8 gram dried materials IgA titers were detected in all mice with GMT of 702.

The overall profiles of antibody responses among the groups at 41 dpi were similar to those at 27 dpi. Two exceptions were observed: 1) IgG and IgA GMTs continued to increase for the group receiving a total 2 doses of 0.8 g powder, indicating the recall of a immune response in this group was slow; and 2) IgA GMTs for all other groups began to decline.

Example 23

Booster Immune Responses

In order to determine if immune memory was established, and if immune tolerance was induced when mice were repeatedly exposed to VLPs, groups of five female CD1 mice were primed with two doses of tomato powder (0.1 and 1.2 g) or potato powder (1.0 g) with 10 µg VLPs each at the time indicated in the legend for FIGS. 25A-D. For the group that was primed with 0.1 g tomato powder, only 1 of 5 mice showed primary antibody responses with a peak titer of 184. At 55 dpi, the IgG GMT returned to a baseline. One week later, all mice received a booster of 10 µg VLPs by gavage. An immediate and strong secondary antibody response was induced in all 5 mice, including the mice whose primary antibody response was below detectable levels. A peak IgG response with GMT of 2487 was measured 2 weeks after boosting. Mice fed control tomato powder showed no response with IgG GMT remaining less than 40, three weeks after booster. Similar profiles were observed in the groups that were gavaged with 100 µg VLPs and those that ingested potato vaccine. For potato vaccine, a single boost after IgG titers returned to a baseline gave an instant and strong increase in antibody titers, with a peak of 3688 in 2 weeks following boosting, indicating memory cells were established. For groups fed with high dosages in tomato, the induced antibody responses were long-lived, for example, IgG GMT in group consuming 1.2 g tomato powder was still as high as 2000 at 180 dpi. This group did not return to baseline before boosting. A booster with gavage of 10 μg VLPs resulted in 10-fold increase in IgG GMT.

Example 24

Antigen in Mouse Pellet

To determine if rNV survives passage through the mouse gut, mouse fecal pellets were assayed by ELISA. Antigen levels were closely correlated to the amount mice ingested. Western blotting showed that the air-dried materials were less degraded in the intestine, which may explain why air-dried fruit is stronger immunogen, especially at 0.8 g dose or above.

Example 25

Characteristics of *Quillaja* Formulation with Plant-Made Vaccines

One aspect of the present invention involves preparing an oral vaccine to Norwalk virus including an extract of *Quillaja saponaria* (QS). In addition to the adjuvant data provided herein (see FIG. 15 and discussion thereof above), food grade *Quillaja saponaria* has been used on multiple occasions for oral vaccine evaluation. Patent application WO/011755A2 (which is hereby incorporated by reference in its entirety) describes the significant improvement in boosting titers when *Quillaja* was given in addition to transgenic potato materials expressing Hepatitis B surface antigen. Further examples of oral efficacy and safety in mice are provided in that reference. Additionally, Walmsley et al., "Passive Immunization of Mice Pups Through Oral Immunization of Dams with a Plant-Derived Vaccine," *Immunology Letters* 86:71-76 (2003) (which is hereby incorporated by reference in its entirety) describe the use of the same food grade QS extract (Garuda International, Lemon Cove, Calif.) in mice and vole oral feeding trials, and did not observe any adverse reactions at a 0.25% ratio to plant material. In that case, a clear effect of the adjuvant on improving immunogenicity of LTB was not observed.

QS may be the most convenient and efficacious option for supplementing the oral immunogenicity of plant-made vaccines (PMVs) (for a review see Kirk et al., "Application of *Quillaja saponaria* Extracts as Oral Adjuvants for Plant-Made Vaccines," *Expert Opinion Biol Ther* 4(6):947-958 (2004), which is hereby incorporated by reference in its entirety). *Quillaja saponaria* is traditionally derived by aqueous extraction of the dried inner bark, or cortex, of the *Quillaja saponaria* Molina tree (family Rosaceae). Partial purification of QS from crude (food grade) extract results in QuilA, which is contained in several veterinary vaccines. Further purification provides concentrated saponin fractions such as QS-21 and QS-7. Food-grade QS is available cheaply in large volume and from a multitude of manufacturers. The specific characteristics and immunostimulatory properties may show some variability depending on the sources and methods employed by each manufacture. It is unclear whether there is a sufficient difference between manufacturers to warrant a detailed comparison of humoral and cellular responses for different sources of QS extract in order to determine which source is best for a specific vaccine target. Commercial sources of QS extract are available in liquid or dry powder form. Downstream processing of PMVs involving dry milling and mixing of a powdered QS extract with a powdered transgenic plant material provides a highly convenient method of batch formulation. Powdered QS extract shows high stability when stored in a dry environment and at close to pH 5. This is consistent with the preferred conditions for some PMVs under development at present, especially powdered transgenic tomato (Walmsley et al., "Passive Immunization of Mice Pups Through Oral Immunization of Dams with a Plant-Derived Vaccine," *Immunology Letters* 86:71-76 (2003); Walmsley et al., "Expression of the B subunit of *Escherichia coli* heat Labile Enterotoxin as a Fusion Protein in Transgenic Tomato," *Plant Cell Report* 22(7):502-508 (2003); Walmsley et al., "Efficacy of an Edible, Plant-Derived Immunocontraceptive Vaccine in Mice and Voles," *NFID Sixth Annual Conference on Vaccine Research*, Arlington, Va. (2003); Kirk D., "Model Production of a Potent Plant-Made Vaccine," *Sixth Annual Conference on Vaccine Research*, Slide Presentation, Arlington, Va., May 2003), which are hereby incorporated by reference in their entirety). The strategic advantage of PMVs as a new technology for human vaccines is dependent on formulation of components in a dry state to retain ambient stability and packaging qualities and maintain oral activity over extended periods. However, efficacy of highly purified QS fractions, such as QS-21, when delivered orally, has been reported by only one group (Boyaka et al., "Oral QS-21 Requires Early IL-4 Help for Induction of Mucosal and Systemic Immunity," *J Immunology* 166:2283-2290 (2001), which is hereby incorporated by reference in its entirety). It is proposed that the food-grade extract may provide a more robust immune response than use of a single saponin fraction. This assumption is supported by emerging reports where QS-7 provided a synergistic effect with QS-21, specifically by enhancing induction of CD8+ cells (Pink et al., "4th Meeting on Novel Adjuvants Currently in/close to Human Clinical Testing World Health Organization—Organisation Mondiale de la Santé, Fondation Mérieux, Annecy, France, 23-25 Jun. 2003," *Vaccine* 22(17-18):2097-2102 (2004), which is hereby incorporated by reference in its entirety). In the absence of any toxicity data to the contrary, use of the food-grade extract is expected to fit well with both the immunogenic and manufacturing feasibility aspects of PMV technology.

As a non-denaturing adjuvant, QS extract may be preferred for use with conformation-dependent antigens, subunit proteins and structural epitopes. PMVs are used as a method of producing subunit proteins or antigens with cellular encapsulation to protect against protein degradation. It is unclear at what point cellular disruption must be maintained during oral administration of PMVs in humans for maximum immunogenicity; however, use of an adjuvant with known non-denaturing properties would clearly be preferred. The priming effect reported by Chavali and Campbell (Chavali et al., "Adjuvant Effects of Orally Administered Saponins on Humoral and Cellular Immune Responses in Mice," *Immunobiology* 174(3):347-359 (1987), which is hereby incorporated by reference in its entirety) 4-16 hr prior to vaccination may also be useful in co-delivery with PMVs. The delayed digestion of plant material in the lower intestine may allow QS extract to induce some potentiating of the mucosal linings by QS extract prior to release and immunogenic presentation of the antigen. This could be further leveraged for on-feed veterinary PMVs where ingestion of the vaccine may occur over several hours.

Previous toxicity studies and the data provided here suggest that a safe level of QS extract intake may be as low as 400 mg·kg−1, 80-fold higher than the upper limit of the ADI recommended by JECFA. This level has been used in all animal trials so far and correlates to a range of 0.2-0.33% of the PMV formulation by weight. In recent reports describing use of powdered PMVs for human vaccination (Kirk D., "Model Production of a Potent Plant-Made Vaccine," *Sixth Annual Conference on Vaccine Research*, Slide Presentation, May 2003); Tacket et al., "Immunogenicity of a Recombinant Bacterial Antigen Delivered in Transgenic Corn," *Sixth Annual Conference on Vaccine Research*, Arlington, Va., May 2003), which are hereby incorporated by reference in their entirety), the actual or proposed oral doses were 2.1 and 5 g, respectively. A formulation maintaining delivery of 400 mg·kg−1 of QS extract would require 26 g of the adjuvant in a volunteer of average weight (65 kg). Clearly, this level cannot be carried forward practically in humans or larger animal vaccines. A formulation at the upper limit of the recommended ADI (5 mg·kg−1) would require 325 mg of QS extract; however, this would equate to a formulation ratio of 6.5% for a 5 g dose or 16% for a 2.1 g dose. As a compromise, an oral formulation for human vaccination comprising 1% QS extract by weight in a 5 g dose would equate to an average exposure of 0.77 mg·kg−1 (15.4% of the ADI). Oral delivery of a 5 g dose with such a formulation would exceed previous preclinical formulation ratios by 3-10-fold; however, it would represent a 650-fold decrease or just 0.15% of the relative exposure levels used in preclinical experiments, an appropriate bias towards safety for initial human clinical evaluation.

Thus, it appears that QS is a safe, effective adjuvant when used as an adjuvant in orally delivered vaccinations. The oral vaccine of the present invention may be formulated to include a dose of a QS extract in the range of 0.01 mg to 10 mg per kg of body weight as an immunogenicity adjuvant.

Example 26

Figure 20:
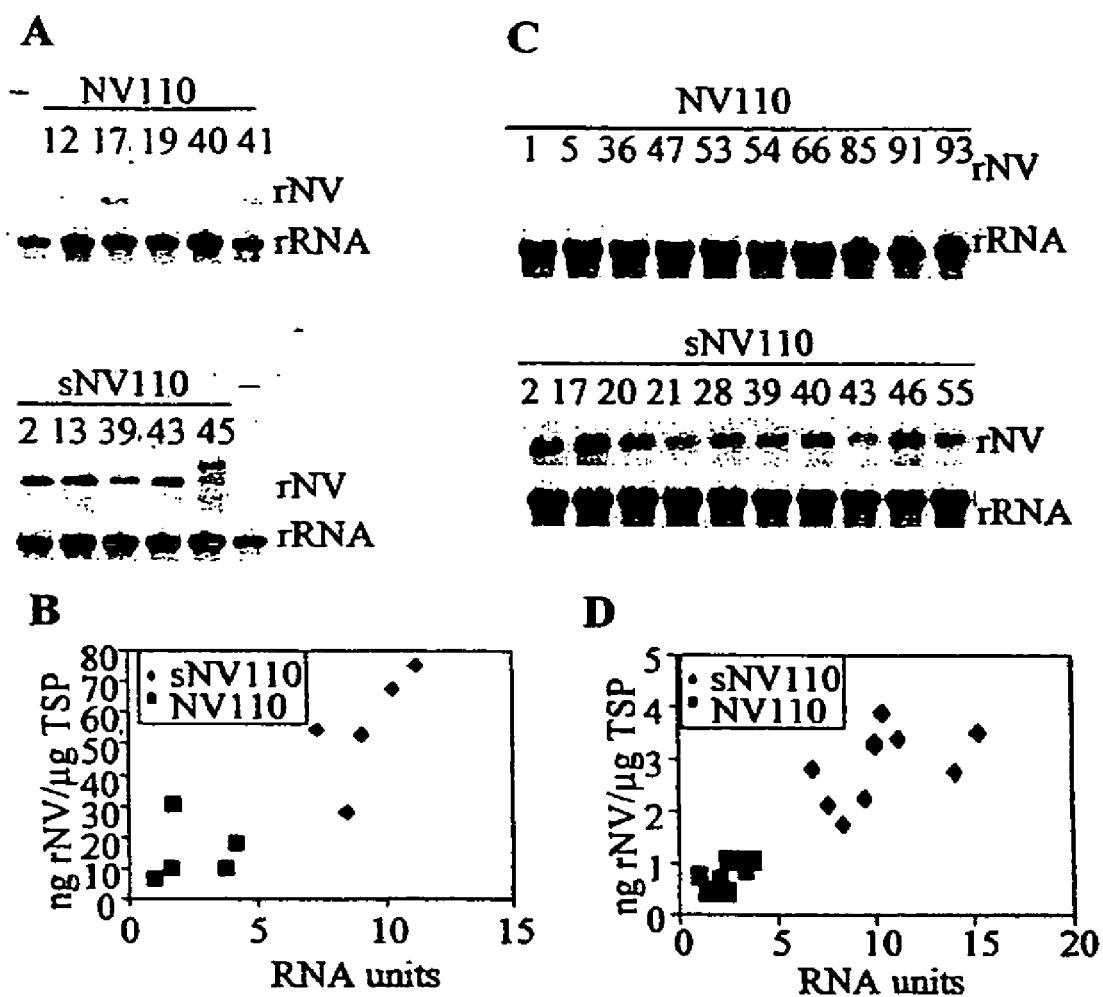
In FIG. 20D, the rNVCP vs. mRNA in potato tubers was plotted as in FIG. 20B.

Comparison of Immunogenicity of NVCP Transgenic Potato and sNVCP Transgenic Tomato Production of rNV was previously reported in tobacco and potato plants (Mason et al., "Expression of Norwalk Virus Capsid Protein in Transgenic Tobacco and Potato and its Oral Immunogenicity in Mice," *Proc Natl Acad Sci USA* 93:5335-5340 (1996), which is hereby incorporated by reference in its entirety), and oral immunization with either tobacco-derived or raw potato tubers stimulated the production of humoral and mucosal antibody responses in mice. Further, human clinical trials demonstrated that 95% of volunteers who ate uncooked potatoes containing rNV developed an immune response of some kind (Tacket et al., "Human Immune Responses to a Novel Norwalk Virus Vaccine Delivered in Transgenic Potatoes," *J Infect Dis* 182:302-305 (2000), which is hereby incorporated by reference in its entirety). In both animal and clinical studies, however, the antibody titers were low or moderate. Thus, it appeared that immunogenicity was limited by either the amount of rNV subunits produced, their assembly into VLPs within plant cells, or the concentration of the antigen in the delivery material. In order to develop a more efficacious oral vaccine, several strategies were exploited to enhance expression of rNV and/or assembly efficiency of rNV VLPs in plants. Here rNV expression was exploited by using a plant-optimized sNVCP gene, and about 4-fold increase in rNV accumulation in tomato and potato plants was achieved compared to the native NVCP gene, as shown in FIGS. 20A-B. The rate of VLP assembly was not significantly increased in plants expressing sNVCP, although the amount of the total VLPs was improved on a dry weight basis due to overall enhanced expression. The studies presented in the Examples above were performed to test the potential of tomato fruit and potato tuber, with enhanced accumulation of rNV and VLPs, to provoke stronger immune response in a mouse model. Also examined was whether there was correlation between immune response and doses, which will be information that is useful in the design of human clinical trials using plant-derived rNV immunogen.

Four feedings of 0.4 g freeze-dried tomato powder, without any adjuvant, induced NV-specific serum IgG and mucosal IgA in 80-100% of mice. Four doses of 0.8 g tomato powder consistently gave serum and intestinal antibody responses in all mice. Further, two feedings of 1.2 grams of transgenic tomato powder, containing ~192 µg rNV/dose or 60 µg VLPs/dose, given 2 days apart, consistently gave primary serum and fecal antibody responses in all mice with IgG and IgA GMTs of 64 and 1718 at 11 dpi, whereas only 20 to 40% of mice had a detectable serum and fecal antibodies after oral administration of 2 doses of 100 µg purified rNV VLPs by gavage. Two additional feedings with the same dose of tomato vaccine resulted in robust increases in both systemic and mucosal responses with a peak of IgG GMT of 6775 at 55 dpi, and that of IgA GMTs of 10681 at 27 dpi, which were significantly higher than those obtained by gavage. Though 1.2 g tomato powder contained ~192 µg rNV, it only contained 60 µg VLPs (38 nm) in total.

The success of immunization with tomato rNV may be due to several factors. First, the cell wall matrix and membrane materials of plants may serve as bioencapsulation elements, which would allow rNV to survive exposure to the enzymes in the gut. Oral immunization with purified rNV VLPs, which, although they are stable in acid pH in stomach, required delivery of large doses of VLPs to maintain immunogenicity. This may be due to enzymatic degradation as the VLPs traverse the gastrointestinal tract (Ball et al., "Oral Immunization with Recombinant Norwalk Virus-Like Particles Induces a Systemic and Mucosal Immune Response in Mice," *J Virol* 72:1345-1353 (1998); Guerrero et al., "Recombinant Norwalk Virus-Like Particles Administered Intranasally to Mice Induce Systemic and Mucosal (Fecal and Vaginal) Immune Responses.," *J Virol* 75:9713-9722 (2001), which are hereby incorporated by reference in their entirety). The natural bioencapsulation of the protein within plant cells may permit slow and lasting release of at least some VLPs, which are taken up readily by M cells of Peyer's patches, where they stimulate both the local and common mucosal immune system. Alternatively, the VLPs may interact with a specific enterocyte receptor to facilitate uptake and presentation to immune cells (Ball et al., "Oral Immunization with Recombinant Norwalk Virus-Like Particles Induces a Systemic and Mucosal Immune Response in Mice," *J Virol* 72:1345-1353 (1998); Guerrero et al., "Recombinant Norwalk Virus-Like Particles Administered Intranasally to Mice Induce Systemic and Mucosal (Fecal and Vaginal) Immune Responses.," *J Virol* 75:9713-9722 (2001); White et al., "Attachment and Entry of Recombinant Norwalk Virus Capsids to Cultured Human and Animal Cell Lines," *J Virol* 70:6589-6597 (1996), which are hereby incorporated by reference in their entirety).

Secondly, α-tomatine, an alkaloid glycoside of tomato (Friedman, "Tomato Glycoalkaloids: Role in the Plant and in the Diet," *J Agricultural and Food Chemistry* 50:5751-5780 (2002), which is hereby incorporated by reference in its entirety), may serve as a natural adjuvant potentiating immune responses in mice. A molecular aggregate formulation, which was based on α-tomatine, cholesterol, and phosphatidylethanolamine, has been reported to act as an effective adjuvant to augment either humoral or cellular immune responses (Rajananthanan et al., "Evaluation of Novel Aggregate Structures as Adjuvants: Composition, Toxicity Studies and Humoral Responses," *Vaccine* 17:715-730 (1999);

Rajananthanan et al., "Novel Aggregate Structure Adjuvants Modulate Lymphocyte Proliferation and Th1 and Th2 Cytokine Profiles in Ovalbumin Immunized Mice," *Vaccine* 18:140-152 (1999); Heal et al., "Potentiation by a Novel Alkaloid Glycoside Adjuvant of a Protective Cytotoxic T cell Immune Response Specific for a Preerythrocytic Malaria Vaccine Candidate Antigen," *Vaccine* 19:4153-4161 (2001), which are hereby incorporated by reference in their entirety). In these experiments, however, it is unclear whether α-tomatine alone was responsible for boosting oral immunogenicity. In addition, tomatine is abundant in wild-type but substantially lower in cultivated tomato. Meanwhile, α-tomatine level is high in tomato leaves and green fruit (74 µg/g DW), decreasing substantially by 10 days after flowering, and is only present at an approximate concentration of 70 ng/g DW in ripening and ripened fruit (Friedman, "Tomato Glycoalkaloids: Role in the Plant and in the Diet," *J Agricultural and Food Chemistry* 50:5751-5780 (2002), which is hereby incorporated by reference in its entirety). Further, potato also contains limited α-tomatine, but did not immunize as efficiently as tomato rNV 27 (below).

Another explanation could be that smaller-sized particles (23 nm) contributed to immunogenicity in mice. The proportion of 23 nm particles was roughly estimated to range from 25 to 42% in tomato extracts (FIGS. 22A-G).

Similarly, the expression of rNV resulted in the assembly of particles of two sizes in an insect cell system, where the amount of smaller-sized particles varied from one preparation to another, from 0 to 30% of the total population of the particles (White et al., "Biochemical Characterization of a Smaller Form of Recombinant Norwalk Virus Capsids Assembled in Insect Cells," *J Virol* 71:8066-8072 (1997); White et al., "Attachment and Entry of Recombinant Norwalk Virus Capsids to Cultured Human and Animal Cell Lines," *J Virol* 70:6589-6597 (1996), which are hereby incorporated by reference in their entirety). Particles of two sizes with similar morphology also occurred in stool samples from patients infected with a human *calicivirus* (Taniguchi et al., "Further Studies of 35-40 nm Virus-Like Particles Associated with Outbreaks of Acute Gastroenteritis," *J Medical Microbiology* 14:107-118 (1981), which is hereby incorporated by reference in its entirety). In fact, the self-assembly of viral capsids composed of a single structural protein into two structures has been found for a number of T=3 icosahedral RNA viruses (Harrison et al., in Fields et al., eds., *Field Virology* Philadelphia, Pa.: Lippincott-Raven Publishers, pp. 59-99 (1996), which is hereby incorporated by reference in its entirety). The mechanism that controls the assembly of capsid proteins into larger or smaller particles is still unknown, but it might be related to charge configuration in the putative nucleation complex (five-dimer nuclei), and thus might be regulated by pH, divalent cations, and the presence of additional charged domains (Erickson et al., "The Structure of a T=1 Icosahedral Empty Particle from Southern Bean Mosaic Virus," *Science* 229:625-629 (1985), which is hereby incorporated by reference in its entirety). Since biochemical, antigenic, and the binding activity to cultured human intestinal cells were conserved in the two type of particles (White et al., "Biochemical Characterization of a Smaller Form of Recombinant Norwalk Virus Capsids Assembled in Insect Cells," *J Virol* 71:8066-8072 (1997); White et al., "Attachment and Entry of Recombinant Norwalk Virus Capsids to Cultured Human and Animal Cell Lines," *J Virol.* 70:6589-6597 (1996), which are hereby incorporated by reference in their entirety), it would be reasonable to believe that particles of 23 nm in tomato materials might also somehow be immunogenic in this experiment. Further study on the immunogenicity of 23 nm particles is needed.

It is shown herein that rNV in air-dried tomato fruit was a slightly more potent immunogen than that in freeze-dried tomato powder. A possible explanation is that more of the plant cell matrix and membrane system is conserved by air-drying, and more protection of rNV is provided. As little as two oral immunizations with 0.8 g of air-dried fruit, in the absence of any adjuvant, can establish consistent systemic and mucosal immune responses in all mice. This result has a particular importance, especially in the developing countries, because it is realistic way of fruit processing and storage. It provides a basis for implementation of large-scale and sustainable vaccination.

Figure 22:
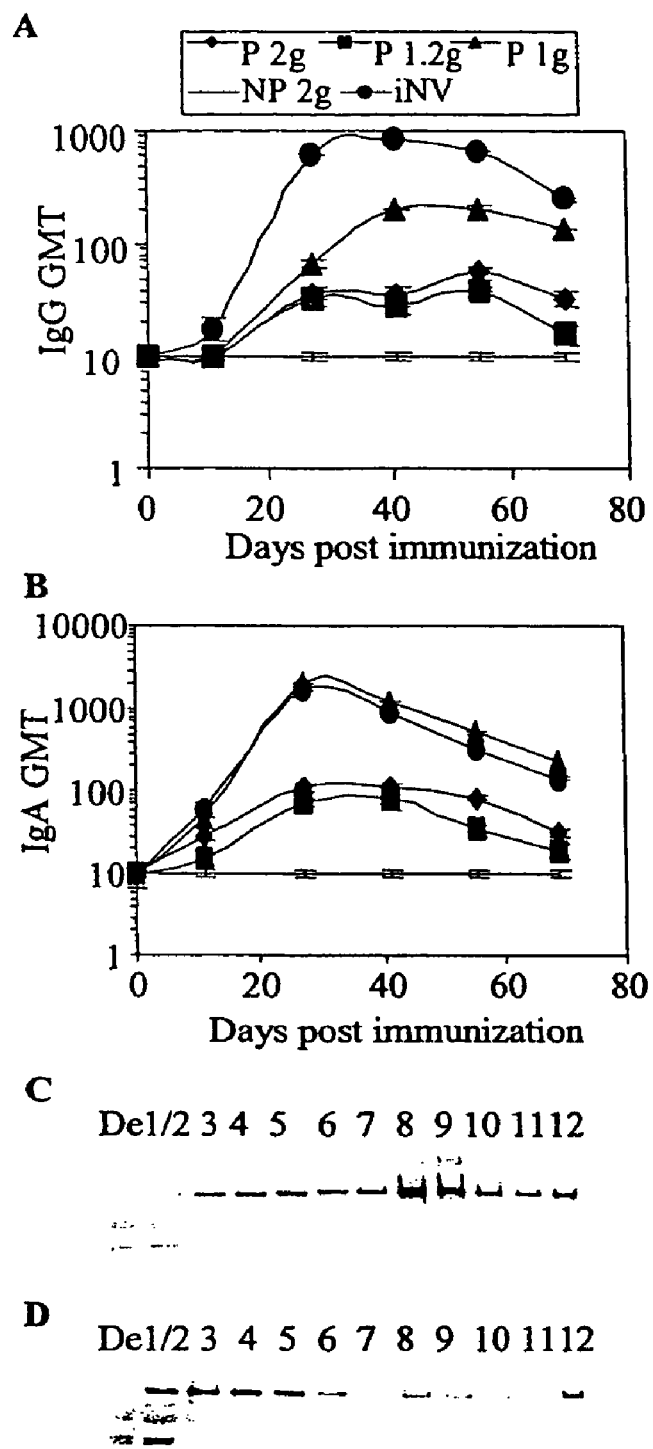
FIGS. 22A-D show the immunogenicity of transgenic potato expressing synthetic NVCP gene.

It is also shown herein that potato tuber rNV provides less immunogenicity than tomato materials. One reason was that VLPs were disassembled in some higher-dose groups where potato powder was mixed with water. Potato browning (either enzymic or nonenzymic) often results in phenolic- or sugar-protein complexes and therefore destablizes VLPs (Belitz et al., "*Fruits and Fruit Products,*" Springer-Verlag (1987); deMan, in *Principles of Food Chemistry* (3rd edition) 120-129 (An Aspen, Gaithersburg; 1999), which are hereby incorporated by reference in their entirety). This explains why only 20-40% of mice that ingested higher doses of rNV potato powder had detectable immune responses, as shown in FIGS. 22A-B). These results confirmed the suggestion that soluble proteins or oligomers induce little or no immune response (Ball et al., "Oral Immunization with Recombinant Norwalk Virus-Like Particles Induces a Systemic and Mucosal Immune Response in Mice," *J Virol* 72:1345-1353 (1998); Tacket et al., "Human Immune Responses to a Novel Norwalk Virus Vaccine Delivered in Transgenic Potatoes," *J Infect Dis* 182:302-305 (2000), which are hereby incorporated by reference in their entirety). For the group that was fed non-browning powder (not mixed with water prior to delivery), low titers of serum antibodies were detected, though all mice had positive responses. This result suggested that potato 'Desiree' might contain some immuno-inhibiting substance.

Figure 25:
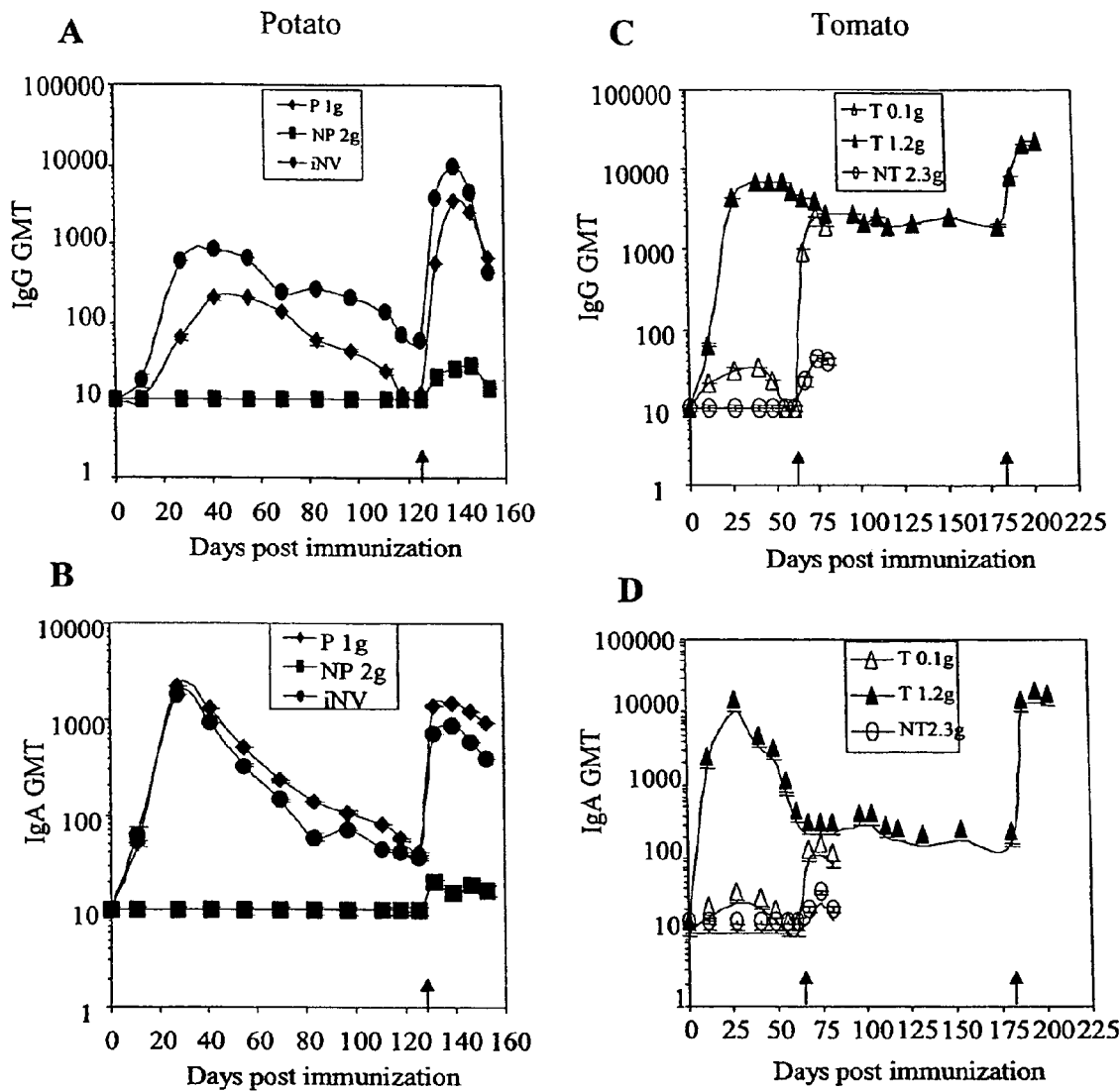
FIGS. 25A-D show the booster response seen by gavage of 10 µg iNV VLPs to each mouse.

The results described herein with both tomato and potato vaccine showed that they were not tolerogenic. After each oral feeding, the IgG and IgA titers increased or the number of responders increased. Further, one booster after 6 month with low amount of VLPs (10 µg/mouse) increased serum IgG and intestinal IgA responses (FIG. 25D, tomato data). Establishment of a memory response is one of the key factors for vaccine design and implementation (Kong et al., "Oral Immunization with Hepatitis B Surface Antigen Expressed in Transgenic Plants," *Proc Natl Acad Sci USA* 98:11539-11544 (2001), which is hereby incorporated by reference in its entirety). The present invention shows that feeding 0.1 g tomato powder and 1 g of potato powder stimulated a primary immune response, and that a single booster of low dose provoked a rapid and robust recall response after the specific antibodies had declined to baseline. No responses to boost were obtained in mice that were fed nontransgenic materials, showing that the boosting response elicited in mice was indeed the result of priming and establishment of immune memory to rNV VLPs presented in the gut. The disclosures that repeated exposures to low dose of tomato vaccine does not cause immune tolerance, and that immune memory cells have been established in these mice, could provide a basis of a new practical immunization strategy. Such a multiple delivery of low doses of oral vaccine is a useful approach to large-scale of immunization in developing countries, especially for infants and young children, who eat small quantities of food at one time. Taken together, it is shown in the present invention that oral immunization of rNV expressed in transgenic tomato and potato can elicit systemic and mucosal antibody responses. Further, rNV in tomato is a more potent immunogen, especially in air-dried tomato fruit. The robust immunogenicity of tomato vaccine likely resulted from natural bioencapsulation of plant cell matrix and membrane systems, and perhaps from large amount of smaller-sized particles, as well as some amount of natural adjuvants like tomatine. The results shown herein will be used to design future Phase I human trials.

Thus, the present invention provides transgenic plants and fruits, including, but not limited to, tomato fruit, as a vehicle for expression and oral delivery of rNV. Previous studies in potato were limited by low levels of expression of NVCP and inefficient assembly of immunogenic VLPs (Mason et al., "Expression of Norwalk Virus Capsid Protein in Transgenic Tobacco and Potato and its Oral Immunogenicity in Mice," *Proc Natl Acad Sci USA* 93:5335-5340 (1996), Tacket et al., "Human Immune Responses to a Novel Norwalk Virus Vaccine Delivered in Transgenic Potatoes," *J Infect Dis* 182:302-305 (2000), which are hereby incorporated by reference in their entirety). The present invention uses a plant-optimized NVCP gene with preferred codons and aberrant mRNA processing signals removed to produce transgenic tomato fruit having higher expression levels of rNV than transgenic NVCP potato tubers, and which is also a more potent oral immunogen. Furthermore, air-dried tomato fruit is shown to induce a more robust immune response than freeze-dried powder, indicating that a very convenient stabilization process has utility for tomato-derived vaccine production. This result is particularly important for vaccination of large populations in developing countries with limited technology infrastructure. These studies serve as a model for oral immunization with drying-stabilized plant-made vaccines.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

SEQUENCE LISTING

```
<160> NUMBER OF SEQ ID NOS: 12

<210> SEQ ID NO 1
<211> LENGTH: 1593
<212> TYPE: DNA
<213> ORGANISM: Norwalk virus capsid protein, native

<400> SEQUENCE: 1
atgatgatgg cgtctaagga cgctacatca agcgtggatg gcgctagtgg cgctggtcag        60
ttggtaccgg aggttaatgc ttctgaccct cttgcaatgg atcctgtagc aggttcttcg       120
acagcagtcg cgactgctgg acaagttaat cctattgatc cctggataat taataatttt       180
gtgcaagccc cccaaggtga atttactatt tccccaaata ataccccggg tgatgttttg       240
tttgatttga gtttgggtcc ccatcttaat cctttcttgc tccatctatc acaaatgtat       300
aatggttggg ttggtaacat gagagtcagg attatgctag ctggtaatgc ctttactgcg       360
gggaagataa tagtttcctg catacccct ggttttggtt cacataatct tactatagca       420
caagcaactc tctttccaca tgtgattgct gatgttagga ctctagaccc cattgaggtg       480
cctttggaag atgttaggaa tgttctcttt cataataatg atagaaatca acaaaccatg       540
cgccttgtgt gcatgctgta cacccccctc cgcactggtg gtggtactgg tgattcttt       600 gtagttgcag ggcgagttat gacttgcccc agtcctgatt ttaatttctt gttttttagtc       660 cctcctacgg tggagcagaa aaccaggccc ttcacactcc caaatctgcc attgagttct       720
ctgtctaact cacgtgcccc tctcccaatc agtagtatcg gcatttcccc agacaatgtc       780
cagagtgtgc agttccaaaa tggtcggtgt actctggatg gccgcctggt tggcaccacc       840
ccagtttcat tgtcacatgt tgccaagata agagggacct ccaatggcac tgtaatcaac       900
cttactgaat tggatggcac acccttcac ccttttgagg gccctgcccc cattgggttt       960
ccagacctcg gtggttgtga ttggcatatc aatatgacac agttggcca ttctagccag      1020 acccagtatg atgtagacac caccccctgac acttttgtcc cccatcttgg ttcaattcag      1080
gcaaatggca ttggcagtgg taattatgtt ggtgttctta gctggattc cccccatca      1140 cacccgtctg gctcccaagt tgaccttttgg aagatcccca attatgggtc aagtattacg      1200
```

```
gaggcaacac atctagcccc ttctgtatac ccccctggtt tcggagaggt attggtcttt   1260
ttcatgtcaa aaatgccagg tcctggtgct tataatttgc cctgtctatt accacaagag   1320
tacatttcac atcttgctag tgaacaagcc cctactgtag gtgaggctgc cctgctccac   1380
tatgttgacc ctgataccgg tcggaatctt ggggaattca agcataccc tgatggtttc   1440 ctcacttgtg tccccaatgg ggctagctcg ggtccacaac agctgccgat caatggggtc   1500
tttgtctttg tttcatgggt gtccagattt tatcaattaa agcctgtggg aactgccagc   1560
tcggcaagag gtaggcttgg tctgcgccga taa                                1593
```

<210> SEQ ID NO 2
<211> LENGTH: 530
<212> TYPE: PRT
<213> ORGANISM: Norwalk virus capsid protein, native

<400> SEQUENCE: 2

```
Met Met Met Ala Ser Lys Asp Ala Thr Ser Ser Val Asp Gly Ala Ser
 1               5                  10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Ile Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300
```

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
            325                 330                 335

His Ser Ser Gln Thr Gln Tyr Asp Val Asp Thr Thr Pro Asp Thr Phe
        340                 345                 350

Val Pro His Leu Gly Ser Ile Gln Ala Asn Gly Ile Gly Ser Gly Asn
    355                 360                 365

Tyr Val Gly Val Leu Ser Trp Ile Ser Pro Pro Ser His Pro Ser Gly
370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530

<210> SEQ ID NO 3
<211> LENGTH: 1593
<212> TYPE: DNA
<213> ORGANISM: Artificial Sequence
<220> FEATURE:
<223> OTHER INFORMATION: Description of Artificial Sequence: Synthetic
      plant-optimized Norwalk virus capsid protein

<400> SEQUENCE: 3
atgatgatgg cttctaagga tgctacatca tctgtggatg agctagtgg agctggtcaa      60 ttggttccag aggttaatgc ttctgaccct cttgctatgg atcctgtagc aggttcttcc     120
acagcagttg ctactgctgg acaagttaat cctattgatc catggataat taacaacttt    180
gtgcaagccc cccaaggtga attcactatt tccccaaaca cacccccagg tgatgttttg    240
tttgatttga gttgggtcc ccatcttaat cctttcttgc tccatctctc acaaatgtat     300
aatggttggg ttggtaacat gagagttagg attatgcttg ctggtaatgc ctttactgct    360
ggtaagataa tagtttcttg catacccct ggttttggtt cacataatct tactatagca     420
caagcaactc tctttcctca tgtgattgct gatgttagga ctcttgaccc cattgaggtg    480
cctttggaag atgttaggaa tgttctcttt cataacaacg atagaaatca acaaccatg     540 aggcttgtgt gcatgctcta caccccttg aggactggtg gtggtactgg tgattctttt    600
gtagttgcag aaggttatg gacttgccca gtcctgatt ttaatttctt gttttagtc       660 cctcctacag tggagcaaaa aaccaggccc ttcacactcc caaatctccc attgagttct    720

```
ctctctaact caagagcccc tctcccaatt agtagtatgg gcatttcccc agacaatgtc      780
caaagtgtgc aattccaaaa tggtaggtgt actcttgatg gaagacttgt tggcaccacc      840
ccagtaagct tgtcacatgt tgccaagata agaggtacct ccaatggcac tgtgatcaac      900
cttactgaat tggatggcac acccttcac cttttgagg gccctgcccc cattggattt       960
ccagatcttg gtggttgtga ttggcatatc aatatgacac aatttggcca ttctagccaa     1020
acccaatatg atgtcgacac cacccctgac acttttgtcc cccatcttgg ttcaattcaa     1080
gcaaatggca ttgaagtgg taattatgtt ggtgttcttt cttggatttc ccccccatca      1140
cacccatctg gctcccaagt tgacctttgg aagatcccca attatggatc aagtattact     1200
gaggcaacac atcttgcccc ttctgtatac ccccctggtt ttggagaggt attggtcttt     1260
ttcatgtcaa aaatgccagg tcctggcgct tataatttgc catgtctctt accacaagag     1320
tacatttcac atcttgctag cgagcaagcc ctactgtag gtgaggctgc cctgctccac      1380
tatgttgacc ctgatactgg taggaatctt ggagaattca aagcatacc tgatggtttc      1440 ctcacttgtg tccccaatgg tgctagcagc ggtccacaac aactgccaat caatggtgtc     1500
tttgtctttg tttcatgggt gtcaagattt tatcaattaa agcctgtggg aactgcctct     1560
agcgcaagag gtaggcttgg tcttaggagg taa                                  1593

<210> SEQ ID NO 4
<211> LENGTH: 1593
<212> TYPE: DNA
<213> ORGANISM: Artificial Sequence
<220> FEATURE:
<223> OTHER INFORMATION: Description of Artificial Sequence:  Synthetic
      plant-optimized Nowalk virus capsid protein

<400> SEQUENCE: 4
atgatgatgg cttctaagga tgctacatca tctgtggatg gagctagtgg agctggtcaa       60
ttggttccag aggttaatgc ttctgaccct cttgctatgg atcctgtagc aggttcttcc      120
acagcagttg ctactgctgg acaagttaat cctattgatc catggataat taacaacttt      180
gtgcaagccc cccaaggtga attcactatt tccccaaaca caccccagg tgatgttttg       240 tttgatttga gtttgggtcc ccatcttaat cctttcttgc tccatctctc acaaatgtat      300
aatggttggg ttggtaacat gagagttagg attatgcttg ctggtaatgc ctttactgct      360
ggtaagataa tagtttcttg catacccct ggttttggtt cacataatct tactatagca       420
caagcaactc tctttcctca tgtgattgct gatgttagga ctcttgaccc cattgaggtg      480
cctttggaag atgttaggaa tgttctcttt cataacaacg atagaaatca acaaaccatg      540
aggcttgtgt gcatgctcta caccccttg aggactggtg tggtactgg tgattctttt        600 gtagttgcag aagggttat gacttgccca agtcctgatt ttaatttctt gttttagtc        660 cctcctacag tggagcaaaa aaccaggccc ttcacactcc caaatctccc attgagttct     720
ctctctaact caagagcccc tctcccaatt agtagtatcg gcatttcccc agacaatgtc     780
caaagtgtgc aattccaaaa tggtaggtgt actcttgatg gaagacttgt tggcaccacc      840
ccagtaagct tgtcacatgt tgccaagata agaggtacct ccaatggcac tgtgatcaac      900
cttactgaat tggatggcac acccttcac cttttgagg gccctgcccc cattggattt       960
ccagatcttg gtggttgtga ttggcatatc aatatgacac aatttggcca ttctagccaa    1020
acccaatatg atgtcgacac cacccctgac acttttgtcc cccatcttgg ttcaattcaa    1080
gcaaatggca ttgaagtgg taattatgtt ggtgttcttt cttggatttc ccccccatca     1140
```

```
cacccatctg gctcccaagt tgacctttgg aagatcccca attatggatc aagtattact    1200
gaggcaacac atcttgcccc ttctgtatac ccccctggtt ttggagaggt attggtcttt    1260
ttcatgtcaa aaatgccagg tcctggcgct tataatttgc catgtctctt accacaagag    1320
tacatttcac atcttgctag cgagcaagcc cctactgtag gtgaggctgc cctgctccac    1380
tatgttgacc ctgatactgg taggaatctt ggagaattca aagcatacc c tgatggtttc    1440 ctcacttgtg tccccaatgg tgctagcagc ggtccacaac aactgccaat caatggtgtc    1500
tttgtctttg tttcatgggt gtcaagattt tatcaattaa agcctgtggg aactgcctct    1560
agcgcaagag gtaggcttgg tcttaggagg taa                                 1593
```

<210> SEQ ID NO 5
<211> LENGTH: 1601
<212> TYPE: DNA
<213> ORGANISM: Artificial Sequence
<220> FEATURE:
<223> OTHER INFORMATION: Description of Artificial Sequence: Contig
      Sequence

<400> SEQUENCE: 5

```
atgatgatgg cktctaagga ygctacatca wgctgtggat ggmgctagtg gmgctggtca      60
rttggtwccr gaggttaatg cttctgaccc tcttgcwatg gatcctgtag caggttcttc     120
sacagcagty gckactgctg gacaagttaa tcctattgat ccmtggataa ttaayaaytt     180
tgtgcaagcc ccccaaggtg aattyactat ttccccaaay aayaccccmg gtgatgtttt     240
gtttgatttg agtttgggtc cccatcttaa tcctttcttg ctccatctmt cacaaatgta     300
taatggttgg gttggtaaca tgagagtyag gattatgctw gctggtaatg cctttactgc     360
kggkaagata atagtttcyt gcataccccc tggttttggt tcacataatc ttactatagc     420
acaagcaact ctcttttccwc atgtgattgc tgatgttagg actctwgacc ccattgaggt     480
gcctttggaa gatgttagga atgttctctt tcataayaay gatagaaatc aacaaaccat     540
gmgscttgtg tgcatgctst acacccccyt smgsactggt ggtggtactg gtgattcttt     600
tgtagttgca ggaagcgagt tatgacttgc ccmagtcctg attttaatt t cttgtttta     660 gtccctccta crgtggagca raaaaccagg cccttcacac tcccaaatct sccattgagt     720 tctctststcta actcamgwgc ccctctccca atyagtagta tsggcatttc cccagacaat     780
gtccaragtg tgcarttcca aaatggtmgg tgtactctkg atggmmgmct kgttggcacc     840
accccagtww gcattgtcac atgttgccaa gataagaggk acctccaatg gcactgtrat     900
caaccttact gaattggatg gcacacccct tcacccttt t gagggccctg ccccccattgg     960 rtttccagay ctyggtggtt gtgattggca tatcaatatg acacartttg gccattctag    1020
ccaracccar tatgatgtmg acaccacccc tgacactttt gtcccccatc ttggttcaat    1080
tcargcaaat ggcattggma gtggtaatta tgttggtgtt cttwgcttgg atttcccccc    1140
catcacaccc rtctggctcc caagttgacc tttggaagat ccccaattat ggrtcaagta    1200
ttackgaggc aacacatctw gcccttctg tatacccccc tggtttygga gaggtattgg    1260 tcttttttcat gtcaaaaatg ccaggtcctg gygcttataa tttgccmtgt ctmttaccac    1320
aagagtacat tcacatctt gctagygarc aagcccctac tgtaggtgag gctgccctgc    1380
tccactatgt tgaccctgat acyggtmgga atcttggrga attcaaagca taccctgatg    1440
gtttcctcac ttgtgtcccc aatggkgcta gcwgcgggtc cacaacarct gccratcaat    1500
ggkgtctttg tctttgtttc atgggtgtcm agattttatc aattaaagcc tgtgggaact    1560
```
gccwgctmgc gcaagaggta ggcttggtct tagcgmsgat a                                    1601

<210> SEQ ID NO 6
<211> LENGTH: 530
<212> TYPE: PRT
<213> ORGANISM: Artificial Sequence
<220> FEATURE:
<223> OTHER INFORMATION: Description of Artificial Sequence: Synthetic
      plant-optimized Norwalk virus capsid protein

<400> SEQUENCE: 6

```
Met Met Met Ala Ser Lys Asp Ala Thr Ser Ser Val Asp Gly Ala Ser
 1               5                  10                  15

Gly Ala Gly Gln Leu Val Pro Glu Val Asn Ala Ser Asp Pro Leu Ala
             20                  25                  30

Met Asp Pro Val Ala Gly Ser Ser Thr Ala Val Ala Thr Ala Gly Gln
         35                  40                  45

Val Asn Pro Ile Asp Pro Trp Ile Ile Asn Asn Phe Val Gln Ala Pro
     50                  55                  60

Gln Gly Glu Phe Thr Ile Ser Pro Asn Asn Thr Pro Gly Asp Val Leu
 65                  70                  75                  80

Phe Asp Leu Ser Leu Gly Pro His Leu Asn Pro Phe Leu Leu His Leu
                 85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Ile Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350
```

-continued

```
Val Pro His Leu Gly Ser Ile Gln Ala Asn Gly Ile Gly Ser Gly Asn
            355                 360                 365

Tyr Val Gly Val Leu Ser Trp Ile Ser Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530

<210> SEQ ID NO 7
<211> LENGTH: 530
<212> TYPE: PRT
<213> ORGANISM: Artificial Sequence
<220> FEATURE:
<223> OTHER INFORMATION: Description of Artificial Sequence:  Consensus
      Sequence

<400> SEQUENCE: 7

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
```

```
                165                 170                 175
Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Ile Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
530

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Oligo
      primer
```

```
<400> SEQUENCE: 8
gaagtgacag atagctgggc                                                   20

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Oligo
      primer

<400> SEQUENCE: 9
tgaatagtgc atatcagcat acctta                                            26

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Oligo
      primer

<400> SEQUENCE: 10
cttgttttta gtccctccta cagt                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Oligo
      primer

<400> SEQUENCE: 11
caagcattct acttctattg cagc                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Oligo
      primer

<400> SEQUENCE: 12
gctagcaaga tgtgaaatgt actc                                              24
```

What is claimed is:

1. A synthetic nucleic acid molecule comprising a *Norovirus* capsid protein coding sequence, wherein the nucleic acid molecule is optimized for expression in plants to produce *Norovirus* capsid protein particles, wherein the nucleic acid molecule has the nucleotide sequence comprising SEQ ID NO:3.

2. A nucleic acid construct comprising:
   the synthetic nucleic acid molecule according to claim 1;
   a 5' DNA promoter sequence; and
   a 3' terminator sequence, wherein the promoter and the terminator are operatively coupled to the synthetic nucleic acid molecule to allow expression of the *Norovirus* capsid protein in a plant.

3. The nucleic acid construct according to claim 2, wherein the DNA promoter is a constitutive plant promoter.

4. An expression system comprising the nucleic acid construct according to claim 2.

5. The expression system according to claim 4, wherein the synthetic nucleic acid molecule is in a sense orientation in the nucleic acid construct.

6. An isolated host cell transformed with the nucleic acid construct according to claim 2.

7. The host cell according to claim 6, wherein the host cell is a bacterial cell or a plant cell.

8. The host cell according to claim 7, wherein the host cell is a plant cell.

9. The host cell according to claim 8, wherein the plant cell is selected from the group consisting of: a potato cell, a tobacco cell, and a tomato cell.

10. The host cell according to claim 9, wherein the plant cell is a tomato cell.

11. The host cell according to claim 9, wherein the plant cell is a tobacco plant cell.

12. The host cell according to claim 9, wherein the plant cell is a potato cell.

13. A plant transformed with the nucleic acid construct according to claim 2.

14. The plant according to claim 13, wherein the plant is selected from the group consisting of: potato, tobacco, and tomato.

15. The plant according to claim 14, wherein the plant is a tomato plant.

16. The plant according to claim 14, wherein the plant is a potato plant.

17. The plant according to claim 14, wherein the plant is a tobacco plant.

18. A component part of a plant transformed with the nucleic acid construct according to claim 2, wherein said component part includes the nucleotide sequence comprising SEQ ID NO:3.

19. A fruit of a plant transformed with the nucleic acid construct according to claim 2, wherein said fruit includes the nucleotide sequence comprising SEQ ID NO:3.

20. A plant seed transformed with the nucleic acid construct according to claim 2.

21. The plant seed according to claim 20, wherein the seed is a tomato plant seed.

22. The plant seed according to claim 20, wherein the seed is a potato plant seed.

23. The plant seed according to claim 20, wherein the seed is a tobacco plant seed.

24. A vaccine for immunization of a subject against infection by *Norovirus* comprising:
    a component of a plant transformed with the nucleic acid construct according to claim 2 and a pharmaceutical adjuvant, wherein said component includes the nucleotide sequence comprising SEQ ID NO:3.

25. The vaccine according to claim 24, wherein the pharmaceutical adjuvant comprises an extract of food grade *Quillaja saponaria*.

26. The vaccine according to claim 25, wherein the extract of food grade *Quillaja saponaria* is selected from the group consisting of Quil A and QS-21.

27. The vaccine according to claim 26, wherein the extract of food grade *Quillaja saponaria* is QS-21.

28. A liquid extract from the plant according to claim 13, wherein said liquid extract includes the nucleotide sequence comprising SEQ ID NO:3.

29. The vaccine according to claim 24, wherein the component is in powder form.

* * * * *

UNITED STATES PATENT AND TRADEMARK OFFICE
CERTIFICATE OF CORRECTION

PATENT NO. : 7,879,338 B2
APPLICATION NO. : 10/895791
DATED : February 1, 2011
INVENTOR(S) : Hamilton et al.

Page 1 of 1

It is certified that error appears in the above-identified patent and that said Letters Patent is hereby corrected as shown below:

Col. 1 at lines 7-10, delete the text "The subject matter of this application was made with support from the United States Government under National Science Foundation Grant No. BES-0109936. The U.S. Government may have certain rights in this invention." and insert the text --This invention was made with government support under Grant No. BES-0109936 awarded by the National Science Foundation. The government has certain rights in this invention.-- in its place.

Signed and Sealed this
Twenty-third Day of October, 2012

David J. Kappos
*Director of the United States Patent and Trademark Office*